(12) United States Patent
Whitten et al.

(10) Patent No.: US 7,402,579 B2
(45) Date of Patent: Jul. 22, 2008

(54) QUINOBENZOXAZINE ANALOGS AND COMPOSITIONS

(75) Inventors: Jeffrey P. Whitten, Santee, CA (US); Fabrice Pierre, La Jolla, CA (US); Michael Schwaebe, San Diego, CA (US)

(73) Assignee: Cylene Pharmaceuticals, Inc., San Diego, CA (US)

( * ) Notice: Subject to any disclaimer, the term of this patent is extended or adjusted under 35 U.S.C. 154(b) by 77 days.

(21) Appl. No.: 11/404,947

(22) Filed: Apr. 14, 2006

(65) Prior Publication Data

US 2006/0264634 A1    Nov. 23, 2006

Related U.S. Application Data

(60) Provisional application No. 60/671,760, filed on Apr. 15, 2005.

(51) Int. Cl.
| | |
|---|---|
| A61K 31/54 | (2006.01) |
| A61K 31/5377 | (2006.01) |
| A61K 31/4025 | (2006.01) |
| A61K 31/496 | (2006.01) |
| A61K 31/4178 | (2006.01) |
| C07D 265/38 | (2006.01) |
| C07D 273/04 | (2006.01) |
| C07D 233/54 | (2006.01) |
| C07D 413/02 | (2006.01) |
| C07D 413/12 | (2006.01) |
| C07D 417/04 | (2006.01) |

(52) U.S. Cl. .............. 514/228.2; 514/233.2; 514/229.5; 514/397; 514/422; 514/254.11; 544/99; 544/111; 544/60; 546/198; 548/311.7; 548/421

(58) Field of Classification Search .............. 514/229.5, 514/233.2, 228.2, 397, 422, 254.11, 338, 514/339, 321; 544/99, 60, 361, 111; 546/283.1, 546/198; 548/421, 311.7
See application file for complete search history.

(56) References Cited

U.S. PATENT DOCUMENTS

| 5,624,924 A | 4/1997 | Chu et al. |
| 2004/0029882 A1 | 2/2004 | Ledoussal et al. |
| 2005/0004160 A1 | 1/2005 | Whitten et al. |

FOREIGN PATENT DOCUMENTS

WO   WO 2004/091504   * 10/2004

OTHER PUBLICATIONS

Han et al., Trends Pharm. Sci. (2000) 21:136-142.
International Search Report and Written Opinion for PCT/US2006/014212, mailed Jul. 20, 2007, 8 pages.

\* cited by examiner

Primary Examiner—Joeseph McKane
Assistant Examiner—Yong Chu
(74) Attorney, Agent, or Firm—Morrison & Foerster LLP

(57) ABSTRACT

The present invention relates to quinobenzoxazines analogs having the general formula:

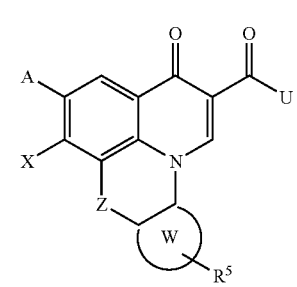

(1)

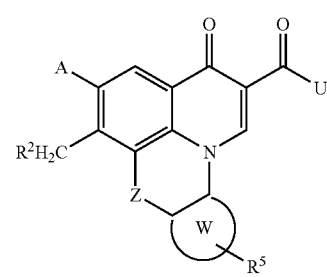

(1A)

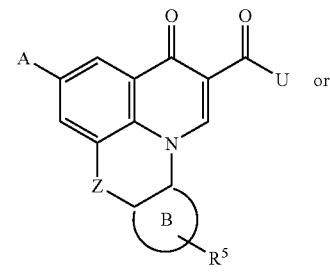

(2)

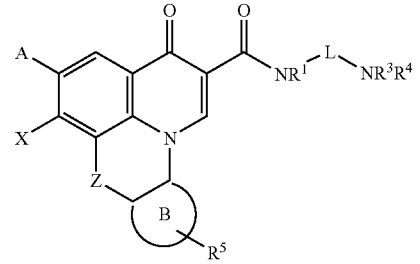

(3)

and pharmaceutically acceptable salts, esters and prodrugs thereof;
wherein A, U, W, X, Z, B, L, $R^1$, $R^3$, $R^4$ and $R^5$ are substituents.

The present invention also relates to methods for using such compounds.

6 Claims, No Drawings

SEQUENCE LISTING

```
<160> NUMBER OF SEQ ID NOS: 29

<210> SEQ ID NO 1
<211> LENGTH: 27
<212> TYPE: DNA
<213> ORGANISM: Homo sapiens

<400> SEQUENCE: 1
tggggagggt ggggagggtg gggaagg                                       27

<210> SEQ ID NO 2
<211> LENGTH: 37
<212> TYPE: DNA
<213> ORGANISM: Homo sapiens

<400> SEQUENCE: 2
gggggggggg gggcggggggc ggggcgggg gaggggc                            37

<210> SEQ ID NO 3
<211> LENGTH: 57
<212> TYPE: DNA
<213> ORGANISM: Homo sapiens

<400> SEQUENCE: 3 gggggggggac gcgggagctg ggggagggct tggggccagg gcggggcgct taggggg     57

<210> SEQ ID NO 4
<211> LENGTH: 28
<212> TYPE: DNA
<213> ORGANISM: Homo sapiens

<400> SEQUENCE: 4 aggaaggggga gggccggggg gaggtggc                                     28
```

```
<210> SEQ ID NO 5
<211> LENGTH: 22
<212> TYPE: DNA
<213> ORGANISM: Homo sapiens

<400> SEQUENCE: 5 agggggcgggg cggggcgggg gc                                              22

<210> SEQ ID NO 6
<211> LENGTH: 25
<212> TYPE: DNA
<213> ORGANISM: Homo sapiens

<400> SEQUENCE: 6
gggaggaagg gggcgggagc ggggc                                            25

<210> SEQ ID NO 7
<211> LENGTH: 32
<212> TYPE: DNA
<213> ORGANISM: Homo sapiens

<400> SEQUENCE: 7 gggggcggg ggcgggcgca ggggagggg gc                                      32

<210> SEQ ID NO 8
<211> LENGTH: 23
<212> TYPE: DNA
<213> ORGANISM: Homo sapiens

<400> SEQUENCE: 8
cggggcgggg cggggggcggg ggc                                             23

<210> SEQ ID NO 9
<211> LENGTH: 46
<212> TYPE: DNA
<213> ORGANISM: Homo sapiens

<400> SEQUENCE: 9
agaggaggag gaggtcacgg aggaggagga gaaggaggag gaggaa                     46

<210> SEQ ID NO 10
<211> LENGTH: 12
<212> TYPE: DNA
<213> ORGANISM: Homo sapiens

<400> SEQUENCE: 10
ggaggaggag ga                                                          12

<210> SEQ ID NO 11
<211> LENGTH: 38
<212> TYPE: DNA
<213> ORGANISM: Homo sapiens

<400> SEQUENCE: 11
agagaagagg ggaggaggag gaggagagga ggaggcgc                              38

<210> SEQ ID NO 12
<211> LENGTH: 13
<212> TYPE: DNA
<213> ORGANISM: Homo sapiens

<400> SEQUENCE: 12 ggaggggag ggg                                                          13
```

```
<210> SEQ ID NO 13
<211> LENGTH: 27
<212> TYPE: DNA
<213> ORGANISM: Homo sapiens

<400> SEQUENCE: 13
aggagaagga ggaggtggag gaggagg                                        27

<210> SEQ ID NO 14
<211> LENGTH: 33
<212> TYPE: DNA
<213> ORGANISM: Homo sapiens

<400> SEQUENCE: 14
aggaggagga gaatgcgagg aggagggagg aga                                 33

<210> SEQ ID NO 15
<211> LENGTH: 36
<212> TYPE: DNA
<213> ORGANISM: Homo sapiens

<400> SEQUENCE: 15
ggggcgggcc ggggcggggg tcccggcggg gcggag                              36

<210> SEQ ID NO 16
<211> LENGTH: 27
<212> TYPE: DNA
<213> ORGANISM: Homo sapiens

<400> SEQUENCE: 16
cgggaggagg aggaaggagg aagcgcg                                        27

<210> SEQ ID NO 17
<211> LENGTH: 45
<212> TYPE: DNA
<213> ORGANISM: Homo sapiens
<220> FEATURE:
<223> OTHER INFORMATION: Primer

<400> SEQUENCE: 17
agtctgactg actgtacgta gctaatacga ctcactatag caatt                    45

<210> SEQ ID NO 18
<211> LENGTH: 99
<212> TYPE: DNA
<213> ORGANISM: Homo sapiens
<220> FEATURE:
<223> OTHER INFORMATION: Primer

<400> SEQUENCE: 18
tccaactatg tatactgggg agggtgggga gggtgnggaa ggttagcgac acgcaattgc    60
tatagtgagt cgtattagct acgtacagtc agtcagact                           99

<210> SEQ ID NO 19
<211> LENGTH: 15
<212> TYPE: DNA
<213> ORGANISM: Homo sapiens

<400> SEQUENCE: 19
tccaactatg tatac                                                     15

<210> SEQ ID NO 20
<211> LENGTH: 35
```

```
<212> TYPE: DNA
<213> ORGANISM: Homo sapiens

<400> SEQUENCE: 20
ttagcgacac gcaattgcta tagtgagtcg tatta                                    35

<210> SEQ ID NO 21
<211> LENGTH: 80
<212> TYPE: DNA
<213> ORGANISM: Homo sapiens

<400> SEQUENCE: 21
tatacggggt gggggaggga gggattagcg acacgcaatt gctatagtga gtcgtattag         60
ctacgtacag tcagtcagac                                                     80

<210> SEQ ID NO 22
<211> LENGTH: 86
<212> TYPE: DNA
<213> ORGANISM: Homo sapiens

<400> SEQUENCE: 22
ttataccggg gcggggcggg ggcgggggct tagcgacacg caattgctat agtgagtcgt         60
attagctacg tacagtcagt cagact                                              86

<210> SEQ ID NO 23
<211> LENGTH: 97
<212> TYPE: DNA
<213> ORGANISM: Homo sapiens

<400> SEQUENCE: 23 tagggggcggg cgcgggagga aggggggcggg agcggggctg ttagcgacac gcaattgcta       60
tagtgagtcg tattagctac gtacagtcag tcagact                                  97

<210> SEQ ID NO 24
<211> LENGTH: 97
<212> TYPE: DNA
<213> ORGANISM: Homo sapiens

<400> SEQUENCE: 24
ttagagaaga ggggaggagg aggaggagag gaggaggcgc ttagcgacac gcaattgcta         60
tagtgagtcg tattagctac gtacagtcag tcagact                                  97

<210> SEQ ID NO 25
<211> LENGTH: 99
<212> TYPE: DNA
<213> ORGANISM: Homo sapiens

<400> SEQUENCE: 25
tccaactatg tatactgggg agggtgggga gggtgggggaa ggttagcgac acgcaattgc        60
tatagtgagt cgtattagct acgtacagtc agtcagact                                99

<210> SEQ ID NO 26
<211> LENGTH: 99
<212> TYPE: DNA
<213> ORGANISM: Homo sapiens

<400> SEQUENCE: 26
tccaactatg tatacccttc cccaccctcc ccaccctccc cattagcgac acgcaattgc         60
tatagtgagt cgtattagct acgtacagtc agtcagact                                99
```

```
<210> SEQ ID NO 27
<211> LENGTH: 95
<212> TYPE: DNA
<213> ORGANISM: Homo sapiens

<400> SEQUENCE: 27
tcatatatga ctacttaggg ttagggttag ggttagggtt actgccacgc aattgctata    60
gtgagtcgta ttagctacgt acagtcagtc agact                              95

<210> SEQ ID NO 28
<211> LENGTH: 89
<212> TYPE: DNA
<213> ORGANISM: Homo sapiens

<400> SEQUENCE: 28
atgatcaccg ggaggaggag gaaggaggaa gcgcgctgcc acgcaattgc tatagtgagt    60
cgtattagct acgtacagtc agtcagact                                     89

<210> SEQ ID NO 29
<211> LENGTH: 45
<212> TYPE: DNA
<213> ORGANISM: Homo sapiens
<220> FEATURE:
<223> OTHER INFORMATION: Primer

<400> SEQUENCE: 29
agtctgactg actgtacgta gctaatacga ctcactatag caatt                   45
```

QUINOBENZOXAZINE ANALOGS AND COMPOSITIONS

CROSS-REFERENCE TO RELATED APPLICATIONS

This application claims the benefit of U.S. provisional application Ser. No. 60/671,760, filed Apr. 15, 2005.

FIELD OF THE INVENTION

The invention relates to substituted quinobenzoxazines analogs, and methods of using such compounds.

BACKGROUND

Quadruplexes can form in certain purine-rich strands of nucleic acids. In duplex nucleic acids, certain purine rich strands are capable of engaging in a slow equilibrium between a typical duplex helix structure and in unwound and non-B-form regions. These unwound and non-B forms can be referred to as "paranemic structures." Some forms are associated with sensitivity to S1 nuclease digestion, which can be referred to as "nuclease hypersensitivity elements" or "NHEs." A quadruplex is one type of paranemic structure and certain NHEs can adopt a quadruplex structure. Considerable circumstantial evidence suggests that quadruplex structures can exist in vivo in specific regions of the genome, including the telomeric ends of chromosomes and oncogene regulatory regions. (Han, et al., *Trends Pharm. Sci.* (2000) 21:136-142). Thus, quadruplex forming regions of DNA may be used as molecular targets for anticancer agents.

SUMMARY OF THE INVENTION

In one aspect, the present invention provides a compound having formula 1

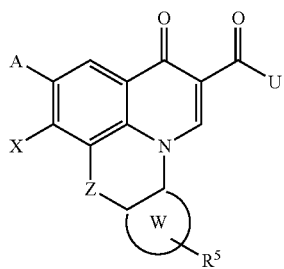

(1)

and pharmaceutically acceptable salts, esters and prodrugs thereof, wherein X is H, $OR^2$, $NR^1R^2$, halogen, azido, $SR^2$ or $CH_2R$;

A is H, halogen, $NR^1R^2$, $SR^2$, $OR^2$, $CH_2R^2$, azido or $NR^1$—$(CR^1{}_2)_n$—$NR^3R^4$;

Z is O, S, $NR^1$ or $CH_2$;

U is $R^2$, $OR^2$, $NR^1R^2$ or $NR^1$—$(CR^1{}_2)_n$—$NR^1R^4$ provided U is not H;

W is an optionally substituted aryl or heteroaryl, which may be monocyclic or fused with a single or multiple ring optionally containing a heteroatom;

wherein $R^1$ and $R^2$ together with N in $NR^1R^2$, and $R^3$ and $R^4$ together with N in $NR^3R^4$ may independently form an optionally substituted 5-6 membered ring containing N, and optionally O or S;

$R^1$ and $R^3$ are independently H or a $C_{1-6}$ alkyl; and $R^2$ and $R^4$ are independently H, or a $C_{1-10}$ alkyl or $C_{2-10}$ alkenyl optionally containing one or more non-adjacent heteroatoms selected from N, O, and S, and optionally substituted with a substituted or unsubstituted aryl, heteroaryl, carbocyclic, or heterocyclic ring; or $R^2$ is an optionally cycloalkyl, substituted heterocyclic ring, aryl or heteroaryl;

$R^5$ is a substituent at any position of W and is H, halo, cyano, azido, —$CONHR^1$, $OR^2$, or $C_{1-6}$ alkyl or $C_{2-6}$ alkenyl, each optionally substituted by halo, =O or one or more heteroatoms;

provided X and A both are not H, and further provided that $R^5$ is cyano or —$CONHR^1$ when A is H, halogen or $NR^1R^2$; or a compound having formula (1A)

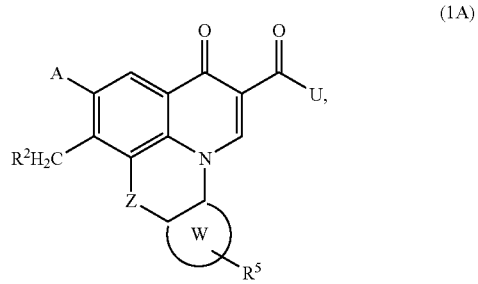

(1A)

and pharmaceutically acceptable salts, esters and prodrugs thereof;

A is H, halogen, azido, $SR^2$, $OR^2$, $CH_2R^2$, $NR^1R^2$, or $NR^1$—$(CR^1{}_2)_n$—$NR^3R^4$; Z, U, W, $R^1$, $R^2$, $R^3$ and $R^4$ are as defined in formula 1; and $R^5$ is a substituent at any position of W and is H, halo, cyano, azido, —$CONHR^1$, $OR^2$, or $C_{1-6}$ alkyl or $C_{2-6}$ alkenyl, each optionally substituted by halo, =O or one or more heteroatoms; wherein each optionally substituted moiety in formula 1 and 1A is substituted with one or more halo, cyano, azido, acetyl, amido, $OR^2$, $NR^1R^2$, carbamate, $C_{1-10}$ alkyl, $C_{2-10}$ alkenyl, each optionally substituted by halo, =O, aryl or one or more heteroatoms selected from N, O and S; or is substituted with an aryl, a carbocyclic or a heterocyclic ring.

In the above formula 1 or 1A, W may be selected from the group consisting of

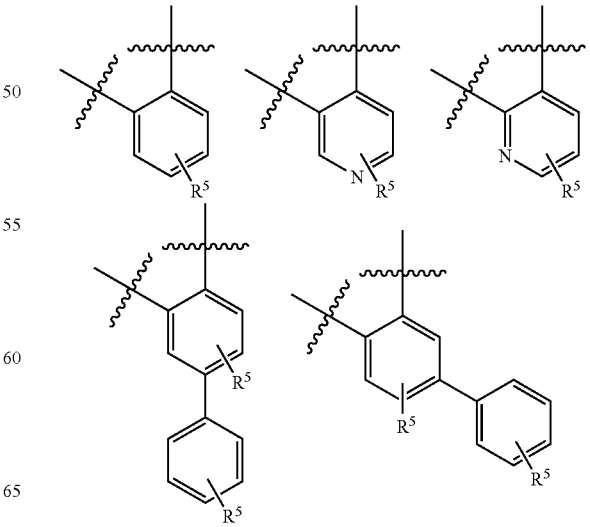

-continued
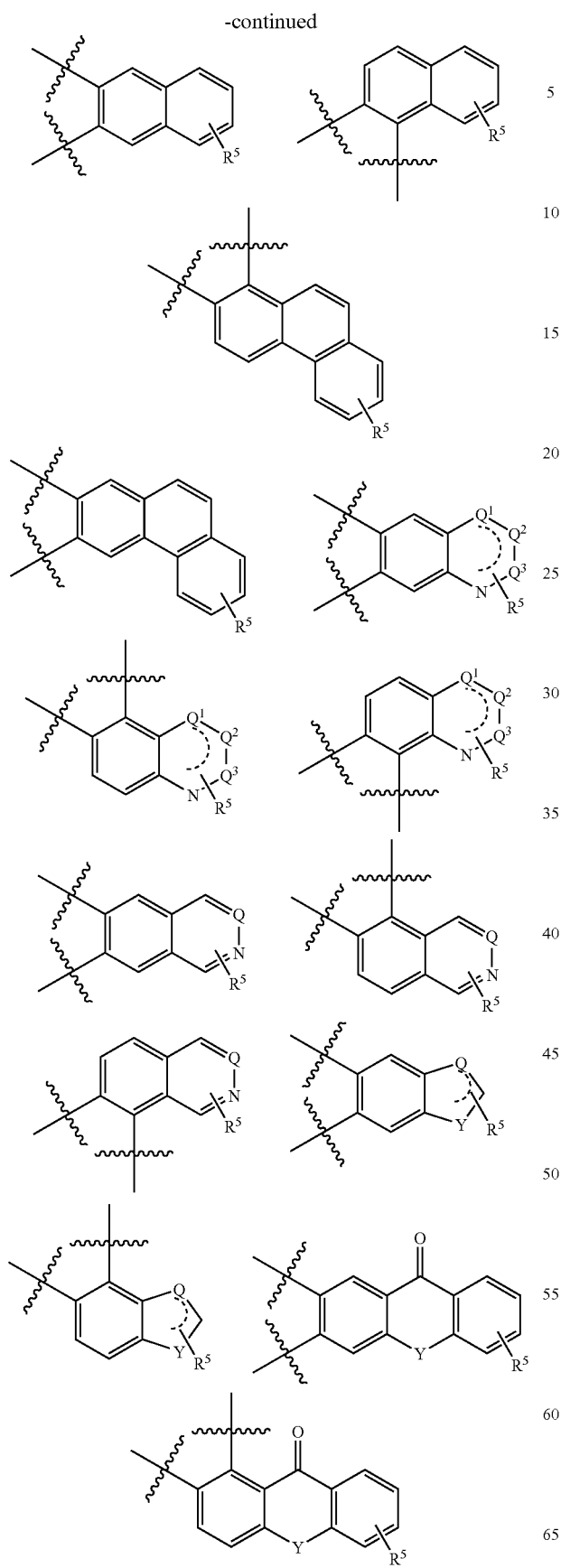
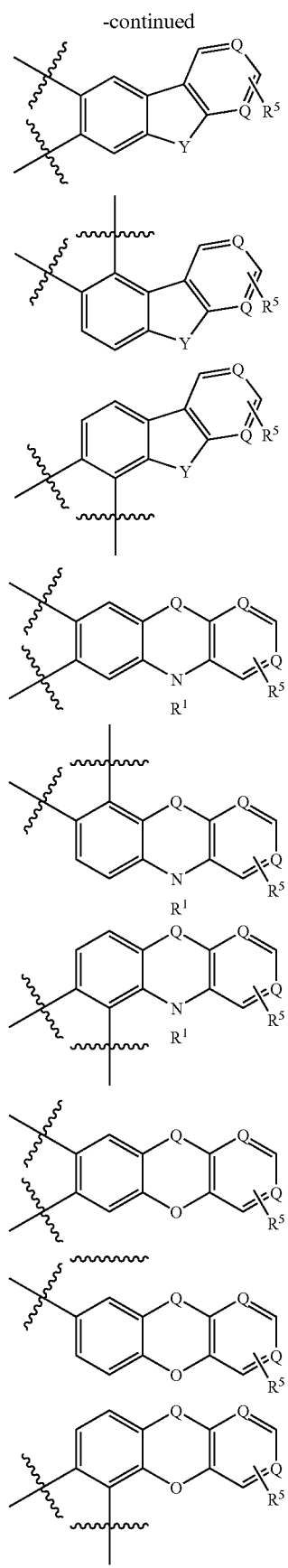

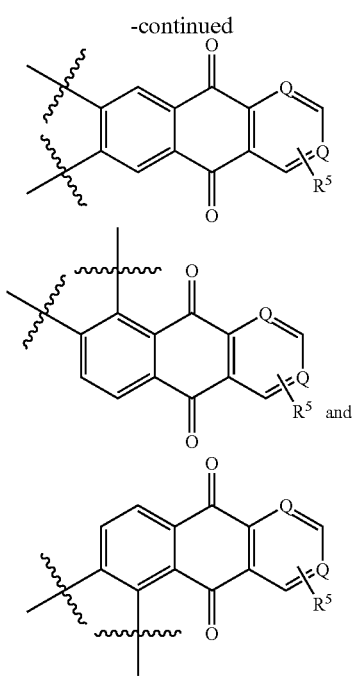

wherein Q, $Q^1$, $Q^2$, and $Q^3$ are independently CH or N;
Y is independently O, CH, =O or $NR^1$; and
$R^5$ is as defined in formula 1.

In some embodiments, each W in the above formula 1 or 1A may be an optionally substituted phenyl, pyridine, biphenyl, naphthalene, phenanthrene, quinoline, isoquinoline, quinazoline, cinnoline, phthalazine, quinoxaline, indole, benzimidazole, benzoxazole, benzthiazole, benzofuran, anthrone, xanthone, acridone, fluorenone, carbazolyl, pyrimido[4,3-b]furan, pyrido[4,3-b]indole, pyrido[2,3-b]indole, dibenzofuran, acridine or acridizine. In one embodiment, W is an optionally substituted phenyl.

In the above formula 1 or 1A, each Z may be O.

In one embodiment, A is $SR^2$ and X is H. In another embodiment, A is $NR^1$—$(CR^1{}_2)_n$—$NR^3R^4$, or an optionally substituted 5-14 membered heterocyclic ring containing N and optionally O or S. In some examples, A is an optionally substituted 5-14 membered heterocyclic ring and X is H or halogen.

Examples of 5-14 membered heterocyclic rings include but are not limited to tetrahydrofuran, 1,3-dioxolane, 2,3-dihydrofuran, tetrahydropyran, benzofuran, isobenzofuran, 1,3-dihydro-isobenzofuran, isoxazole, 4,5-dihydroisoxazole, piperidine, piperidin-2-one, pyrrolidine, pyrrolidin-2-one, pyrrole, pyridine, pyrimidine, octahydro-pyrrolo[3,4-b]pyridine, piperazine, piperazin-2-one, pyrazine, morpholine, thiomorpholine, imidazole, imidazolidine-2,4-dione, benzimidazole, 1,3-dihydrobenzimidazol-2-one, indole, thiazole, benzothiazole, thiadiazole, thiophene, tetrahydro-thiophene 1,1-dioxide, diazepine, triazole, guanidine, diazabicyclo[2.2.1]heptane, 2,5-diazabicyclo[2.2.1]heptane, or 2,3,4,4a,9,9a-hexahydro-1H-β-carboline. In particular examples, A is an optionally substituted morpholine, thiomorpholine, imidazole, pyrrolidine, pyrrolidin-2-one, piperazine, piperazin-2-one, pyridine, piperidine, or piperidin-2-one.

In another embodiment, U in formula 1 is $NR^1$—$(CR^1{}_2)_n$—$NR^3R^4$. In some examples, n is 2-3. In other examples, $R^3$ and $R^4$ together with N form an optionally substituted ring containing N, and optionally O or S. In particular examples, the $NR^3R^4$ moiety is an optionally substituted morpholine, thiomorpholine, imidazole, pyrrolidine, piperazine, pyridine or piperidine.

In yet another embodiment, W is phenyl; and X is H. In these embodiments, A may an optionally substituted morpholine, thiomorpholine, imidazole, pyrrolidine, pyrrolidin-2-one, piperazine, piperazin-2-one, pyridine, piperidine, or piperidin-2-one. In some examples, A is an optionally substituted piperazine. In some of these embodiments, U may be $NR^1$—$(CR^2)_n$—$NR^3R^4$, and in some examples, the $NR^3R^4$ moiety is morpholine, thiomorpholine, imidazole, pyrrolidine, piperazine, pyridine or piperidine.

In another aspect, the present invention provides a compound having formula 2

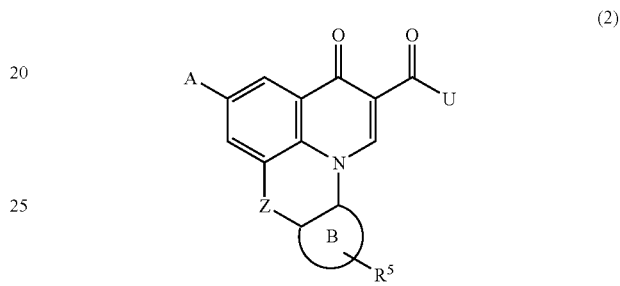

(2)

and pharmaceutically acceptable salts, esters and prodrugs thereof; wherein A is $NR^1R^2$;
Z is O, S, $NR^1$ or $CH_2$; and
U is $NR^1R^2$ or $NR^1$—$(CR^1{}_2)_n$—$NR^3R^4$
B is a 5-6 membered aryl or heteroaryl;
$R^1$ and $R^2$ together with N in $NR^1R^2$, and $R^3$ and $R^4$ together with N in $NR^3R^4$ may independently form an optionally substituted 5-6 membered ring containing N, and optionally O or S;
$R^1$ and $R^3$ are independently H or a $C_{1-6}$ alkyl; and
$R^2$ and $R^4$ are independently H, or a $C_{1-10}$ alkyl or $C_{2-10}$ alkenyl optionally containing one or more non-adjacent heteroatoms selected from N, O, and S, and optionally substituted with a substituted or unsubstituted aryl, heteroaryl, carbocyclic, or heterocyclic ring; or $R^2$ is an optionally substituted cycloalkyl, heterocyclic ring, aryl or heteroaryl;
$R^5$ is a substituent at any position of W and is H, halo, cyano, azido, —$CONHR^1$, $OR^1$, or $C_{1-6}$ alkyl or $C_{2-6}$ alkenyl, each optionally substituted by halo, =O or one or more heteroatoms;
wherein each optionally substituted moiety is substituted with one or more halo, cyano, azido, acetyl, amido, $OR^2$, $NR^1R^2$, carbamate, $C_{1-10}$ alkyl, $C_{2-10}$ alkenyl, each optionally substituted by halo, =O, aryl or one or more heteroatoms selected from N, O and S; or is substituted with an aryl, a carbocyclic or a heterocyclic ring.

In the above formula 2, W may be phenyl. In some embodiments, Z is O. In other embodiments, $R^5$ is halo.

In the above formula 2, the $NR^1R^2$ and $NR^3R^4$ moieties may independently be an optionally substituted morpholine, thiomorpholine, imidazole, pyrrolidine, piperazine, pyridine or piperidine.

In another aspect, the present invention provides a compound having formula 3

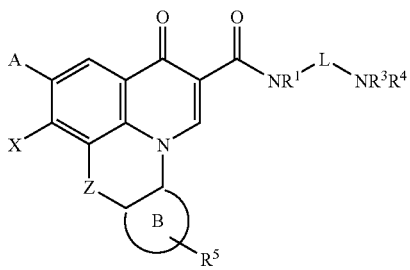

and pharmaceutically acceptable salts, esters and prodrugs thereof;

wherein A is H or F;

X is H, halo or $NR^1R^2$;

Z is O, S, $NR^1$ or $CH_2$;

L is a $C_{1-10}$ alkyl optionally substituted with N, O or S;

B is 5-6 membered aryl or heteroaryl;

$R^1$ and $R^3$ are independently H or a $C_{1-6}$ alkyl;

$R^2$ and $R^4$ is H, or a $C_{1-10}$ alkyl or $C_{2-10}$ alkenyl optionally containing one or more non-adjacent heteroatoms selected from N, O, and S, and optionally substituted with a substituted or unsubstituted aryl, heteroaryl, carbocyclic, or heterocyclic ring; or $R^2$ is an optionally substituted cycloalkyl, heterocyclic ring, aryl or heteroaryl;

$R^5$ is a substituent at any position of W and is H, halo, cyano, $—CONHR^1$, $OR^2$, or $C_{1-6}$ alkyl or $C_{2-6}$ alkenyl, each optionally substituted by halo, $=O$ or one or more heteroatoms;

wherein each optionally substituted moiety is substituted with one or more halo, cyano, azido, acetyl, amido, $OR^2$, $NR^1R^2$, carbamate, $C_{1-10}$ alkyl, $C_{2-10}$ alkenyl, each optionally substituted by halo, $=O$, aryl or one or more heteroatoms selected from N, O and S; or is substituted with an aryl, a carbocyclic or a heterocyclic ring;

provided said compound is not

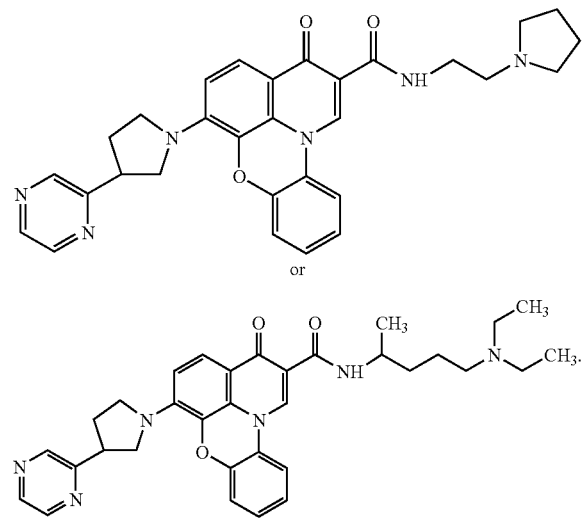

In the above formula 3, W may be phenyl or pyridyl. In some embodiments, L is a $C_{2-4}$ alkyl.

In the above formula 3, X may be $NR^1R^2$, and $R^2$ is an optionally substituted cyclopropyl, pheny, or imidazole, or a $C_{1-6}$ alkyl optionally substituted with a cyclopropyl or $OR^1$.

In some embodiments, the $NR^1R^2$ and $NR^3R^4$ moieties in formula 3 are independently an optionally substituted morpholine, thiomorpholine, imidazole, pyrrolidine, piperazine, pyridine or piperidine.

In yet other embodiments, A in formula 3 is F and $R^5$ is halo, cyano, amido or azido.

The present invention also provides pharmaceutical compositions comprising a compound having formula 1, 1A, 2 or 3, and a pharmaceutically acceptable excipient.

Furthermore, the present invention relates to methods for ameliorating a cell proliferative disorder, comprising administering to a subject in need thereof an effective amount of a compound having formula 1, 1A, 2 or 3, or a pharmaceutical composition thereof and optionally with a chemotherapeutic agent, thereby ameliorating said cell-proliferative disorder. For example, cell proliferation may be reduced, or cell death may be induced. The cell proliferative disorder may be a tumor or a cancer. The subject may be human or an animal.

The present invention also relates to methods for reducing cell proliferation or inducing cell death, comprising contacting a system with an effective amount of a compound having formula 1, 1A, 2 or 3, or a pharmaceutical composition thereof and optionally with a chemotherapeutic agent, thereby reducing cell proliferation or inducing cell death in said system. The system may be a cell or a tissue.

Furthermore, the present invention provides methods for reducing microbial titers, comprising contacting a system with an effective amount of a compound having formula 1, 1A, 2 or 3, or a pharmaceutical composition thereof and optionally with an antimicrobial agent, thereby reducing microbial titers. The system may be a cell or a tissue.

The present invention also provides methods for ameliorating a microbial infection, comprising administering to a subject in need thereof an effective amount of a compound having formula 1, 1A, 2 or 3, or a pharmaceutical composition thereof and optionally with an antimicrobial agent, thereby ameliorating said microbial infection. The subject may be human or an animal. The microbial titers may be viral, bacterial or fungal titers.

The present invention also provides methods for inducing apoptosis, comprising administering to a system or a subject in need thereof an effective amount of a compound having formula 1, 1A, 2 or 3, or a pharmaceutical composition thereof and optionally with a chemotherapeutic agent.

The present invention also provides methods for treating or ameliorating a disorder mediated by c-Myc overexpression, comprising administering to a system or a subject in need thereof an effective amount of a compound having formula 1, 1A, 2 or 3, or a pharmaceutical composition thereof and optionally with a chemotherapeutic agent. The subject may be human or an animal, and system may be a cell or a tissue.

The present invention also relates to methods for determining interaction selectivity between a compound having formula 1, 1A, 2 or 3, and nucleic acids capable of forming a quadruplex structure, comprising: a) contacting a compound in the absence of a competitor molecule with three or more nucleic acids capable of forming a quadruplex structure, wherein each nucleic acid is not a telomere nucleic acid; b) measuring a direct interaction between the compound and said three or more nucleic acids; and c) determining interaction selectivity from a comparison of the interaction measurements. In one example, three or more nucleic acids comprise a nucleotide sequence located 5' of an oncogene nucleotide sequence. The oncogene may be MYC, HIF, VEGF, ABL, TGF, PDGFα, MYB, SPARC, HER, VAV, RET, H-RAS, EGF, SRC, BCL-1, BCL-2, DHFR, or HMGA.

In the above methods for determining interaction selectivity, the compound may be separately contacted with each of said three or more nucleic acids in a different vessel. Furthermore, the interaction selectivity may be determined from a comparison of $IC_{50}$ values.

In the above methods, the compound may bind and/or stabilize a propeller quadruplex. Examples of propeller quadruplexes include but are not limited to H-RAS, RET, BCL-1, DHFR, TGF-β, HIF-1α, VEGF, c-Myc, or PDGFα. In another embodiment, the compound may bind and/or stabilize a chair-eller or a basket quadruplex. For example, the compound may bind and/or stabilize BCL-2.

Definitions

As used herein, the term "alkyl" refers to a carbon-containing compound, and encompasses compounds containing one or more heteroatoms. The term "alkyl" also encompasses alkyls substituted with one or more substituents including but not limited to $OR^1$, amino, amido, halo, =O, aryl, heterocyclic groups, or inorganic substituents.

As used herein, the term "carbocycle" refers to a cyclic compound containing only carbon atoms in the ring, whereas a "heterocycle" refers to a cyclic compound comprising a heteroatom. The carbocyclic and heterocyclic structures encompass compounds having monocyclic, bicyclic or multiple ring systems.

As used herein, the term "aryl" refers to a polyunsaturated, typically aromatic hydrocarbon substituent, whereas a "heteroaryl" or "heteroaromatic" refer to an aromatic ring containing a heteroatom. The aryl and heteroaryl structures encompass compounds having monocyclic, bicyclic or multiple ring systems.

As used herein, the term "heteroatom" refers to any atom that is not carbon or hydrogen, such as nitrogen, oxygen or sulfur.

Illustrative examples of heterocycles include but are not limited to tetrahydrofuran, 1,3-dioxolane, 2,3-dihydrofuran, pyran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4-b]pyridine, piperazine, pyrazine, morpholine, thiomorpholine, imidazole, imidazolidine-2,4-dione, 1,3-dihydrobenzimidazol-2-one, indole, thiazole, benzothiazole, thiadiazole, thiophene, tetrahydrothiophene 1,1-dioxide, diazepine, triazole, guanidine, diazabicyclo[2.2.1]heptane, 2,5-diazabicyclo[2.2.1]heptane, 2,3,4,4a,9,9a-hexahydro-1H-β-carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

The terms "treat," "treatment" and "therapeutic effect" as used herein refer to reducing or stopping a cell proliferation rate (e.g., slowing or halting tumor growth) or reducing the number of proliferating cancer cells (e.g., removing part or all of a tumor). These terms also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

As used herein, the term "chemotherapeutic agent" refers to a therapeutic agent that may be used for treating or ameliorating a cell proliferative disorder such as tumors or cancer. Examples of chemotherapeutic agents include but are not limited to an antineoplastic agent, an alkylating agent, a plant alkaloid, an antimicrobial agent, a sulfonamide, an antiviral agent, a platinum agent, and other anticancer agents known in the art. Particular examples of chemotherapeutic agents include but are not limited to cisplatin, carboplatin, busulphan, methotrexate, daunorubicin, doxorubicin, cyclophosphamide, mephalan, vincristine, vinblastine, chlorambucil, paclitaxel, gemcitabine, and others known in the art. (See e.g., Goodman & Gilman's, *The Pharmacological Basis of Therapeutics* (9th Ed) (Goodman, et al., eds.) (McGraw-Hill) (1996); and 1999 *Physician's Desk Reference* (1998)).

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

DESCRIPTION OF THE INVENTION

The present invention relates to compounds having formula 1, 1A, 2 and 3, and pharmaceutically acceptable salts, esters, and prodrugs thereof. The present invention also relates to methods for using the compounds described herein, such as in screening. The compounds may interact with regions of DNA that can form quadruplexes, and may also be used for treatment of cell proliferative disorders.

In one aspect, the present invention provides a compound having formula 1

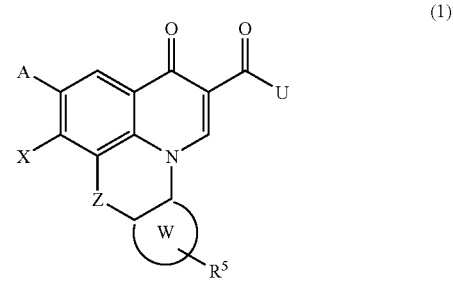

(1)

and pharmaceutically acceptable salts, esters and prodrugs thereof, wherein X is H, $OR^2$, $NR^1R^2$, halogen, azido, $SR^2$ or $CH_2R$;

A is H, halogen, $NR^1R^2$, $SR^2$, $OR^2$, $CH_2R^2$, azido or $NR^1$—$(CR^1{}_2)_n$—$NR^3R^4$;

Z is O, S, $NR^1$ or $CH_2$;

U is $R^2$, $OR^2$, $NR^1R^2$ or $NR^1$—$(CR^1{}_2)_n$—$NR^3R^4$ provided U is not H;

W is an optionally substituted aryl or heteroaryl, which may be monocyclic or fused with a single or multiple ring optionally containing a heteroatom;

wherein $R^1$ and $R^2$ together with N in $NR^1R^2$, and $R^3$ and $R^4$ together with N in $NR^3R^4$ may independently form an optionally substituted 5-6 membered ring containing N, and optionally O or S;

$R^1$ and $R^3$ are independently H or a $C_{1-6}$ alkyl; and $R^2$ and $R^4$ are independently H, or a $C_{1-10}$ alkyl or $C_{2-10}$ alkenyl optionally containing one or more non-adjacent heteroatoms selected from N, O, and S, and optionally substituted with a substituted or unsubstituted aryl, heteroaryl, carbocyclic, or heterocyclic ring; or $R^2$ is an optionally cycloalkyl, substituted heterocyclic ring, aryl or heteroaryl;

$R^5$ is a substituent at any position of W and is H, halo, cyano, azido, —$CONHR^1$, $OR^2$, or $C_{1-6}$ alkyl or $C_{2-6}$ alkenyl, each optionally substituted by halo, =O or one or more heteroatoms;

provided X and A both are not H, and further provided that $R^5$ is cyano or —$CONHR^1$ when A is H, halogen or $NR^1R^2$;

or a compound having formula (1A)

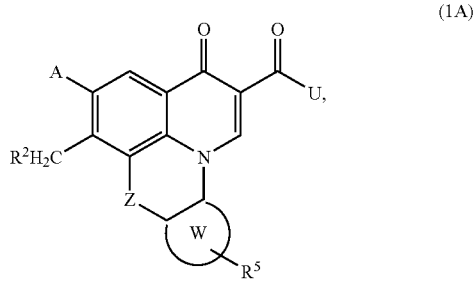

(1A)

and pharmaceutically acceptable salts, esters and prodrugs thereof;

A is H, halogen, azido, $SR^2$, $OR^2$, $CH_2R^2$, $NR^1R^2$, or $NR^1$—$(CR^1_2)_n$—$NR^3R^4$;

Z, U, W, $R^1$, $R^2$, $R^3$ and $R^4$ are as defined in formula 1; and $R^5$ is a substituent at any position of W and is H, halo, cyano, azido, —$CONHR^1$, $OR^2$, or $C_{1-6}$ alkyl or $C_{2-6}$ alkenyl, each optionally substituted by halo, =O or one or more heteroatoms;

wherein each optionally substituted moiety in formula 1 and 1A is substituted with one or more halo, cyano, azido, acetyl, amido, $OR^2$, $NR^1R^2$, carbamate, $C_{1-10}$ alkyl, $C_{2-10}$ alkenyl, each optionally substituted by halo, =O, aryl or one or more heteroatoms selected from N, O and S; or is substituted with an aryl, a carbocyclic or a heterocyclic ring.

Illustrative examples of compounds having formula 1 are shown in Table 1A (where $R_5$ is cyano and amido), Table 1B (where A is $SR^2$) and Table 1C (A is $NR^1R^2$).

TABLE 1A

| | STOP IC50μM | HCT-116 MTS μM | Hela MTS μM |
|---|---|---|---|
| | 6.1 | 3.6 | 11 |
| | 6.8 | 0.4 | 1.2 |

TABLE 1A-continued
| | STOP IC50 μM | HCT-116 MTS μM | Hela MTS μM |
|---|---|---|---|
| 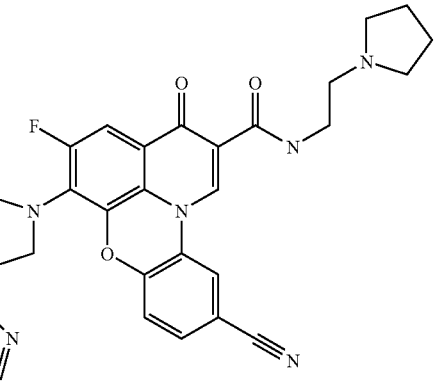 | 5 | 0.031 | 0.21 |
| 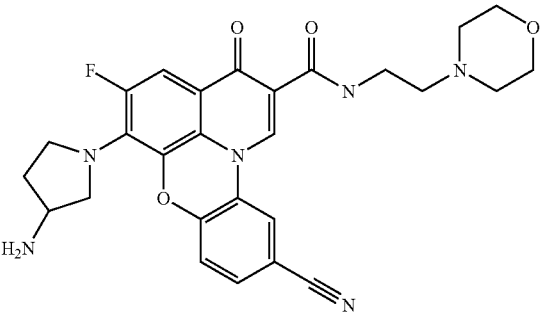 | 5.3 | 0.4 | 0.68 |
| 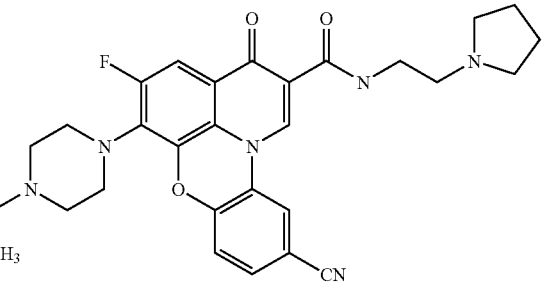 | 10 | 0.03 | 0.04 |

TABLE 1B

| | STOP IC50 μM | HCT-116 MTS μM | Hela MTS μM |
|---|---|---|---|
| *(structure 1)* | 3.9 | 2.8 | 0.28 |
| *(structure 2)* | 3.4 | 10 | 1.8 |
| *(structure 3)* | 14 | 3.9 | 5.2 |

TABLE 1B-continued
| | STOP IC50 μM | HCT-116 MTS μM | Hela MTS μM |
|---|---|---|---|
| 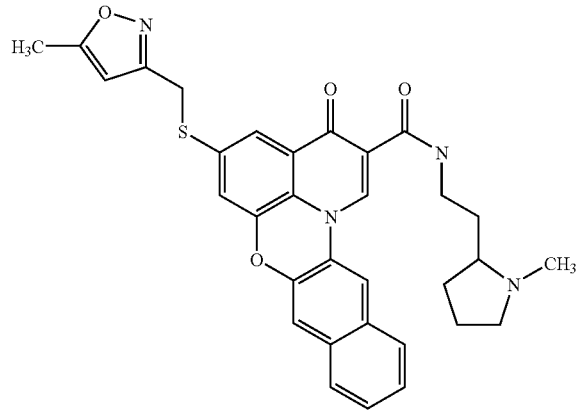 | 5.4 | 2.9 | 2.3 |
| 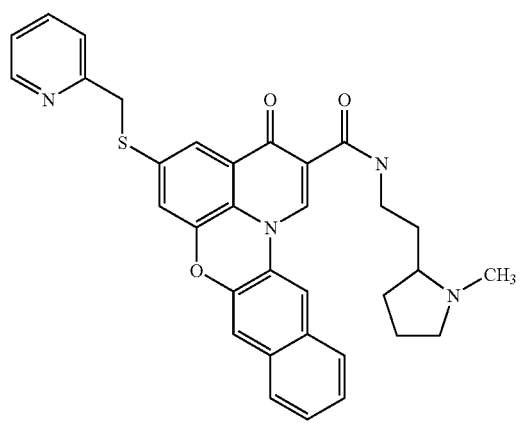 | 3.8 | 3.1 | 2.5 |
| 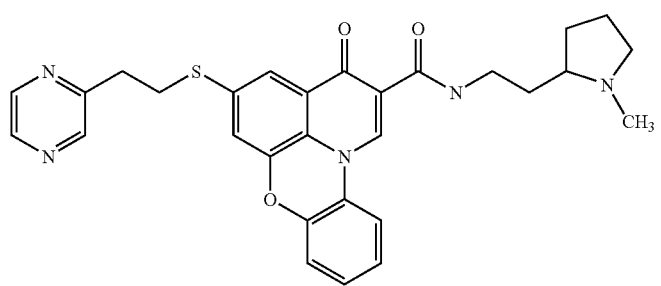 | 10 | 3.8 | 3 |

TABLE 1B-continued

| | STOP IC50 μM | HCT-116 MTS μM | Hela MTS μM |
|---|---|---|---|
| [structure] | 2.9 | 4.2 | 4.1 |

TABLE 1C

| | STOP IC50 μM | HCT-116 MTS μM | Hela MTS μM |
|---|---|---|---|
| [structure] | 6 | | |
| [structure] | | | |

TABLE 1C-continued

| | STOP IC50μM | HCT-116 MTS μM | Hela MTS μM |
|---|---|---|---|

[Structures shown]

In another aspect, the invention provides a compound having formula (2)

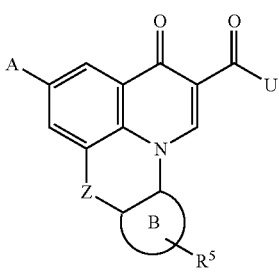

(2)

and pharmaceutically acceptable salts, esters and prodrugs thereof;

wherein A is $NR^1R^2$;

Z is O, S, $NR^1$ or $CH_2$; and

U is $NR^1R^2$ or $NR^1$—$(CR^1{}_2)_n$—$NR^3R^4$;

B is a 5-6 membered aryl or heteroaryl;

$R^1$ and $R^2$ together with N in $NR^1R^2$, and $R^3$ and $R^4$ together with N in $NR^3R^4$ may independently form an optionally substituted 5-6 membered ring containing N, and optionally O or S;

$R^1$ and $R^3$ are independently H or a $C_{1-6}$ alkyl; and $R^2$ and $R^4$ are independently H, or a $C_{1-10}$ alkyl or $C_{2-10}$ alkenyl optionally containing one or more non-adjacent heteroatoms selected from N, O, and S, and optionally substituted with a substituted or unsubstituted aryl, heteroaryl, carbocyclic, or heterocyclic ring; or $R^2$ is an optionally substituted cycloalkyl, heterocyclic ring, aryl or heteroaryl;

$R^5$ is a substituent at any position of W and is H, halo, cyano, azido, —$CONHR^1$, $OR^2$, or $C_{1-6}$ alkyl or $C_{2-6}$ alkenyl, each optionally substituted by halo, =O or one or more heteroatoms;

wherein each optionally substituted moiety is substituted with one or more halo, cyano, azido, acetyl, amido, $OR^2$, $NR^1R^2$, carbamate, $C_{1-10}$ alkyl, $C_{2-10}$ alkenyl, each optionally substituted by halo, =O, aryl or one or more heteroatoms selected from N, O and S; or is substituted with an aryl, a carbocyclic or a heterocyclic ring.

In another aspect, the invention provides compounds having formula (3)

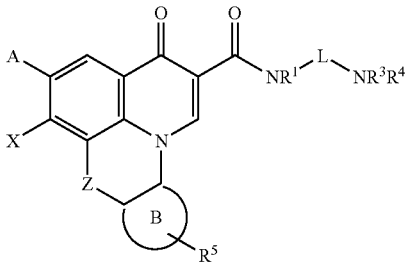

(3)

and pharmaceutically acceptable salts, esters and prodrugs thereof;

wherein A is H or F;

X is H, halo or $NR^1R^2$;

Z is O, S, NR¹ or CH₂;

L is a $C_{1-10}$ alkyl optionally substituted with N, O or S;

B is 5-6 membered aryl or heteroaryl;

$R^1$ and $R^3$ are independently H or a $C_{1-6}$ alkyl;

$R^2$ and $R^4$ is H, or a $C_{1-10}$ alkyl or $C_{2-10}$ alkenyl optionally containing one or more non-adjacent heteroatoms selected from N, O, and S, and optionally substituted with a substituted or unsubstituted aryl, heteroaryl, carbocyclic, or heterocyclic ring; or $R^2$ is an optionally substituted cycloalkyl, heterocyclic ring, aryl or heteroaryl;

$R^5$ is a substituent at any position of W and is H, halo, cyano, —CONHR¹, OR¹, or $C_{1-6}$ alkyl or $C_{2-6}$ alkenyl, each optionally substituted by halo, =O or one or more heteroatoms;

wherein each optionally substituted moiety is substituted with one or more halo, cyano, azido, acetyl, amido, $OR^2$, $NR^1R^2$, carbamate, $C_{1-10}$ alkyl, $C_{2-10}$ alkenyl, each optionally substituted by halo, =O, aryl or one or more heteroatoms selected from N, O and S; or is substituted with an aryl, a carbocyclic or a heterocyclic ring; provided said compound is not

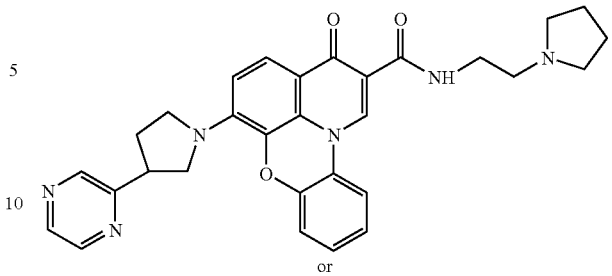

or

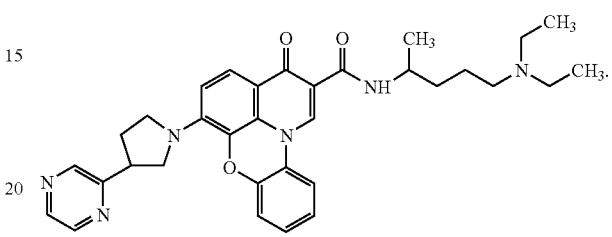

Illustrative examples of compounds having formula 2 and 3 are shown in Tables 1D-1F.

TABLE 1D

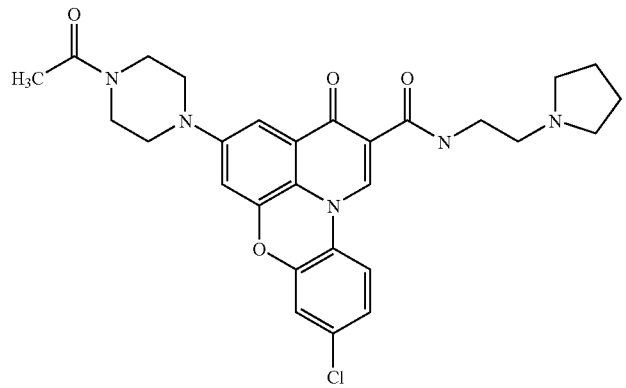

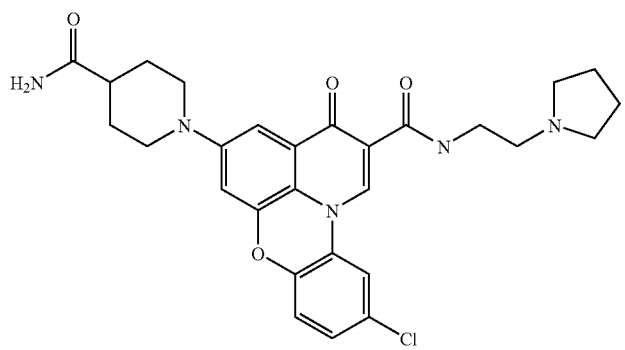

TABLE 1D-continued
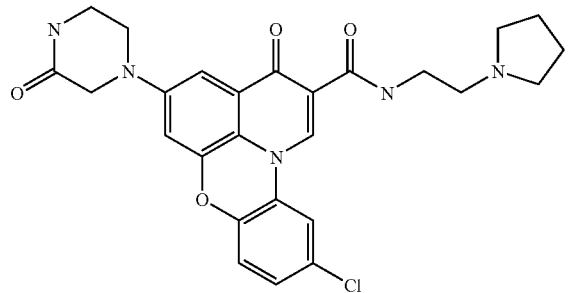
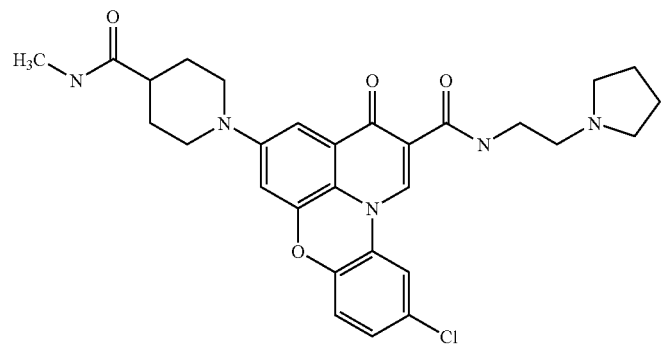
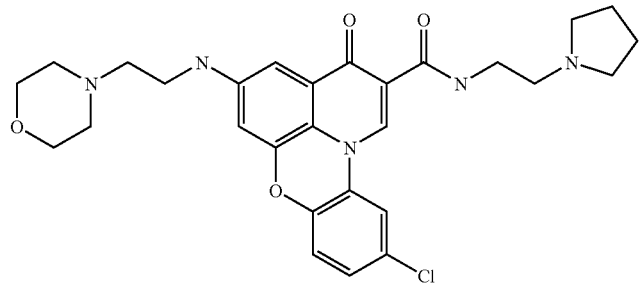
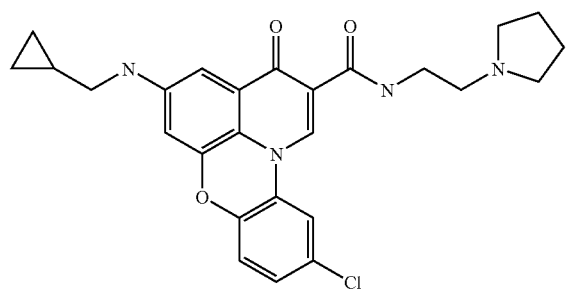
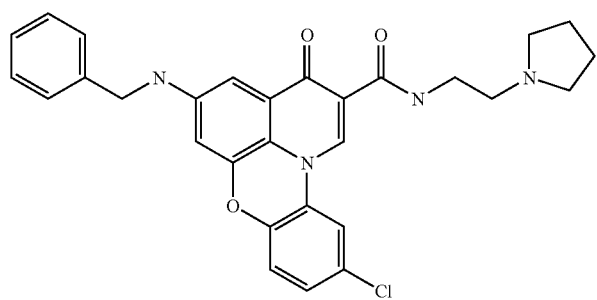

TABLE 1D-continued
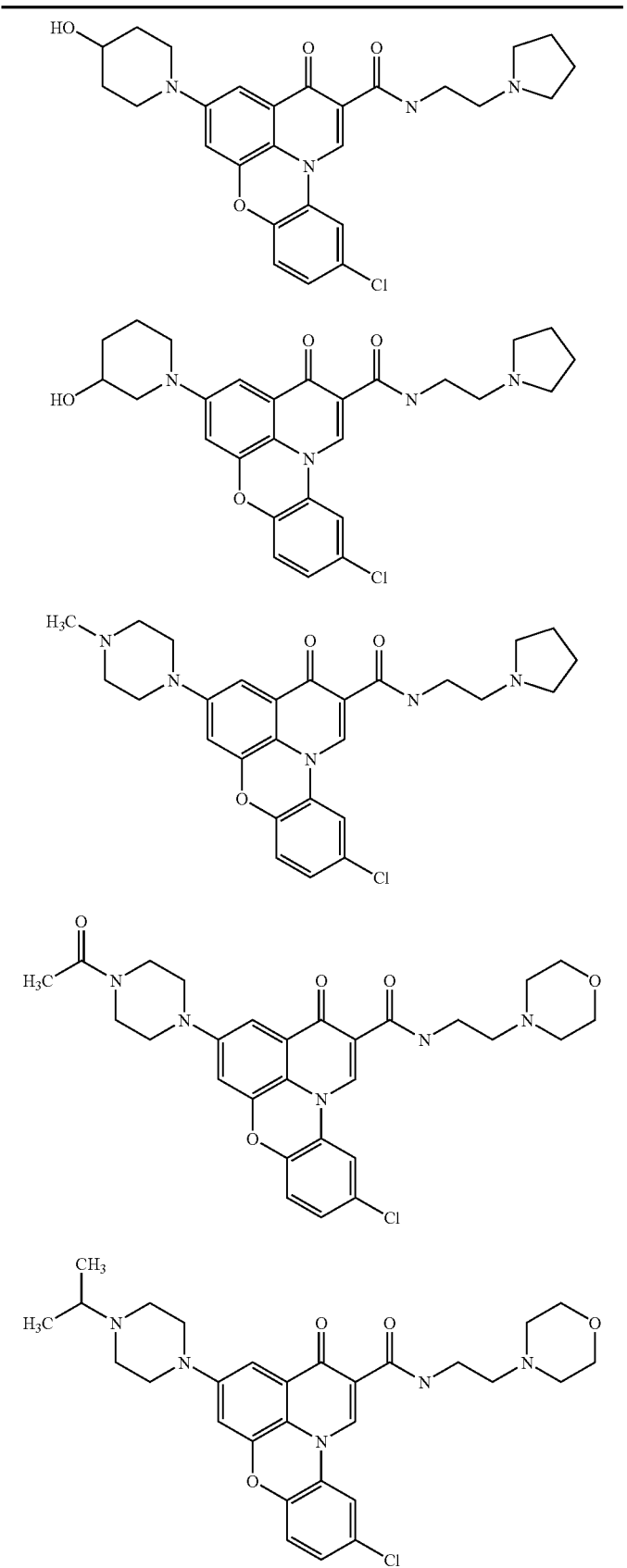

TABLE 1D-continued
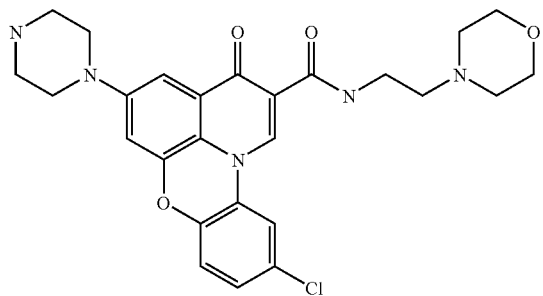
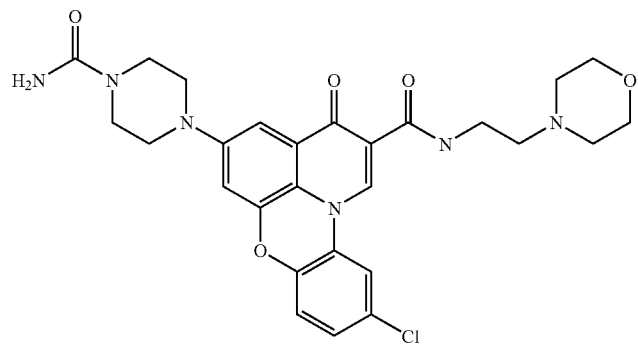
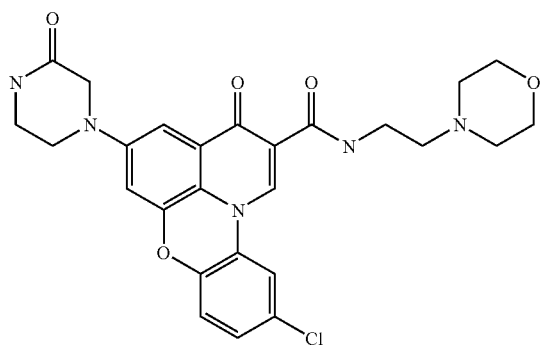
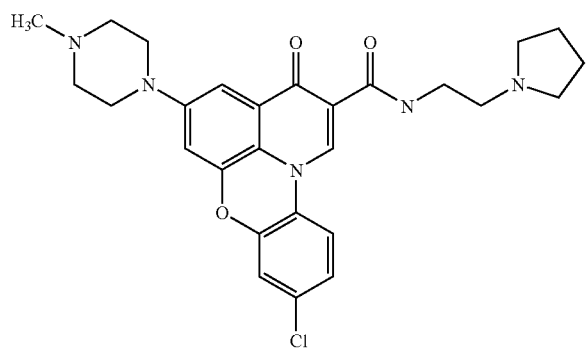

TABLE 1D-continued
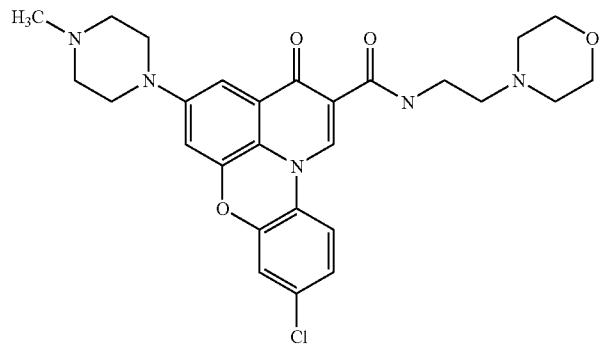
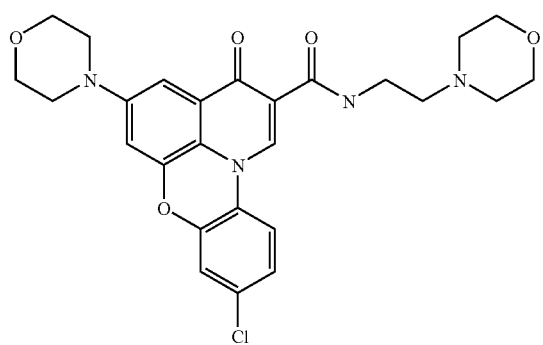
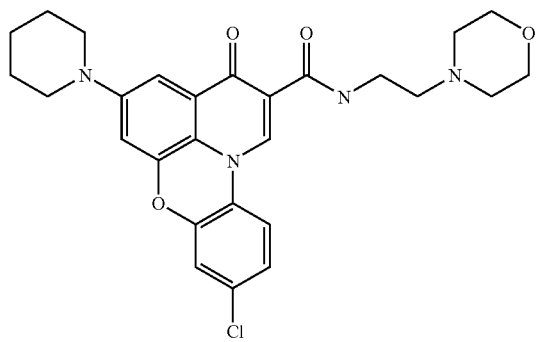
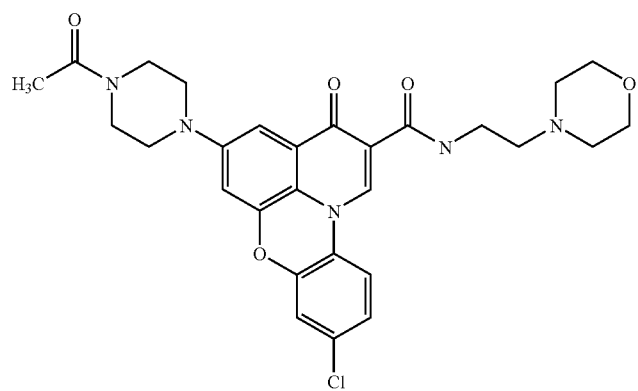

TABLE 1D-continued
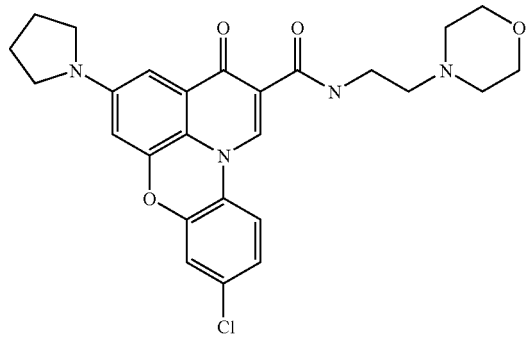
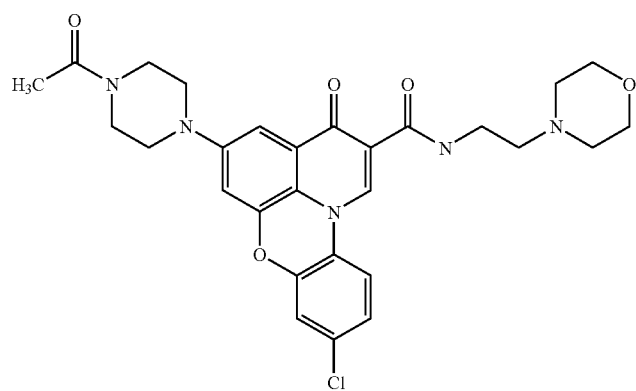
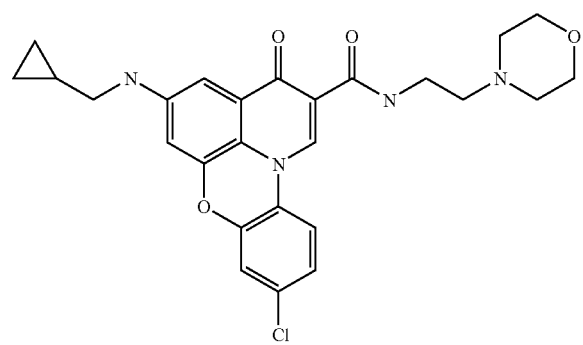
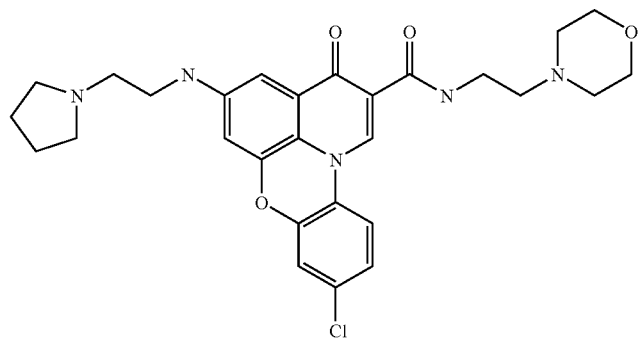

TABLE 1D-continued
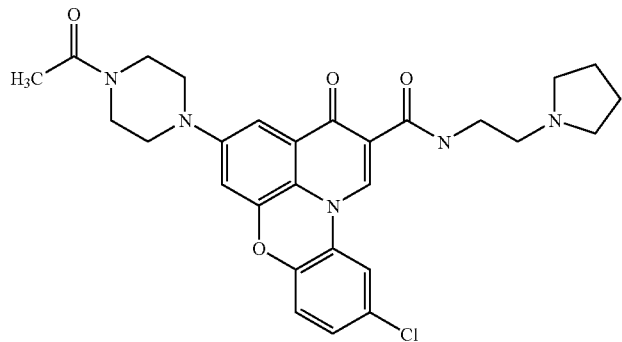
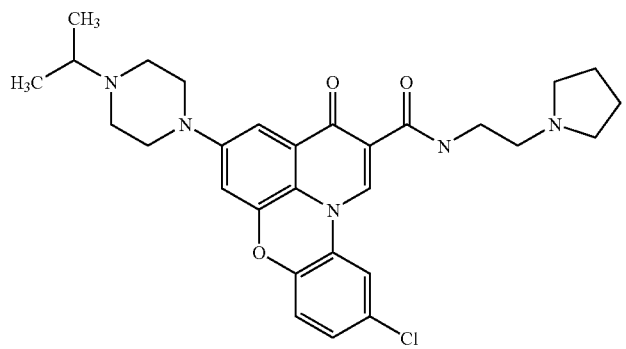
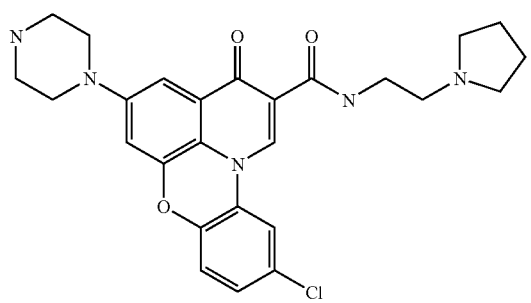
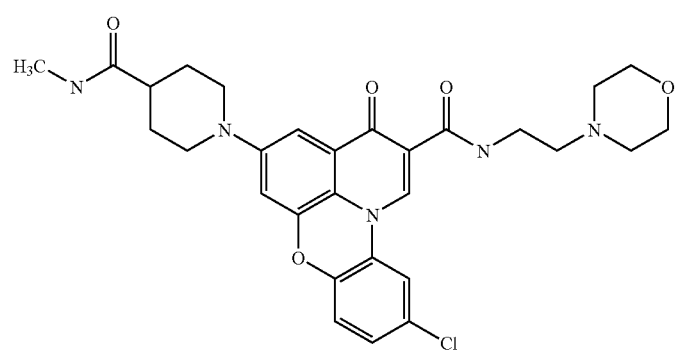

TABLE 1D-continued
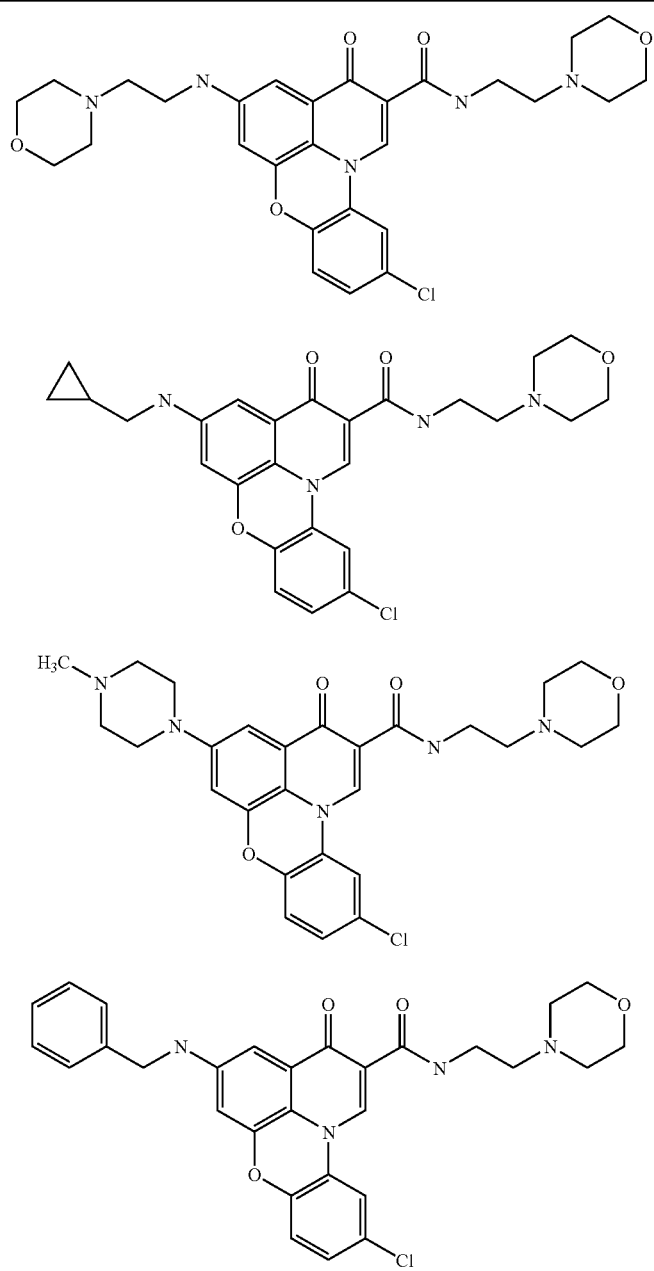
TABLE 1E
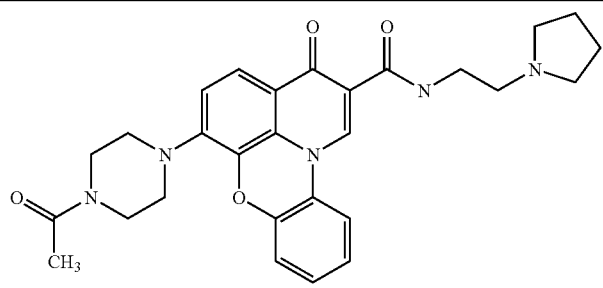

TABLE 1E-continued
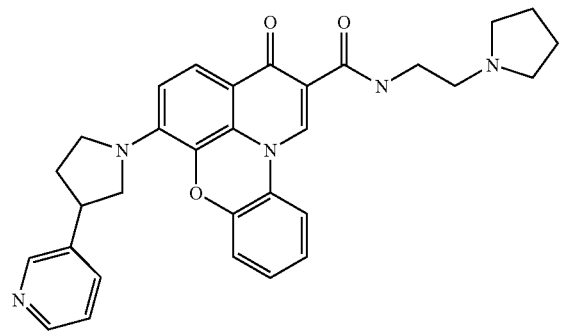
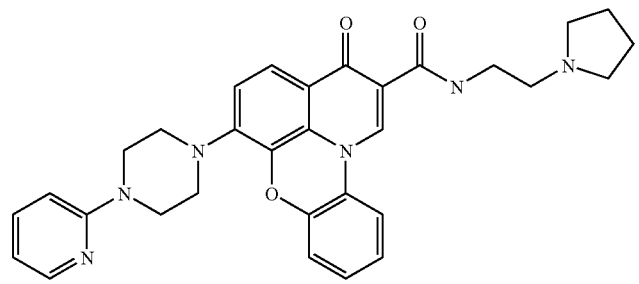
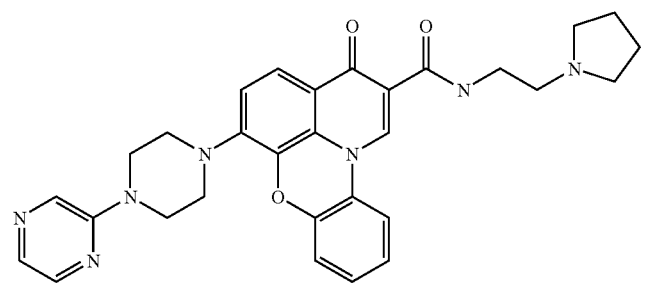
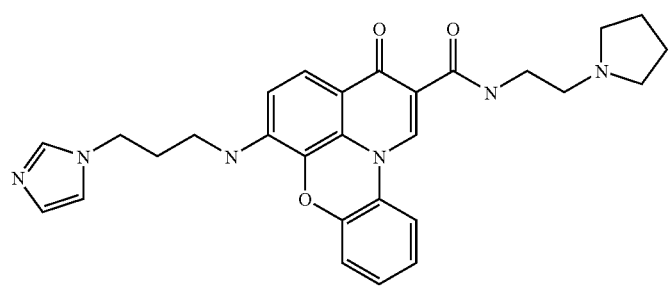
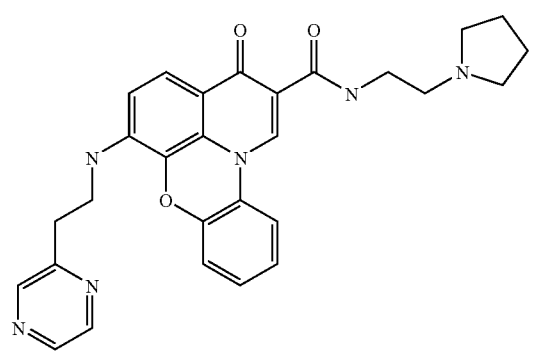

TABLE 1E-continued
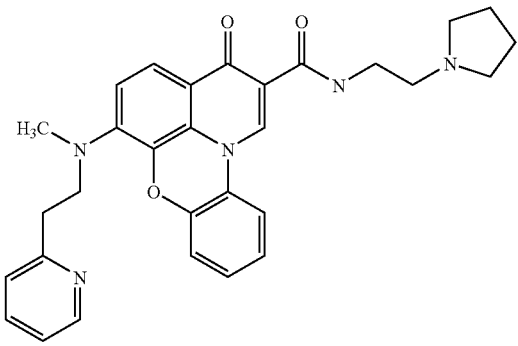
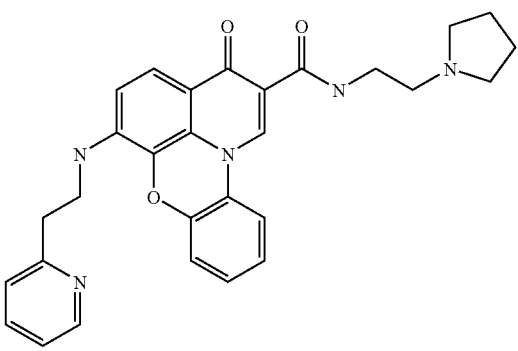
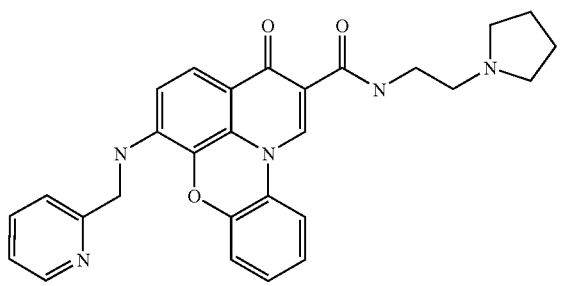
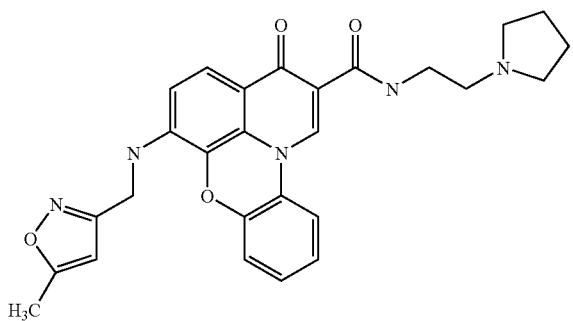

TABLE 1E-continued
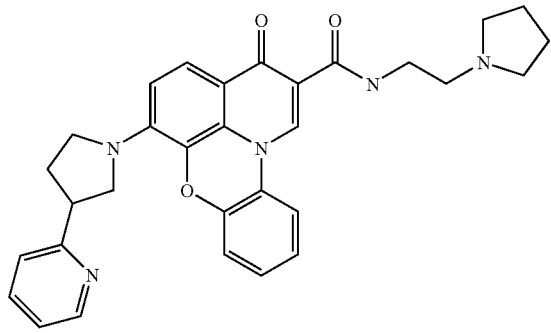
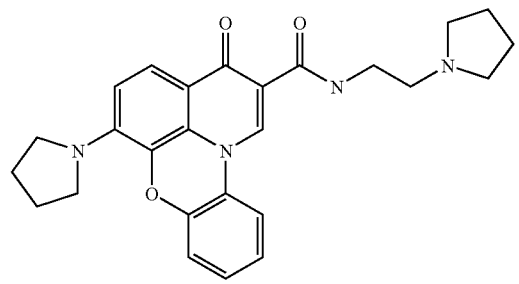
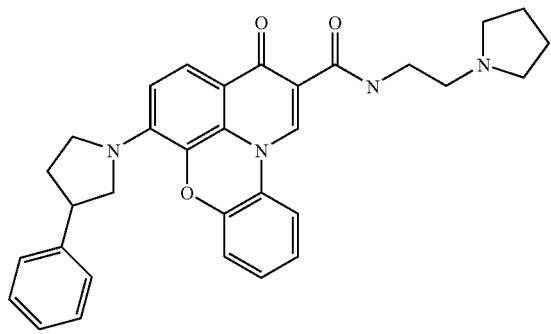
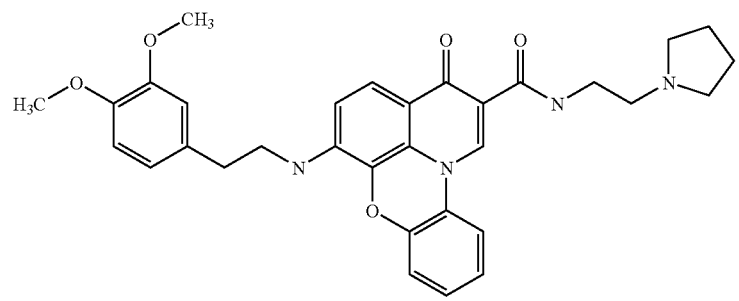
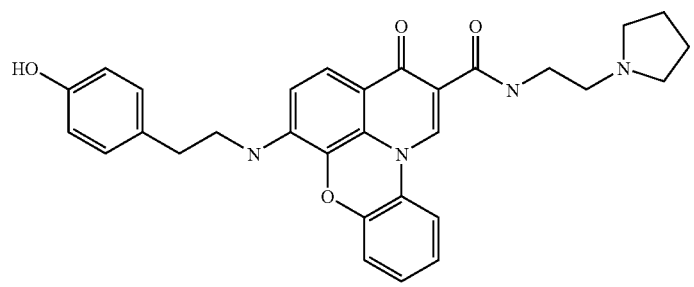

TABLE 1E-continued
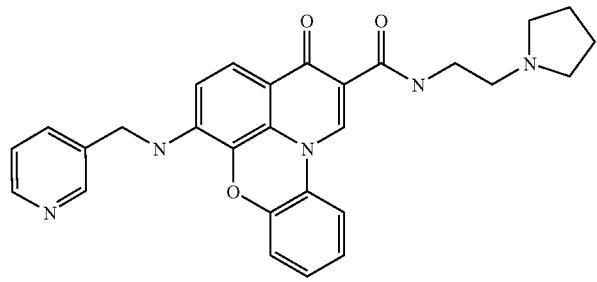
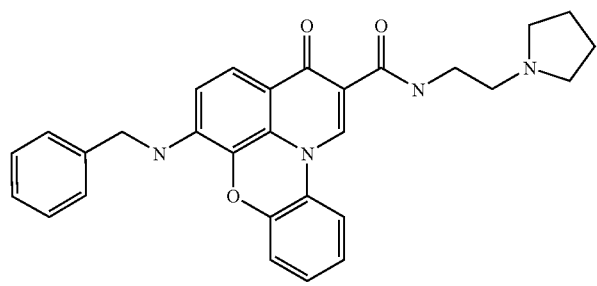
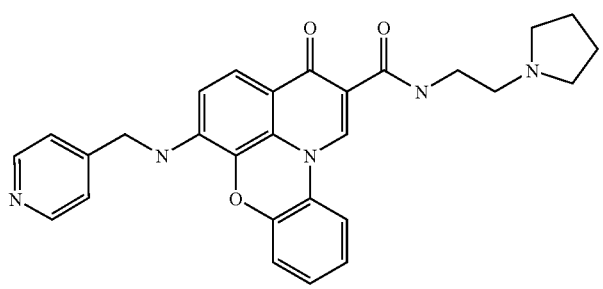
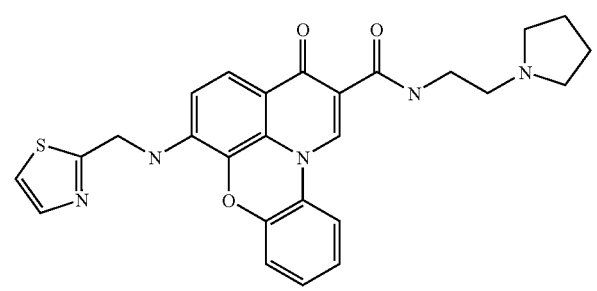
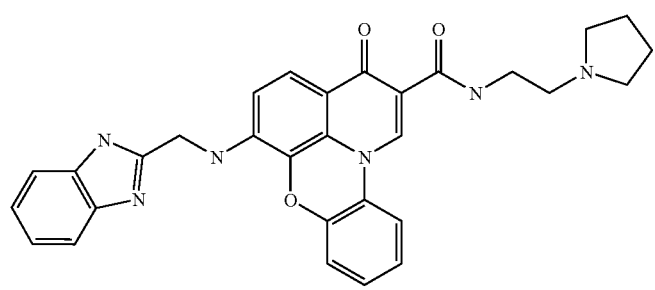

TABLE 1E-continued
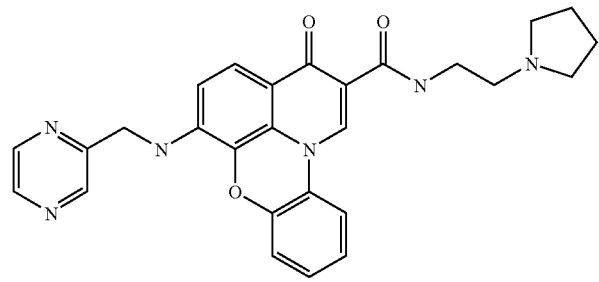
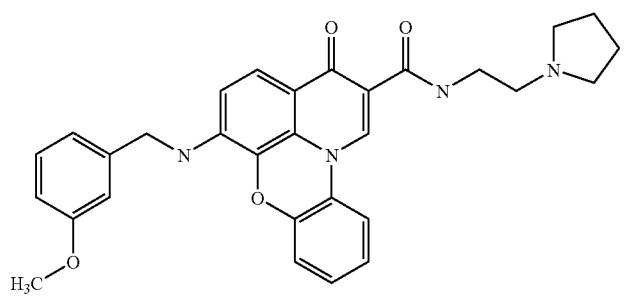
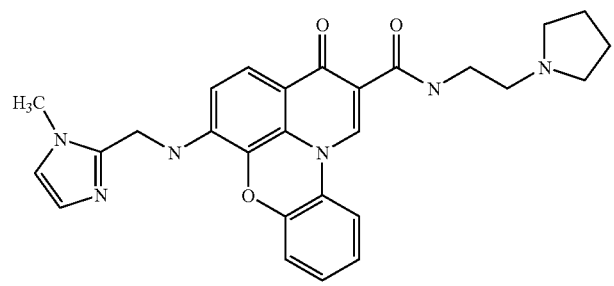
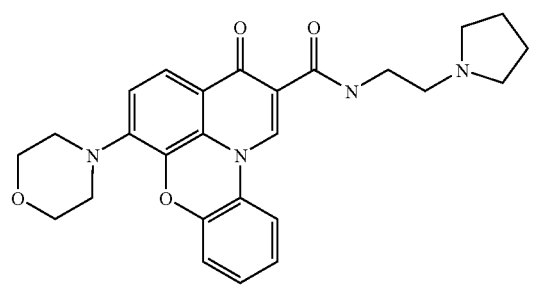
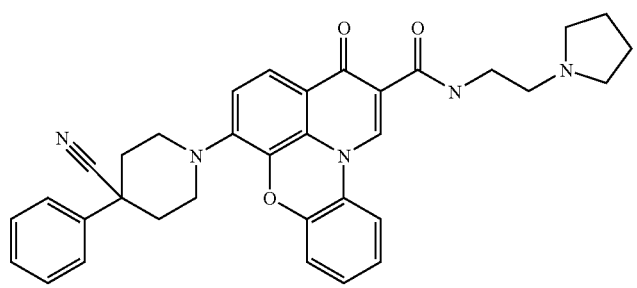

TABLE 1E-continued
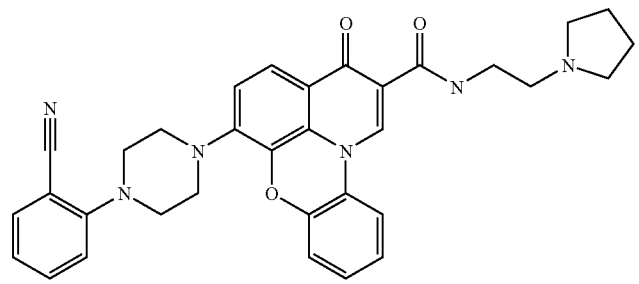
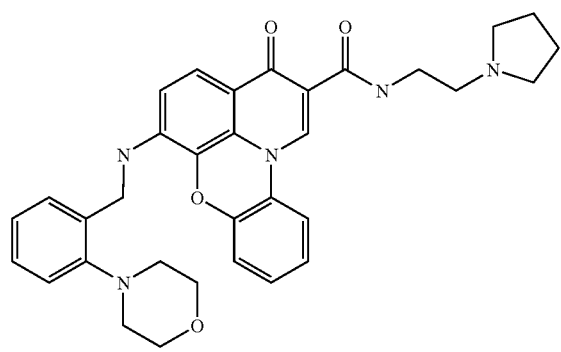
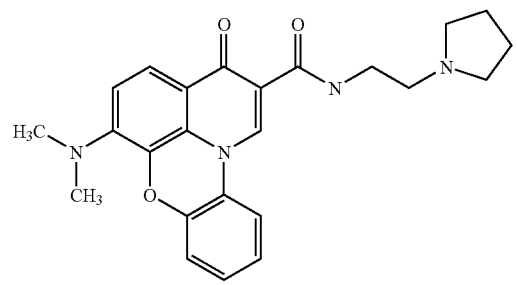
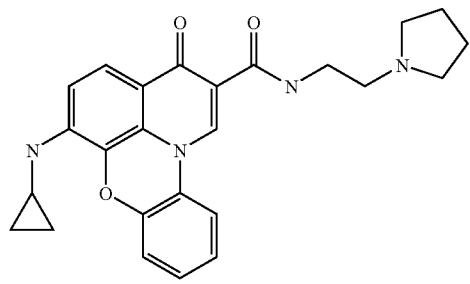
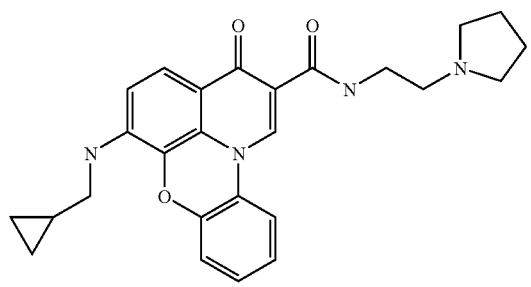

TABLE 1E-continued
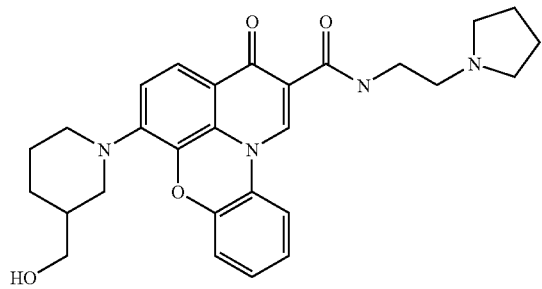
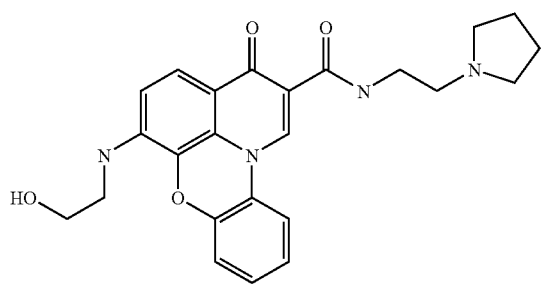
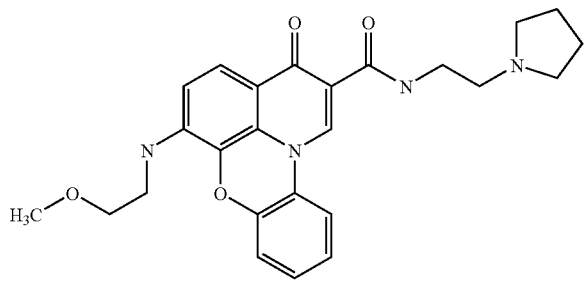
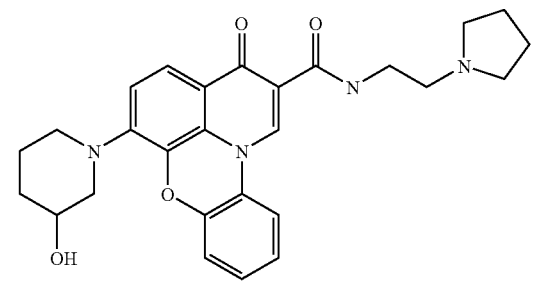
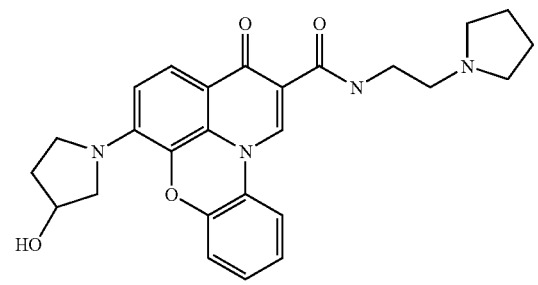

TABLE 1E-continued
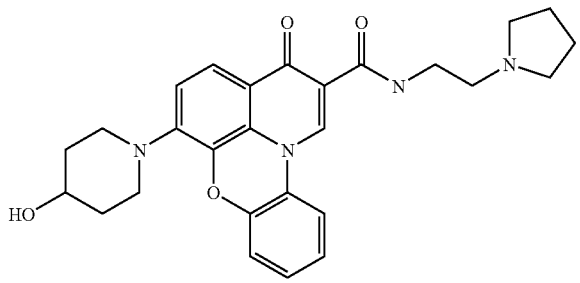
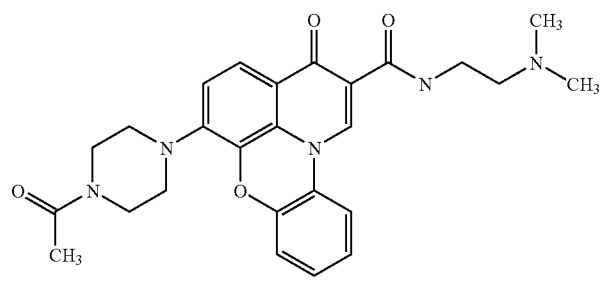
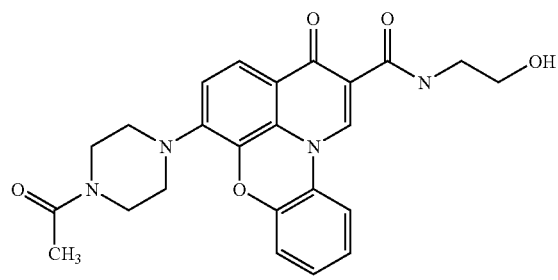
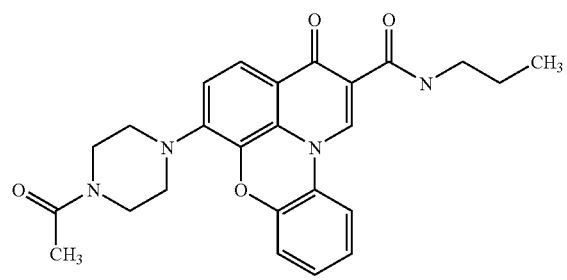
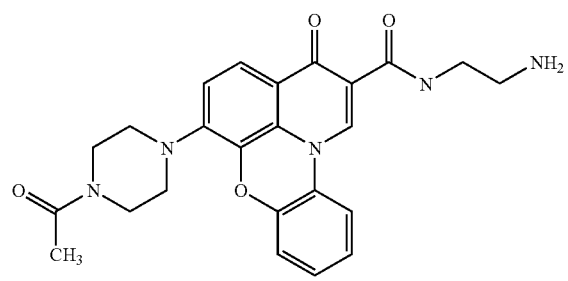

TABLE 1E-continued
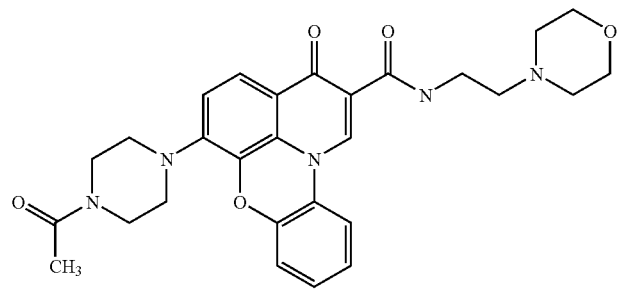
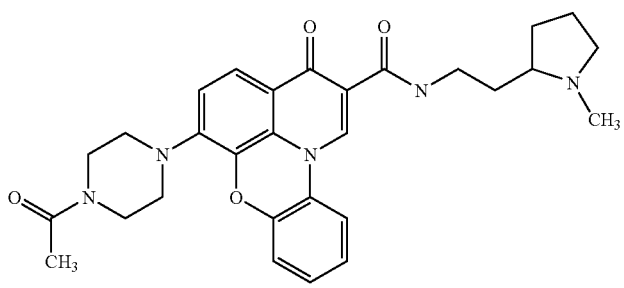
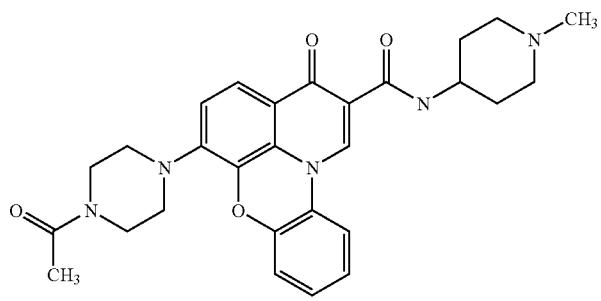
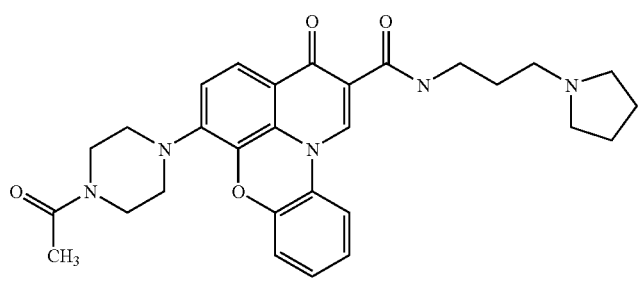
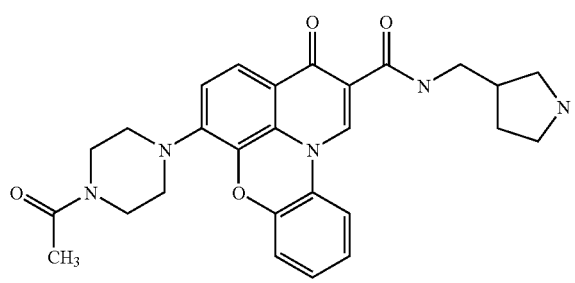

TABLE 1E-continued
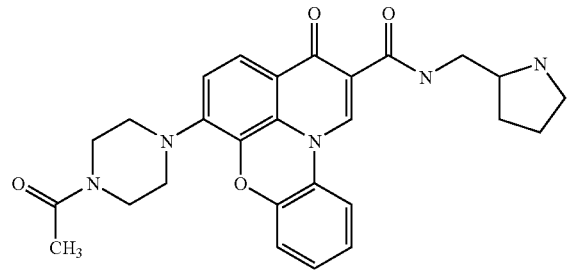
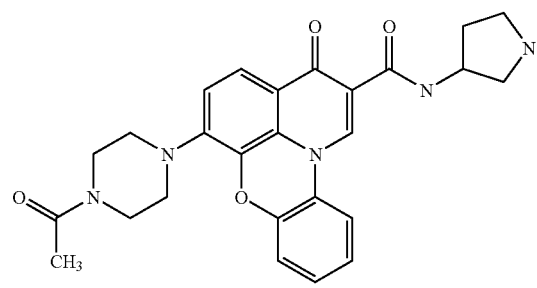
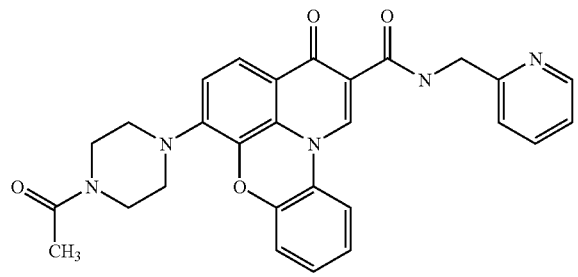
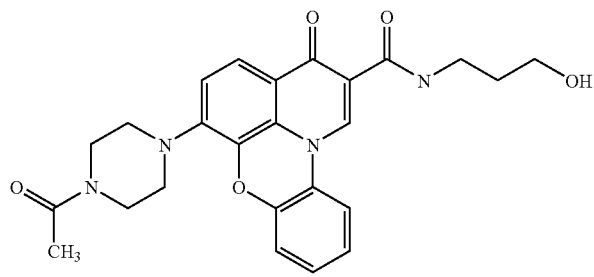
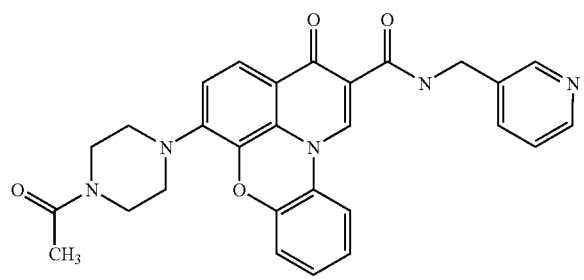

TABLE 1E-continued
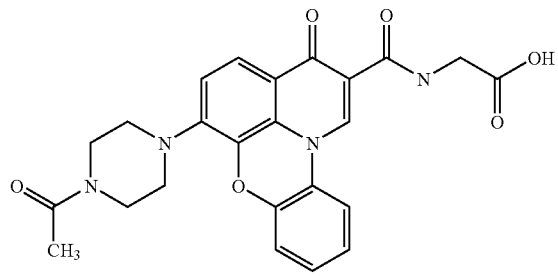
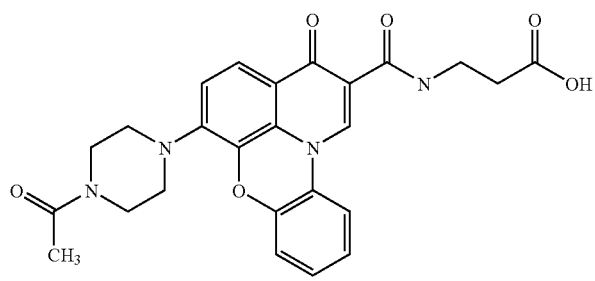
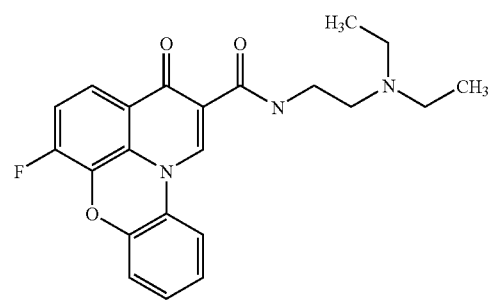
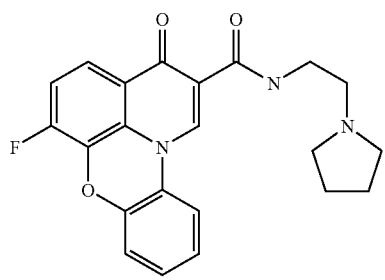
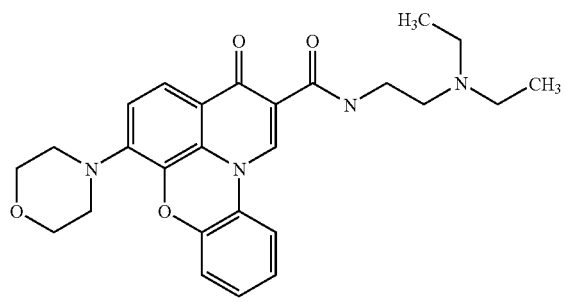

TABLE 1E-continued
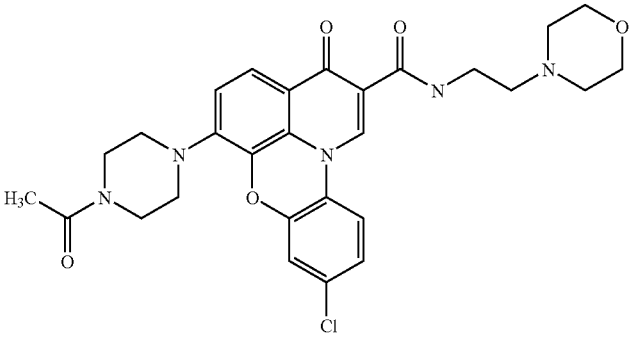
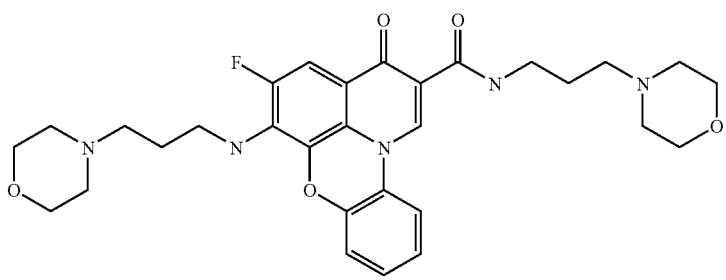
| | | STOP Data (μM) |
|---|---|---|
| 1 | 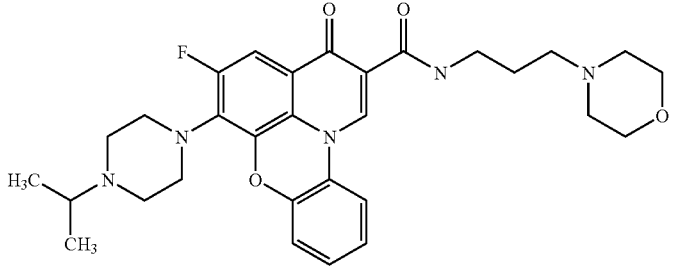 | >15 |
| 2 | | >15 |
| 3 | 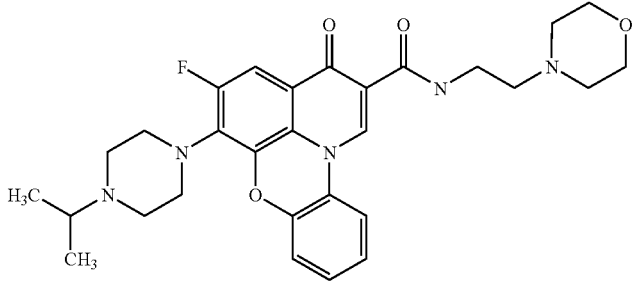 | >15 |

TABLE 1E-continued
| | | |
|---|---|---|
| 4 | 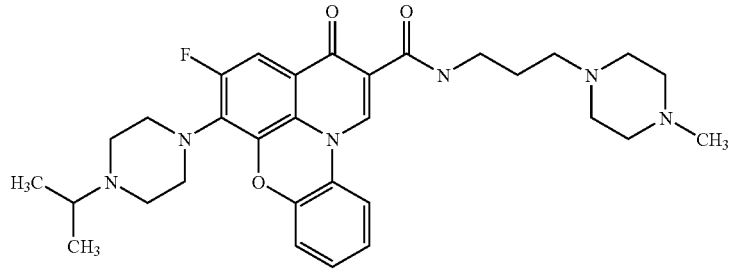 | >15 |
| 5 | 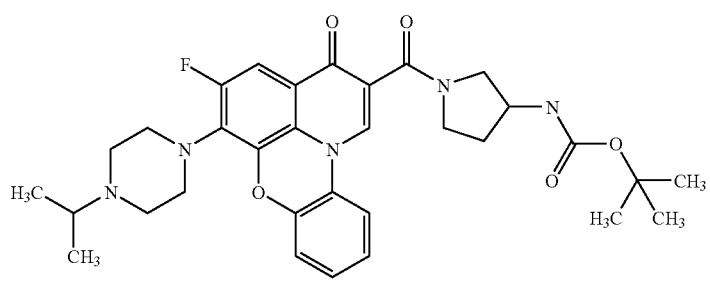 | >15 |
| 6 | 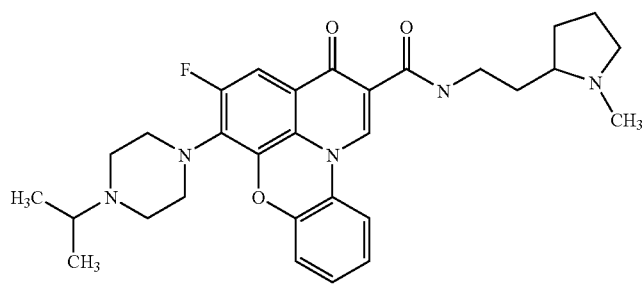 | >15 |
| 7 | 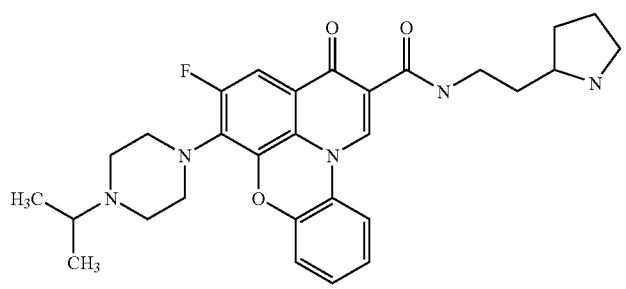 | >15 |
| 8 | 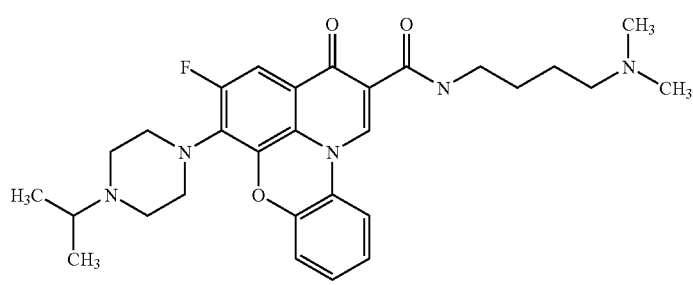 | >15 |

TABLE 1E-continued
| | | |
|---|---|---|
| 9 | 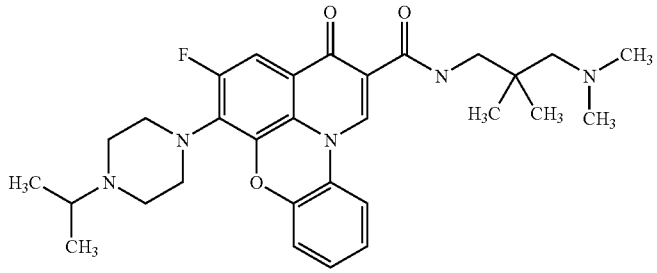 | >15 |
| 10 | 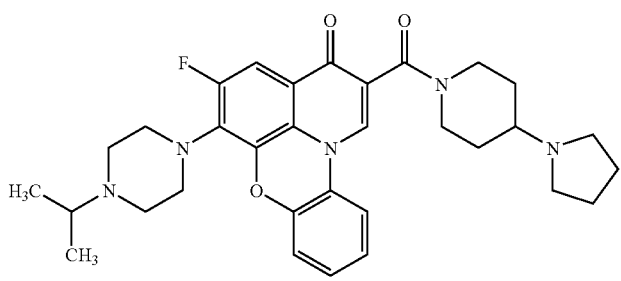 | >15 |
| 11 | 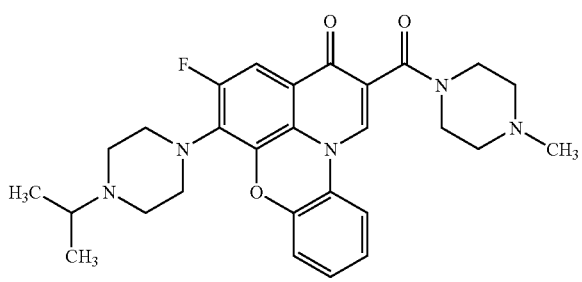 | >15 |
| 12 | 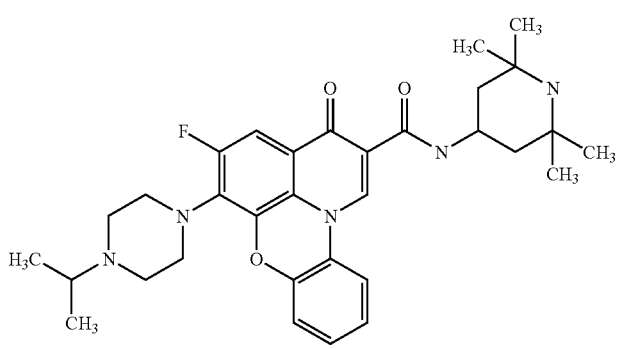 | >15 |
| 13 | 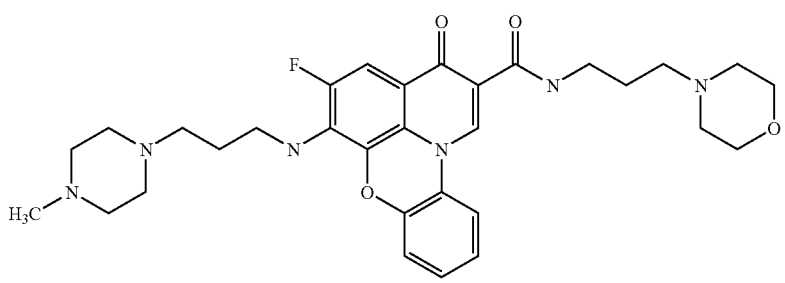 | >15 |

TABLE 1E-continued

| 14 | [structure] | >15 |
| 15 | [structure] | >15 |
| 16 | [structure] | >15 |
| 17 | [structure] | >15 |
| 18 | [structure] | >15 |

TABLE 1E-continued
| 19 | 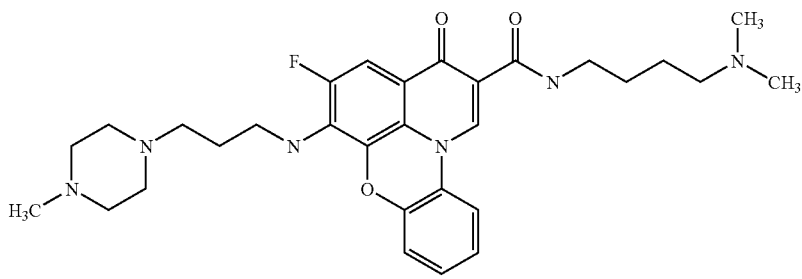 | >15 |
| 20 | 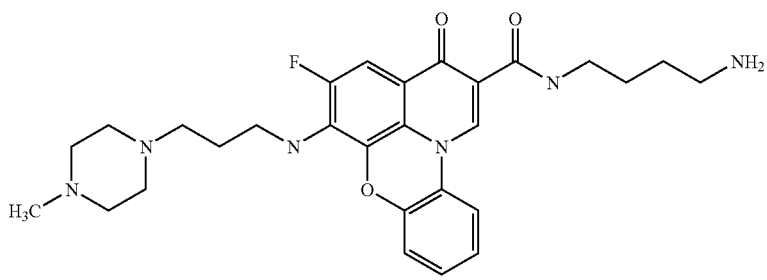 | >15 |
| 21 | 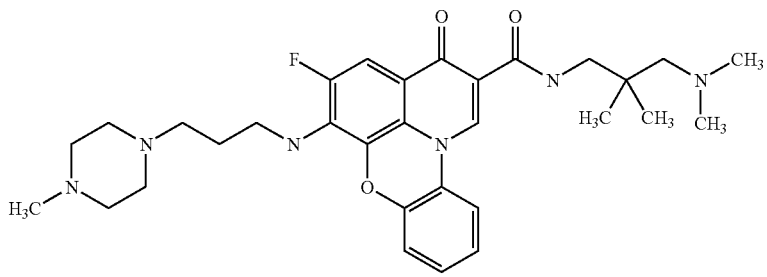 | >15 |
| 22 | 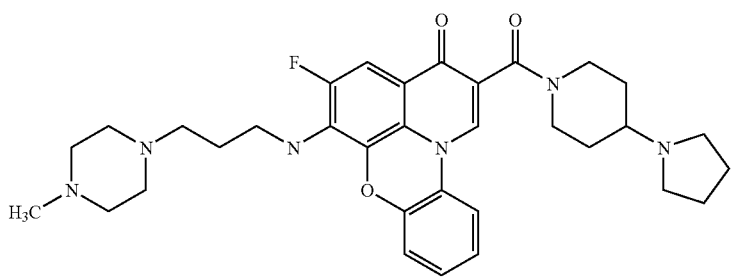 | >15 |
| 23 | 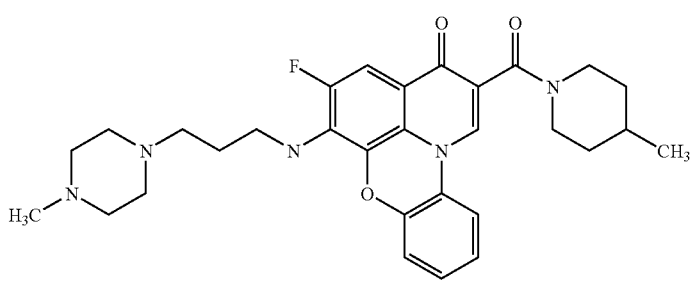 | >15 |

TABLE 1E-continued
| | | |
|---|---|---|
| 24 | 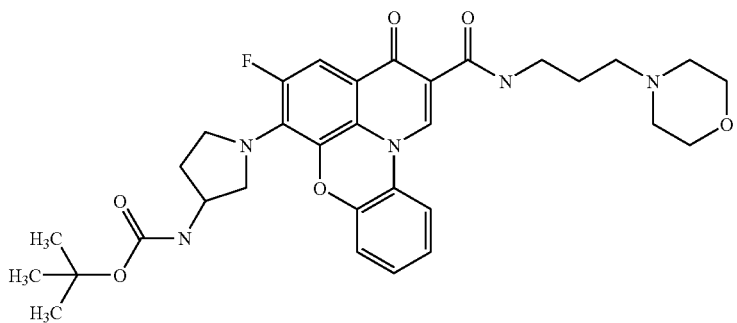 | >15 |
| 25 | 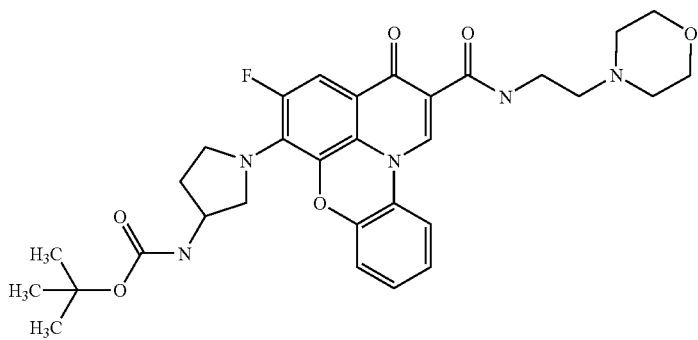 | >15 |
| 26 | 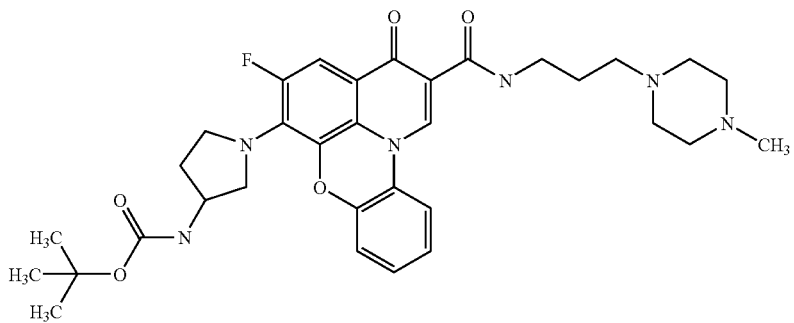 | >15 |
| 27 | 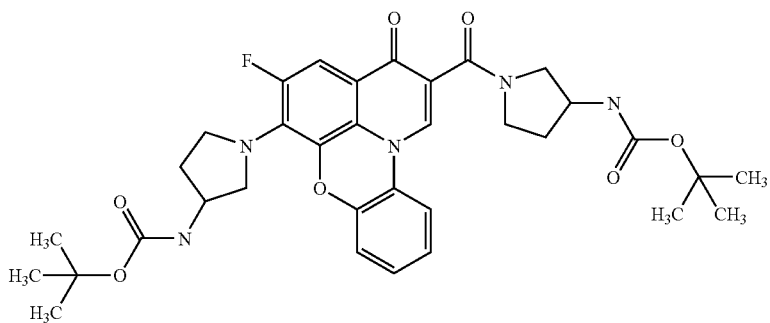 | >15 |

TABLE 1E-continued
| 28 | 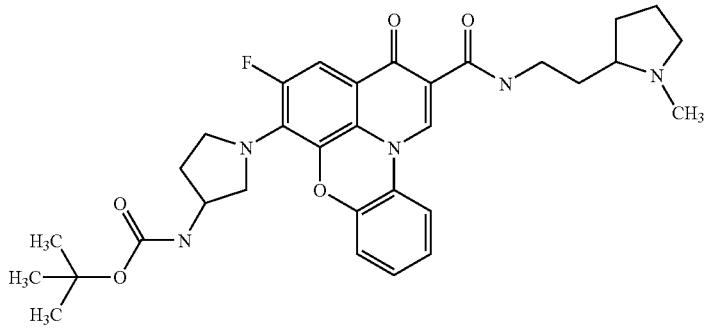 | >15 |
| 29 | 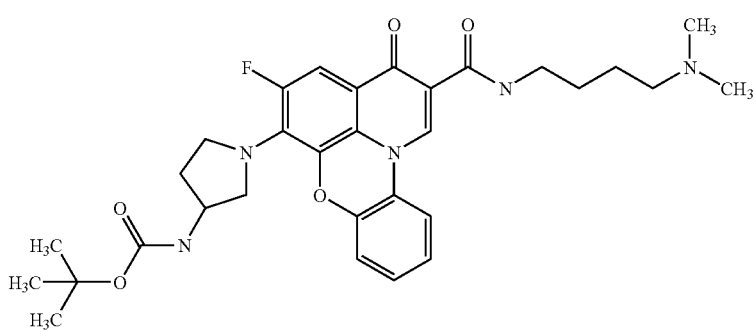 | >15 |
| 30 | 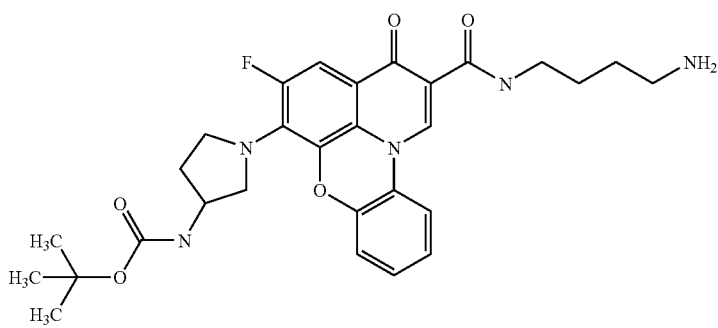 | >15 |
| 31 | 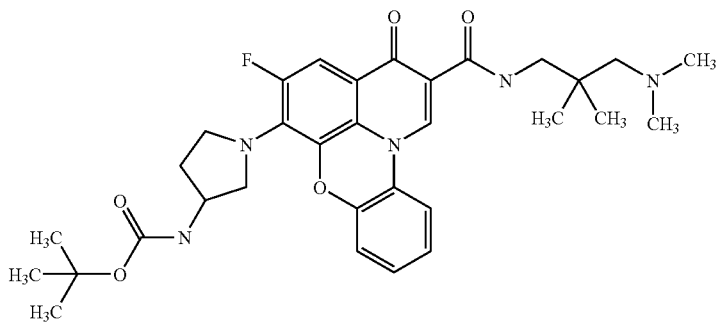 | >15 |

TABLE 1E-continued
| 32 | 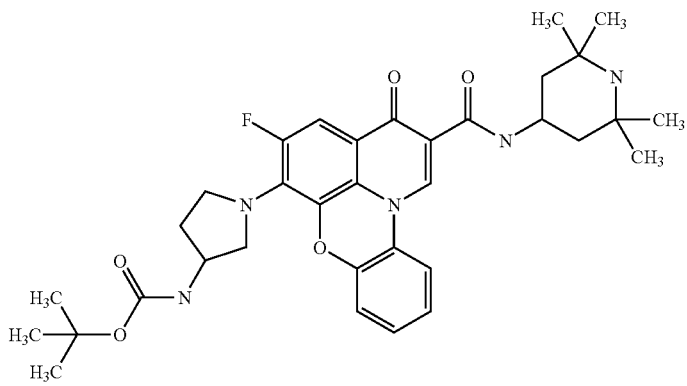 | >15 |
| 33 | 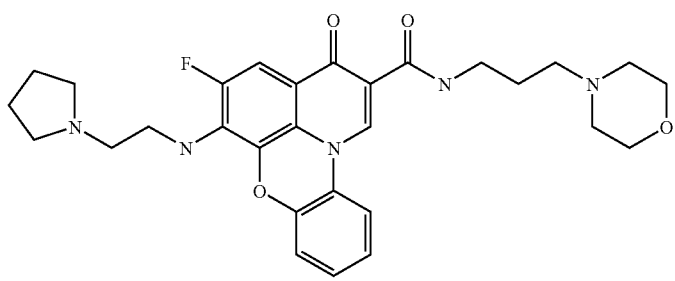 | >15 |
| 34 | 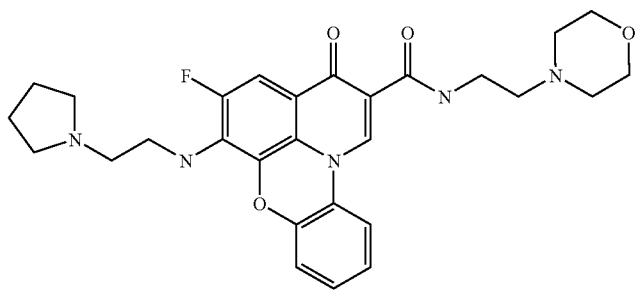 | >15 |
| 35 | 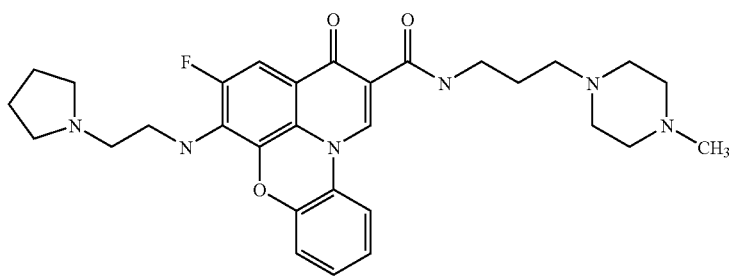 | >15 |
| 36 | 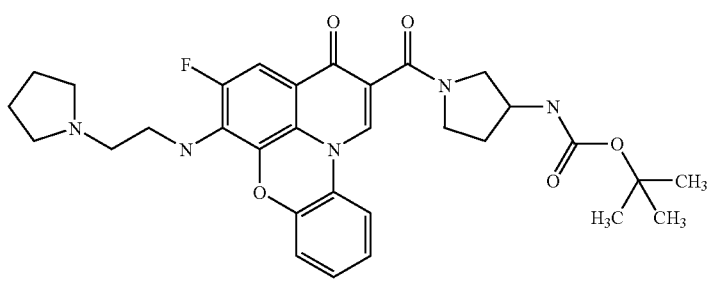 | >15 |

TABLE 1E-continued
| 37 | 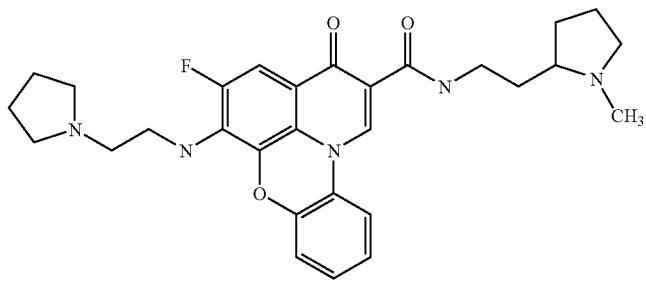 | >15 |
| 38 | 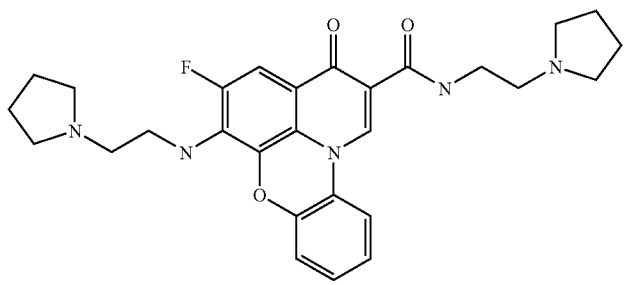 | >15 |
| 39 | 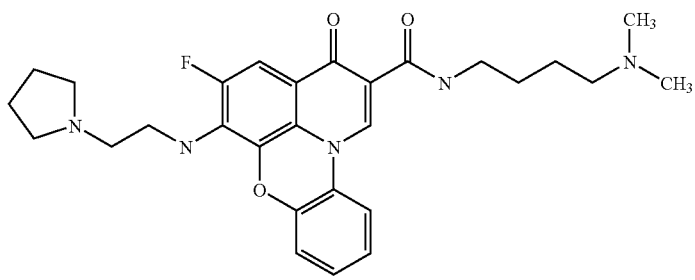 | >15 |
| 40 | 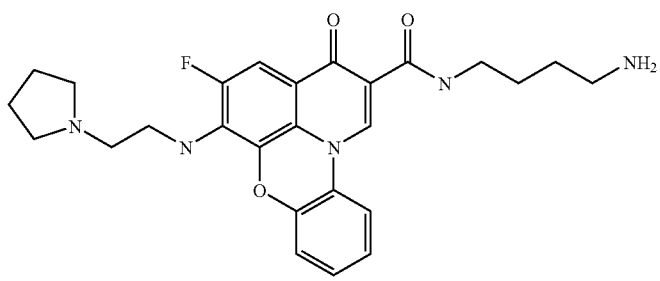 | >15 |
| 41 | 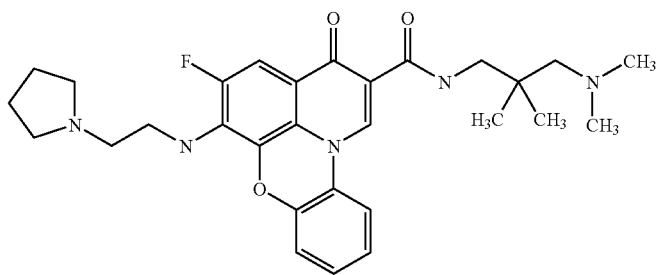 | >15 |

TABLE 1E-continued
| 42 | 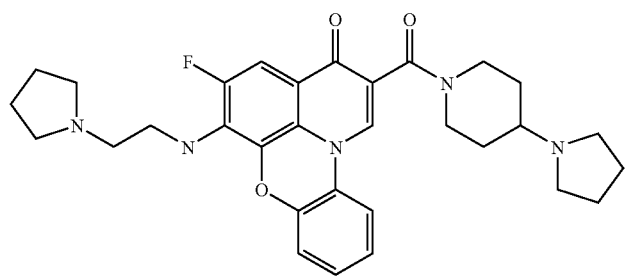 | >15 |
| 43 | 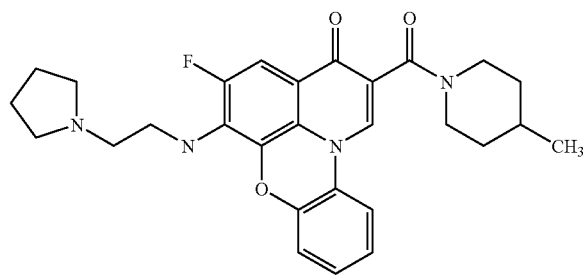 | >15 |
| 44 | 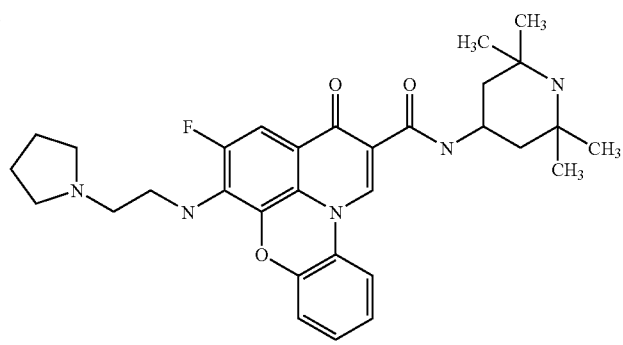 | >15 |
| 45 | 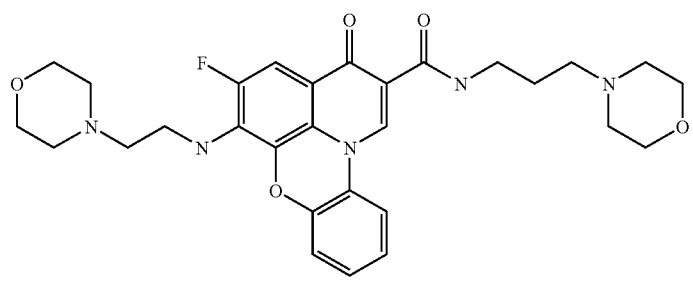 | >15 |
| 46 | 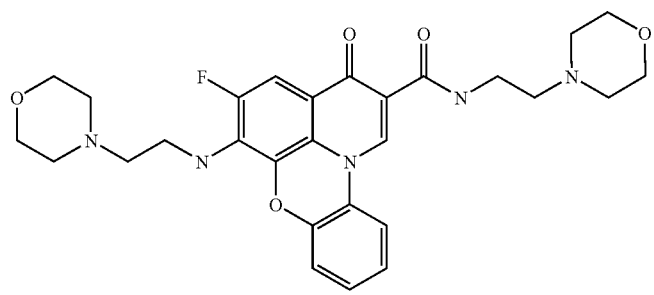 | >15 |

TABLE 1E-continued
| 47 | 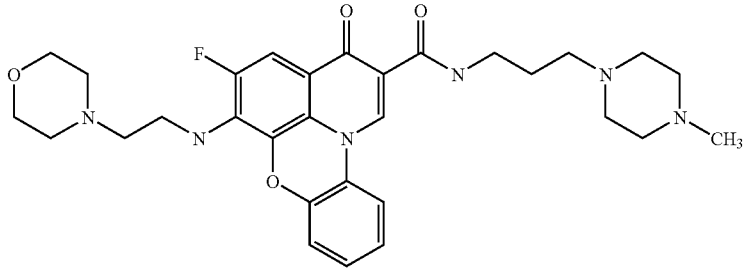 | >15 |
| 48 | 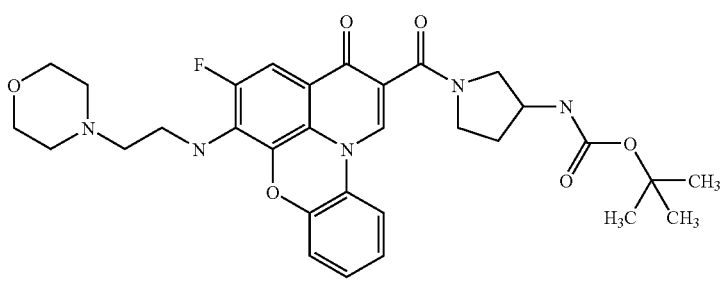 | >15 |
| 49 | 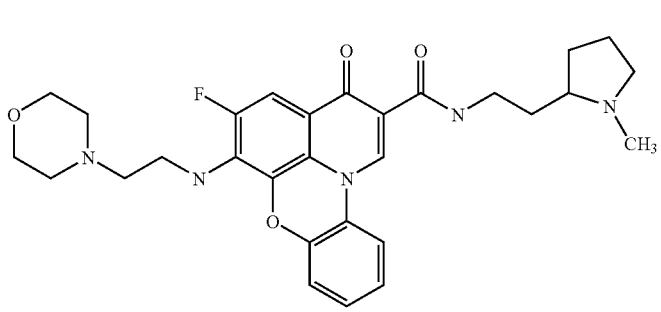 | >15 |
| 50 | 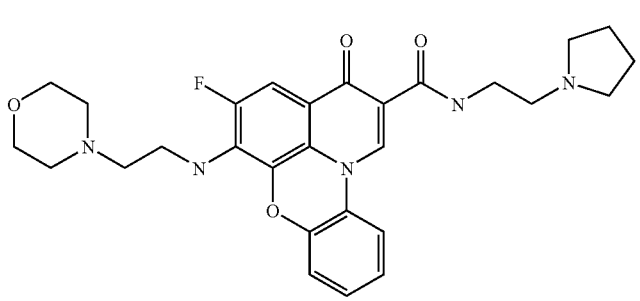 | >15 |
| 51 | 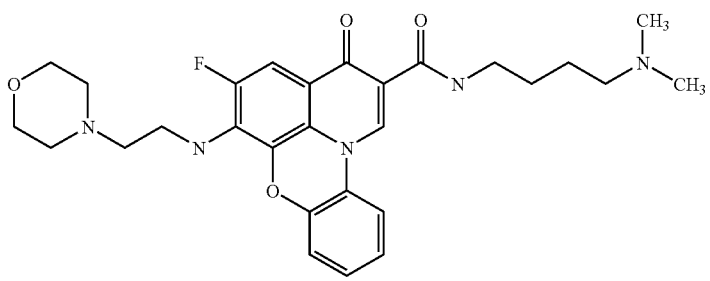 | >15 |

TABLE 1E-continued
| 52 |  | >15 |
| 53 | 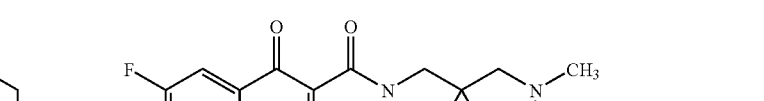 | >15 |
| 54 | 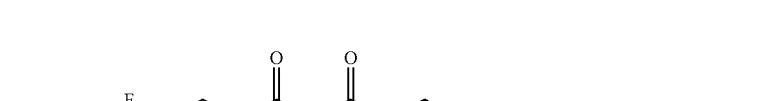 | >15 |
| 55 | 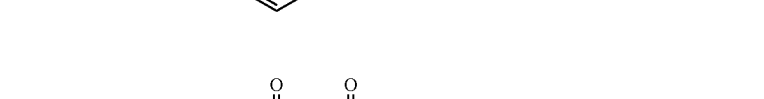 | >15 |
| 56 |  | >15 |

TABLE 1E-continued

| | | |
|---|---|---|
| 57 | (structure) | >15 |
| 58 | (structure) | >15 |
| 59 | (structure) | 0.75 |
| 60 | (structure) | >15 |
| 61 | (structure) | >15 |

TABLE 1E-continued

| # | Structure | Value |
|---|---|---|
| 62 | (structure) | 0.75 |
| 63 | (structure) | >15 |
| 64 | (structure) | >15 |
| 65 | (structure) | >15 |
| 66 | (structure) | >15 |

TABLE 1E-continued
| 67 | 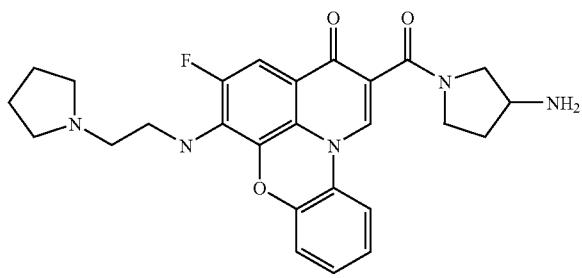 | >15 |
| 68 | 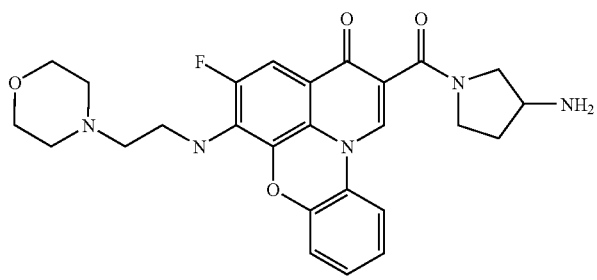 | >15 |
| 69 | 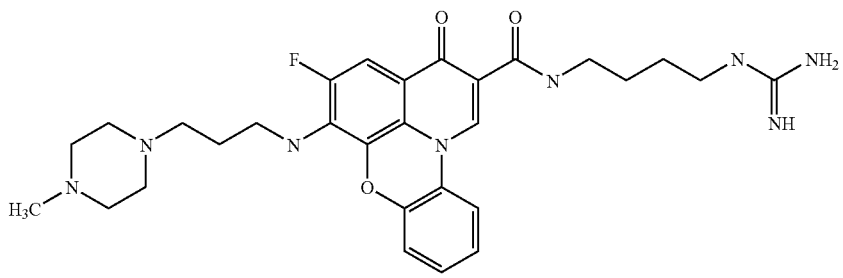 | >15 |
| 70 | 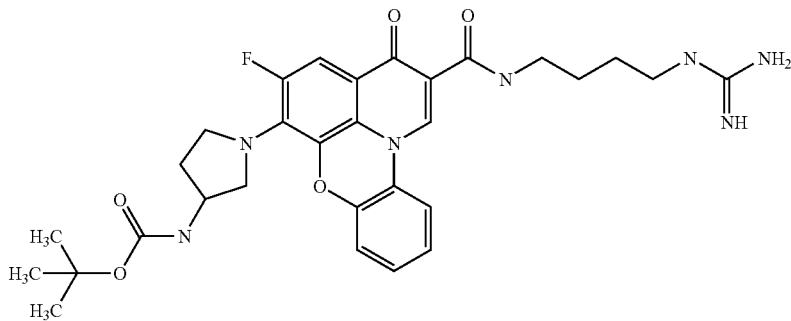 | >15 |
| 71 | 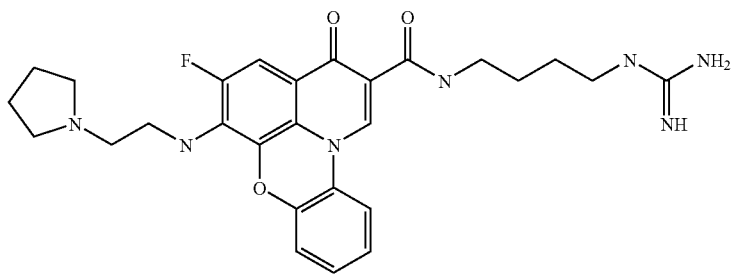 | >15 |

TABLE 1E-continued

| 72 | [structure] | >15 |
| 73 | [structure] | 3 |
| 74 | [structure] | 3 |
| 75 | [structure] | 11 |

TABLE 1E-continued
| | | |
|---|---|---|
| 76 | 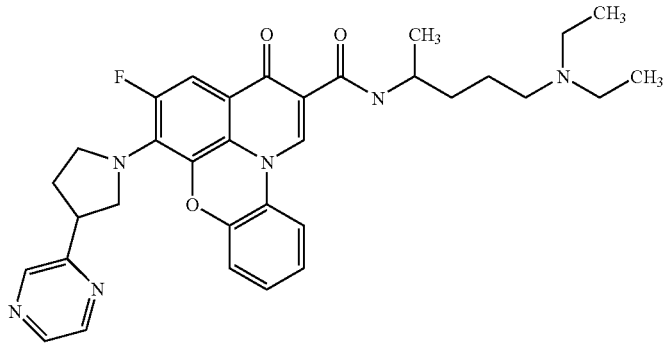 | 3 |
| 77 | 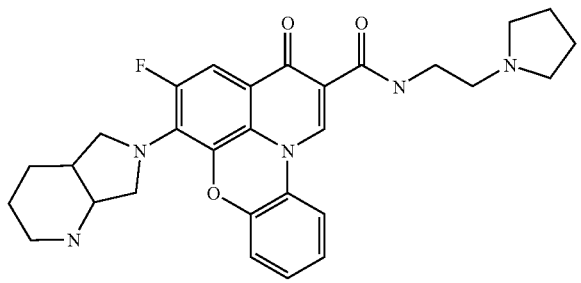 | >15 |
| 78 | 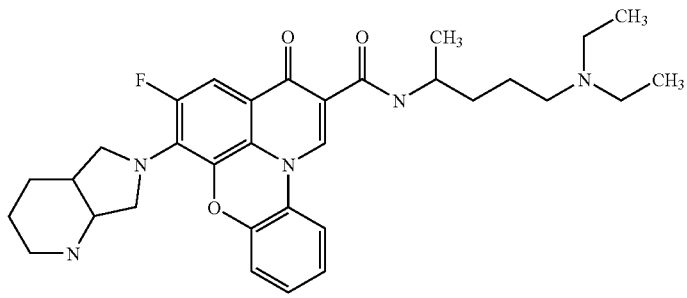 | >15 |
| 79 | 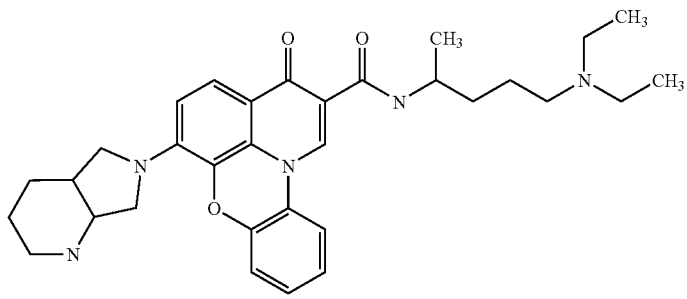 | >15 |
| 80 | 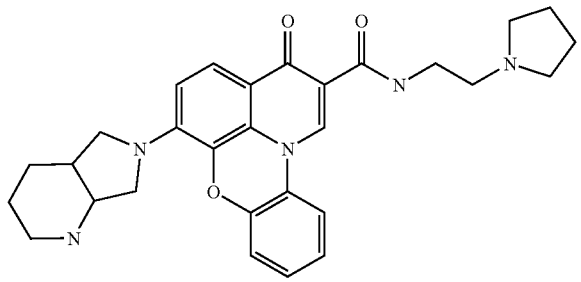 | >15 |

TABLE 1E-continued
| 81 | 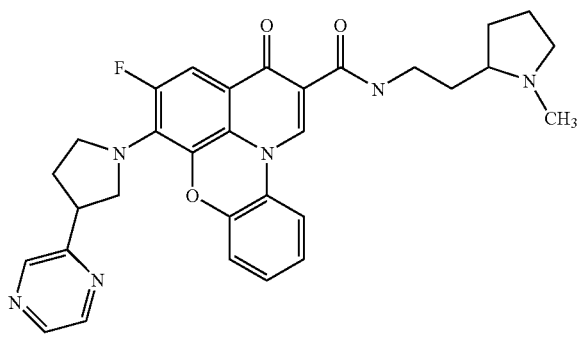 | Chiral | 5.7 |
| 82 | 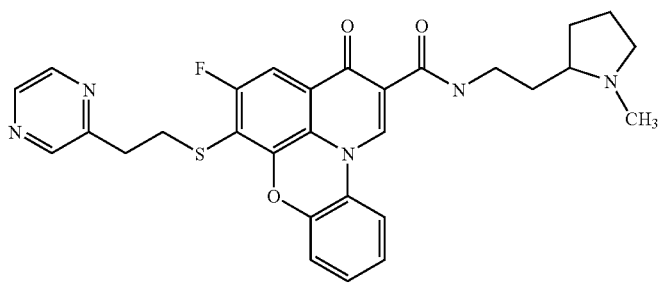 | | >15 |
| 83 | 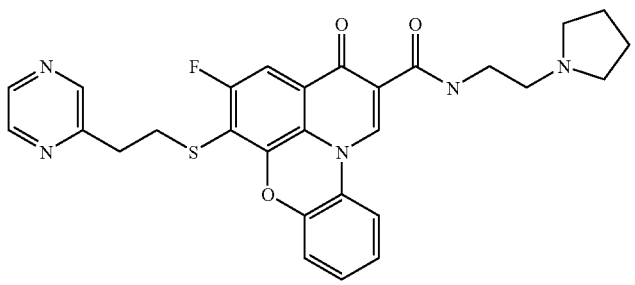 | | >15 |
| 84 | 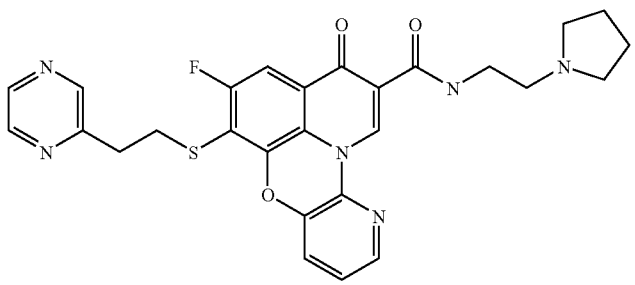 | | >15 |
| 85 | 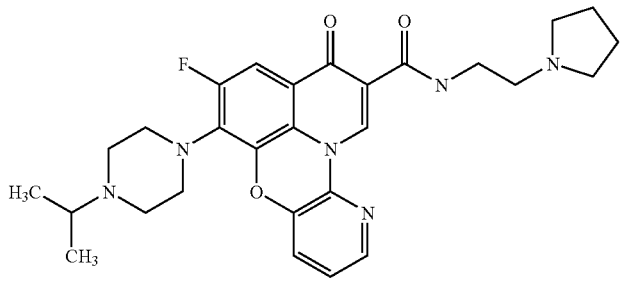 | | 8.2 |

TABLE 1F
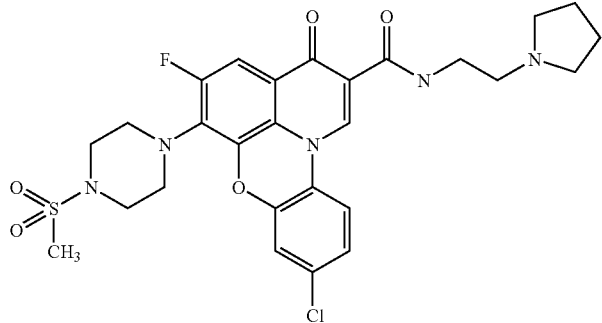
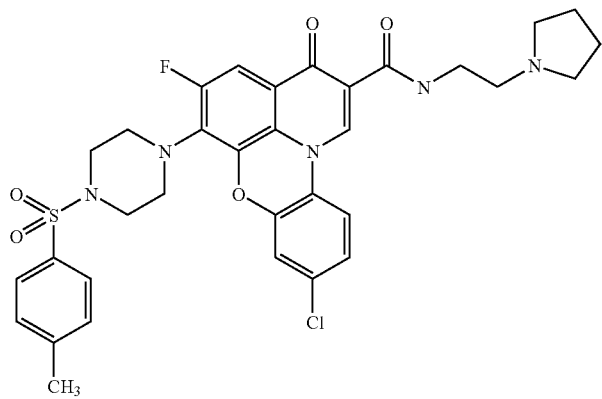
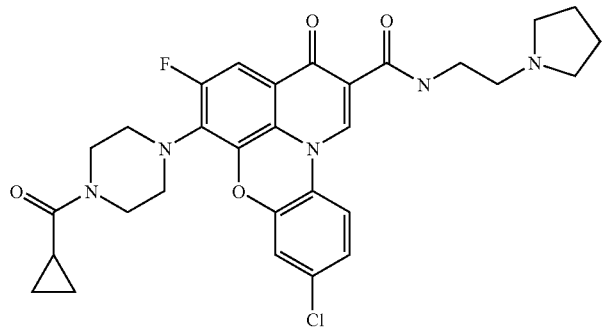
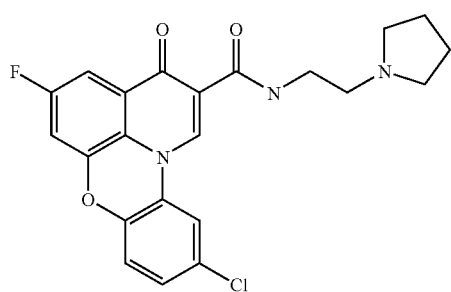

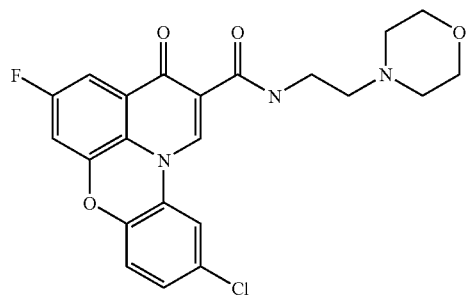
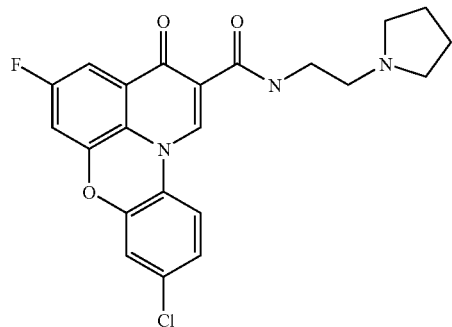
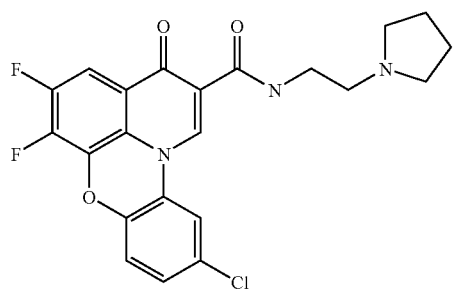
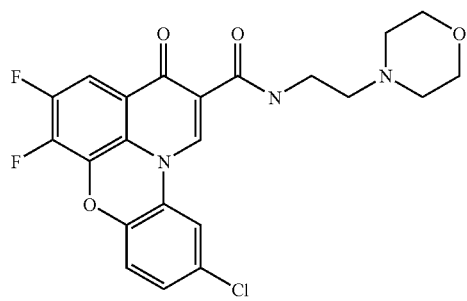
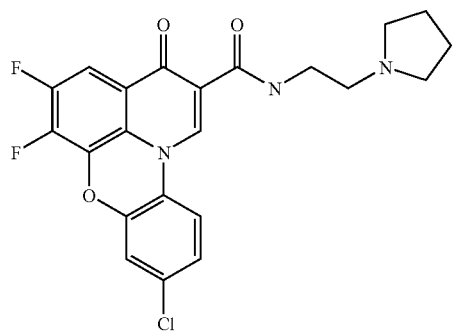

101 102
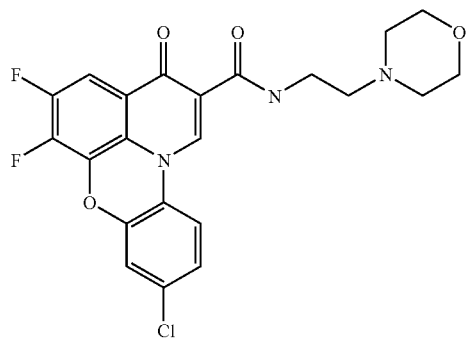
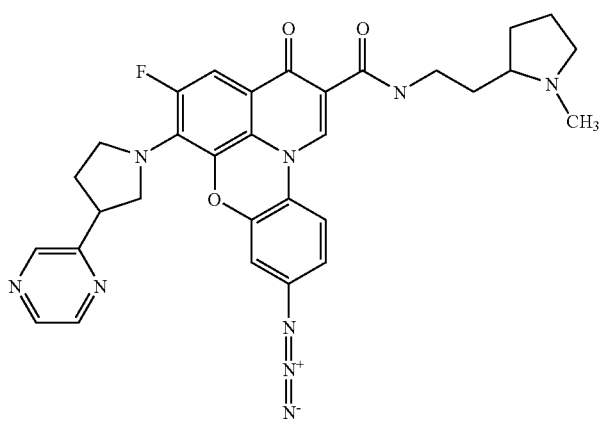
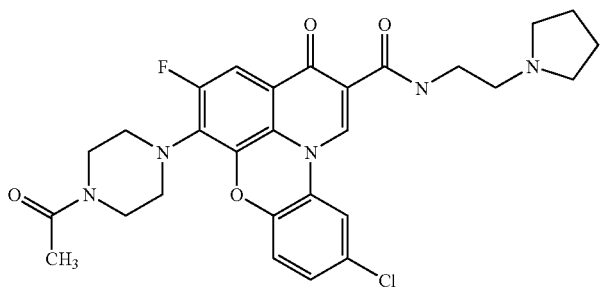
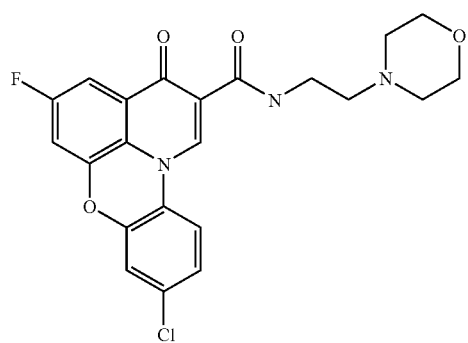

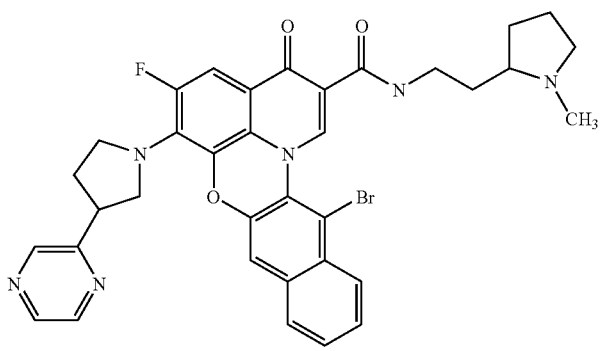
| | | STOP DATA (μM) |
|---|---|---|
| 1 | 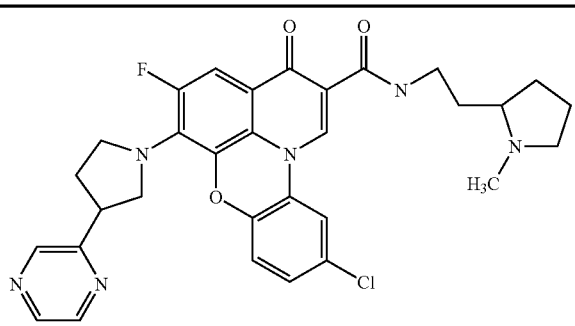 | 4.8 |
| 2 | 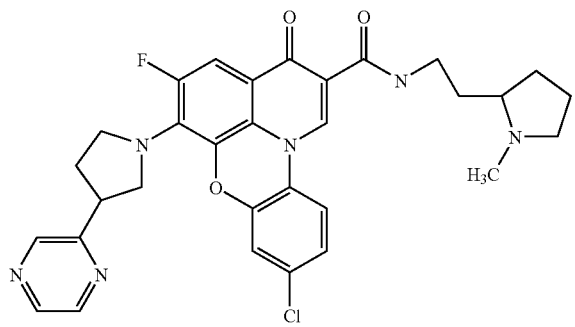 | 3.6 |
| 3 | 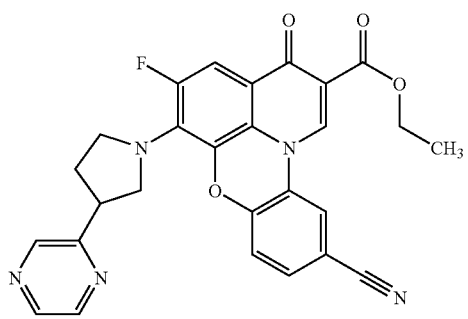 | >15 |
| 4 | 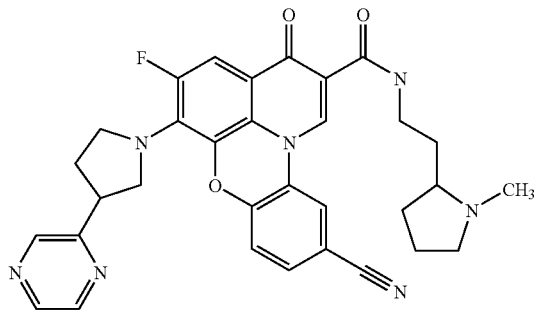 | 6.8 |

| 5 | 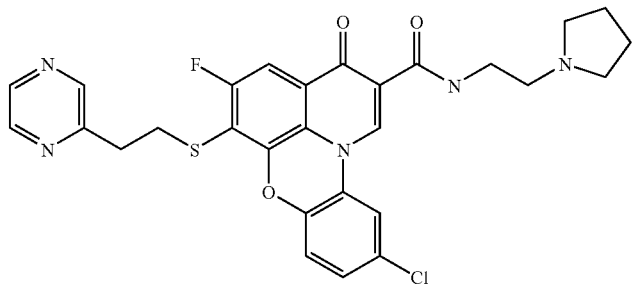 | >15 |
| 6 | 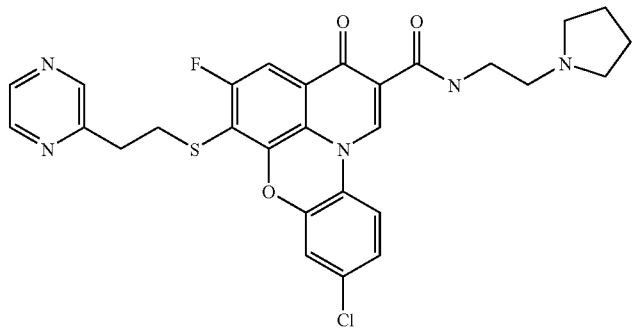 | >15 |
| 7 | 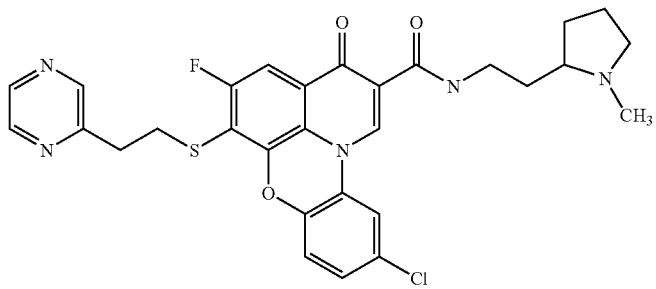 | >15 |
| 8 | 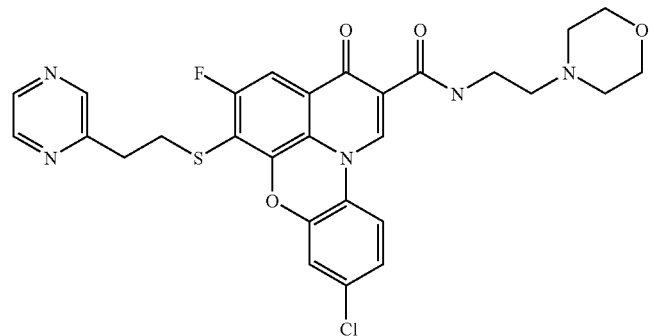 | >15 |
| 9 | 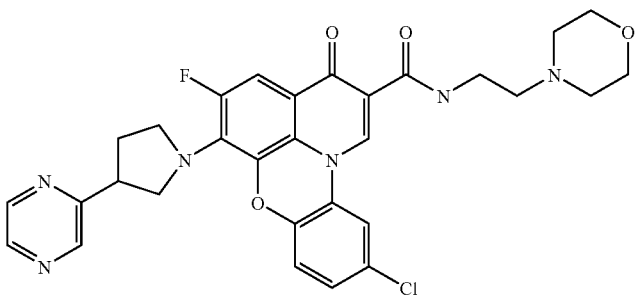 | >15 |

| 10 | 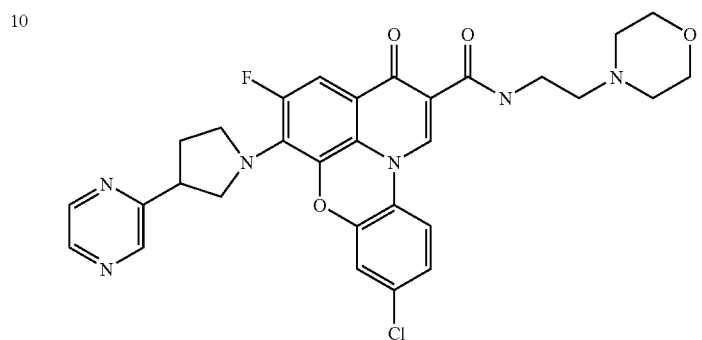 | >15 |
| 11 | 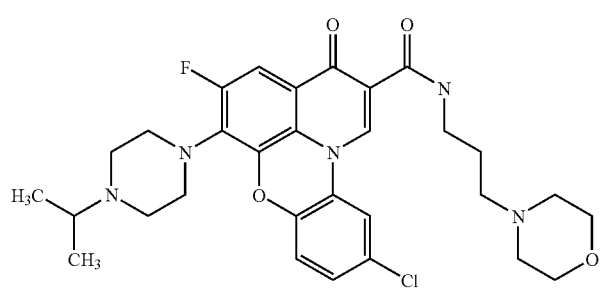 | >15 |
| 12 | 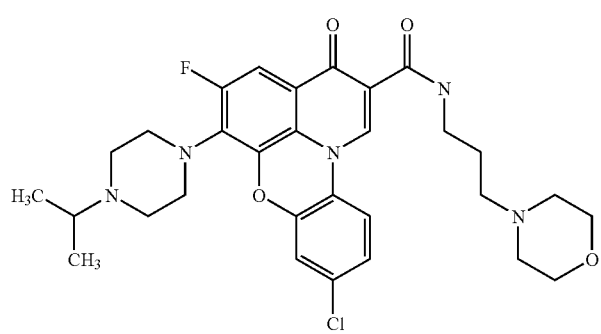 | >15 |
| 13 | 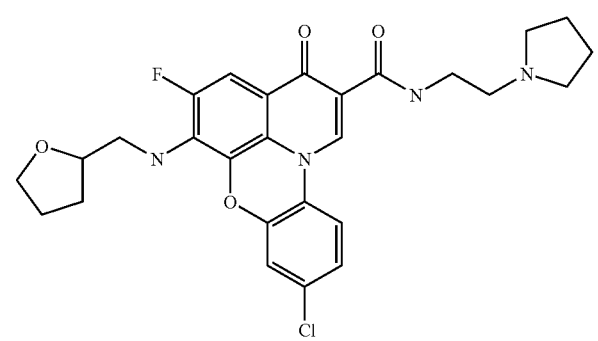 | >15 |
| 14 | 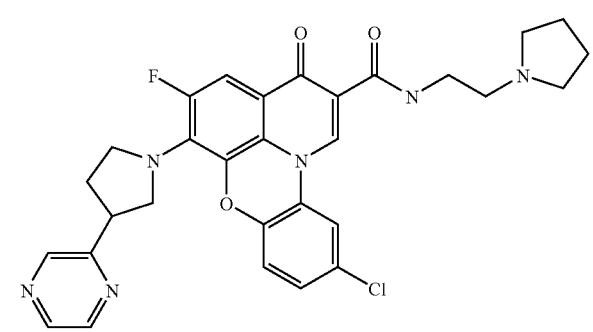 | 2.9 |

| 15 | 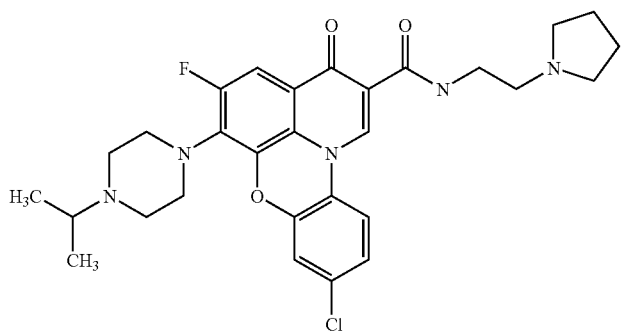 | 8 |
| 16 | 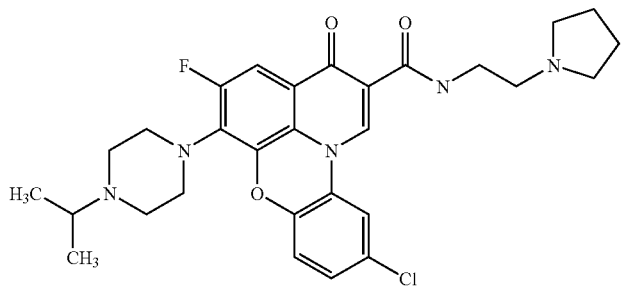 | 6.6 |
| 17 | 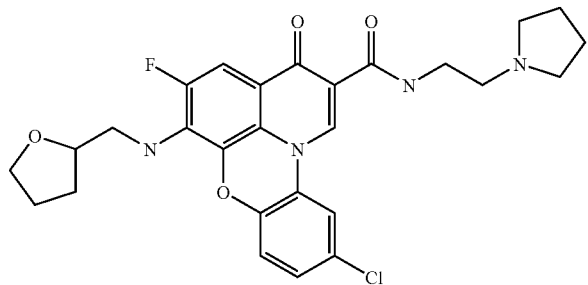 | >15 |
| 18 | 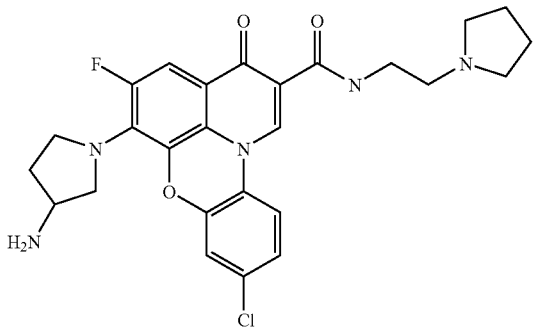 | 2.6 |
| 19 | 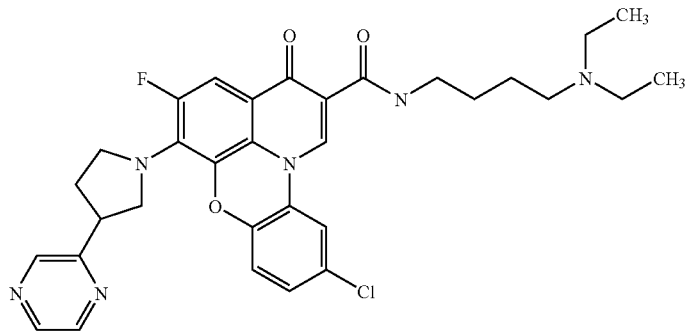 | 4 |

| | | | |
|---|---|---|---|
| 20 | 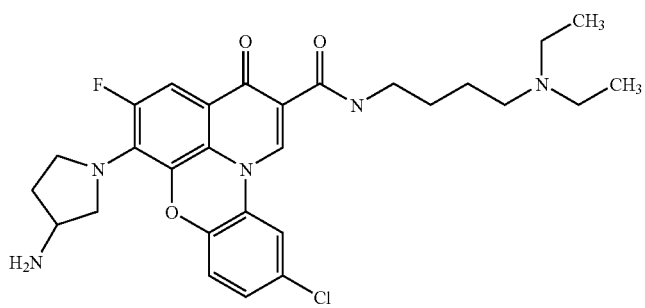 | 111 | 3 |
| 21 | 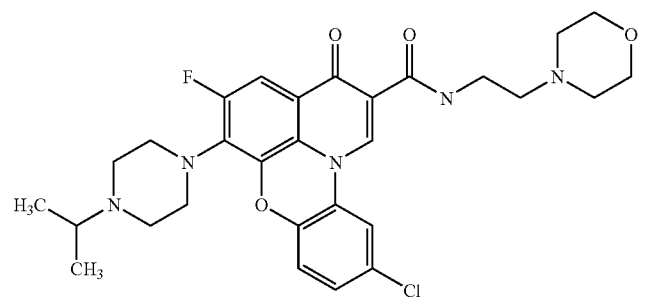 | | >15 |
| 22 | 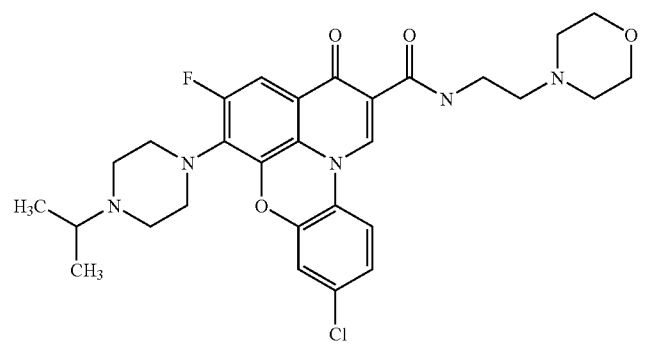 | | >15 |
| 23 | 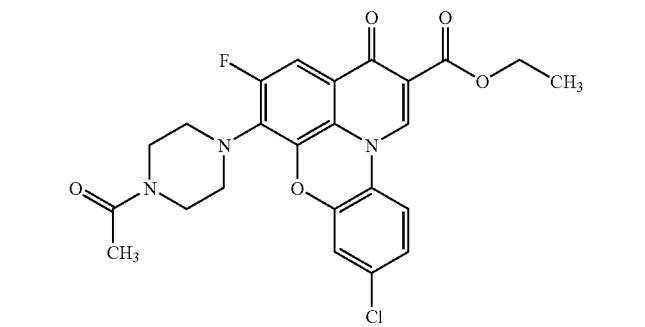 | | >15 |
| 24 | 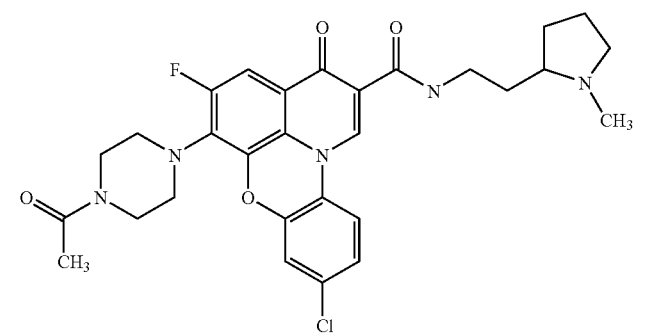 | | >15 |

| | | |
|---|---|---|
| 25 | 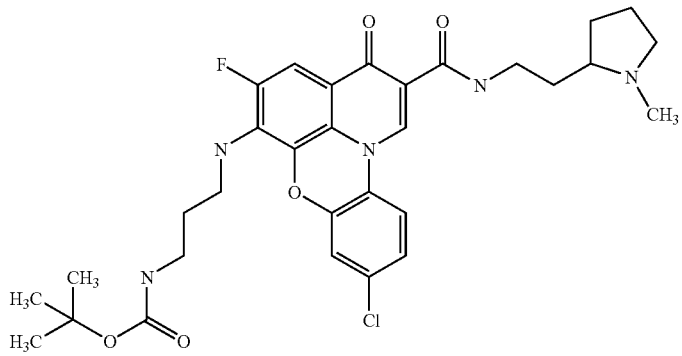 | >15 |
| 26 | 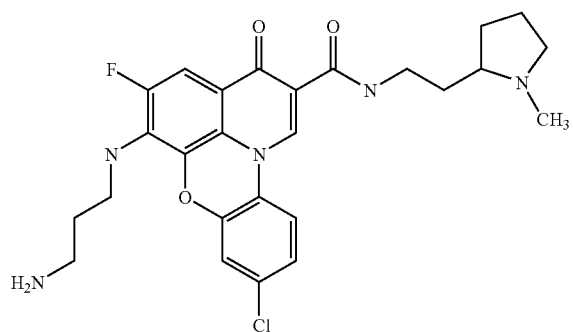 | 4.0 |
| 27 | 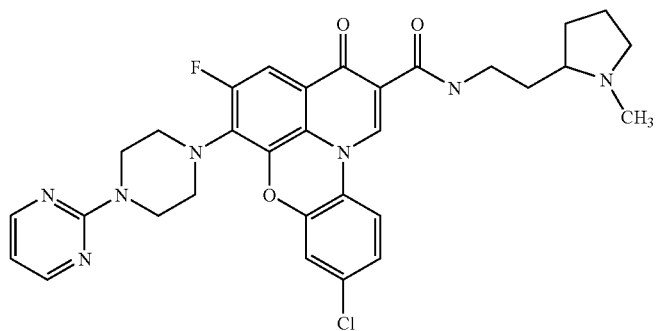 | 7.8 |
| 28 | 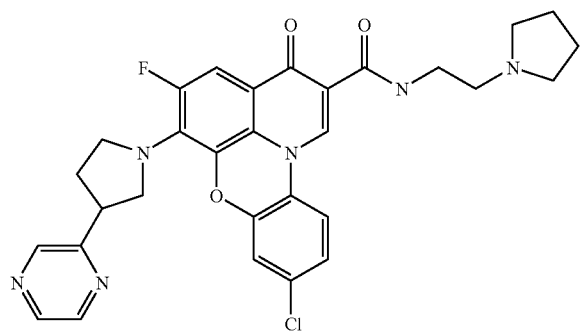 | 2.8 |
| 29 | 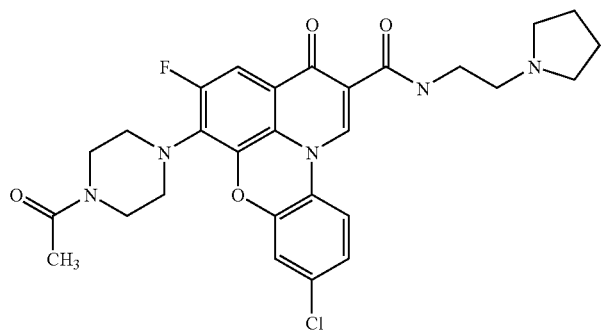 | 3.2 |

| | | |
|---|---|---|
| 30 | 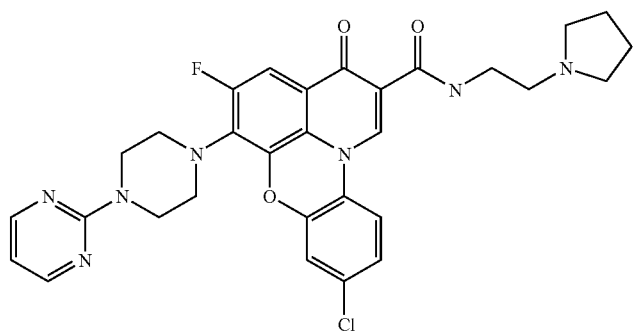 | 5.1 |
| 31 | 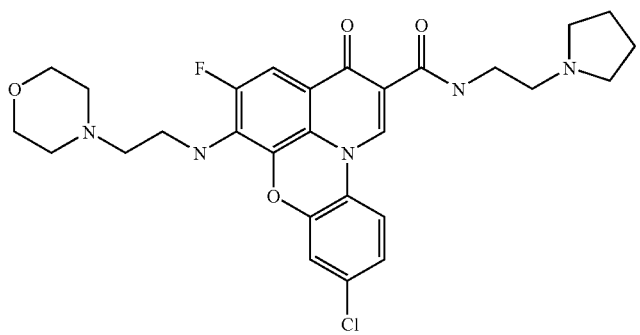 | 7.2 |
| 32 | 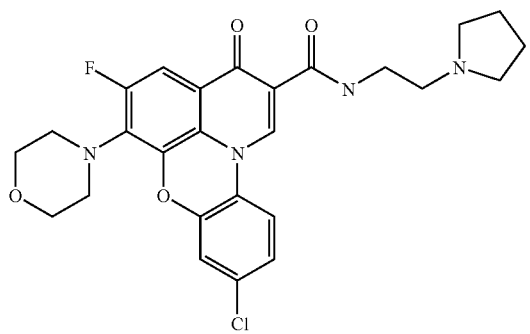 | 10 |
| 33 | 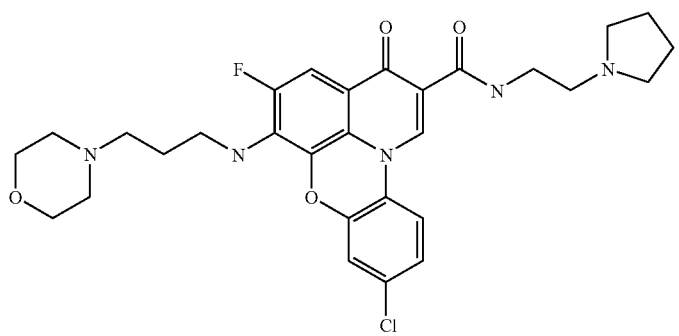 | 5.0 |
| 34 | 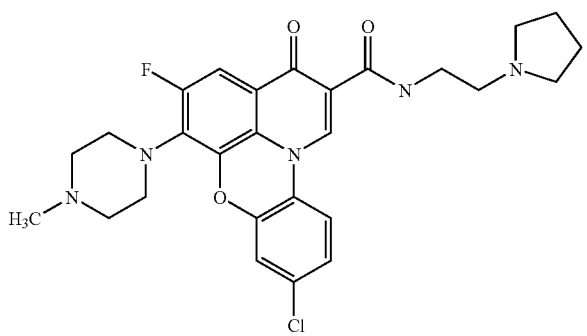 | 10 |

| 35 | 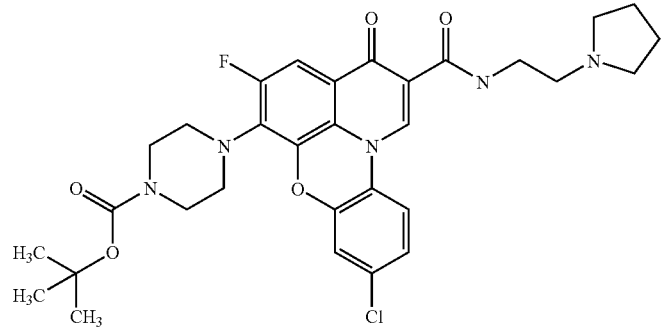 | 2.9 |
| 36 | 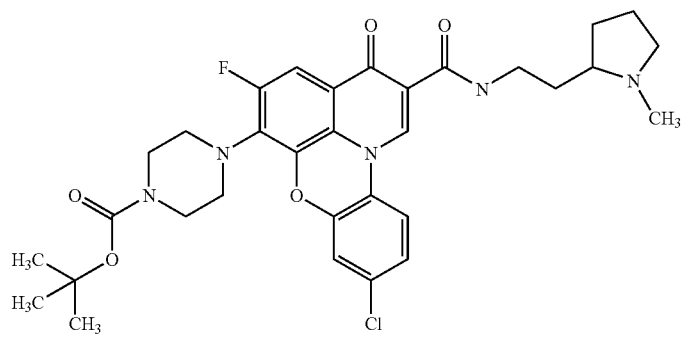 | 10 |
| 37 | 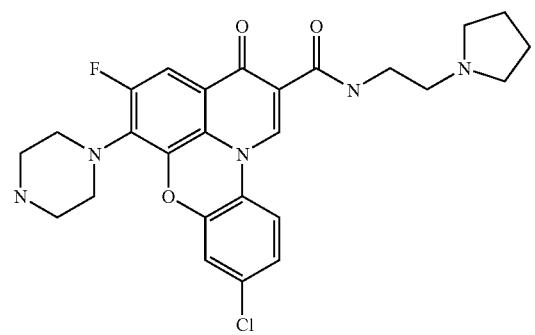 | 8.2 |
| 38 | 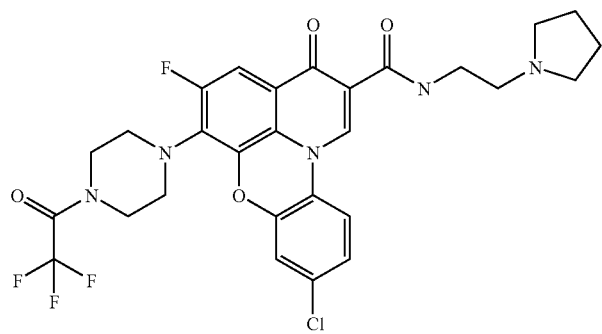 | 10 |

| # | | |
|---|---|---|
| 39 | 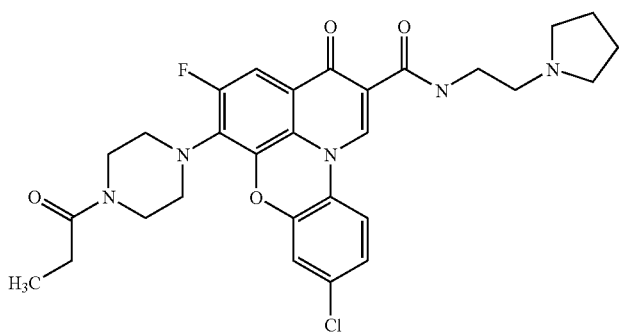 | 10 |
| 40 | 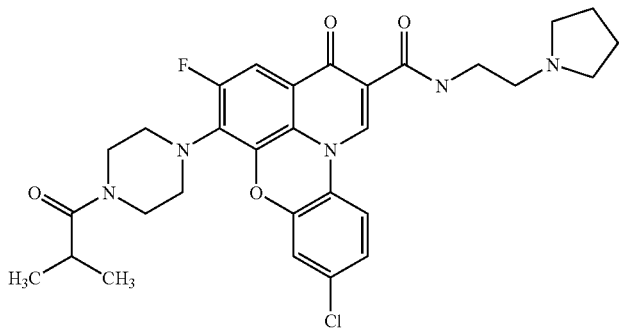 | 10 |
| 41 | 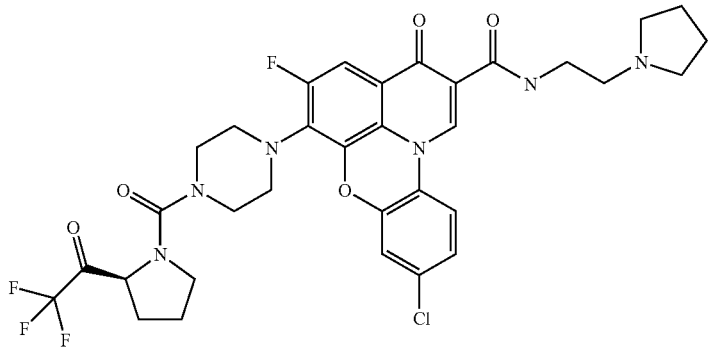 | 9.4 |
| 42 | 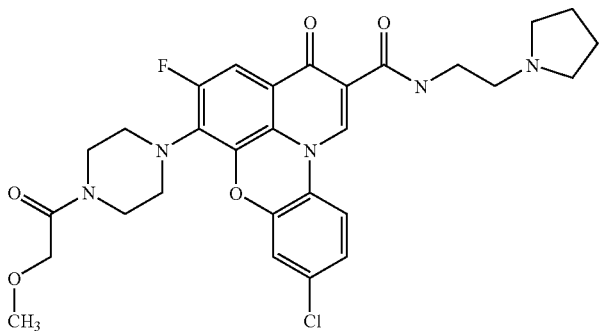 | 10 |
| 43 | 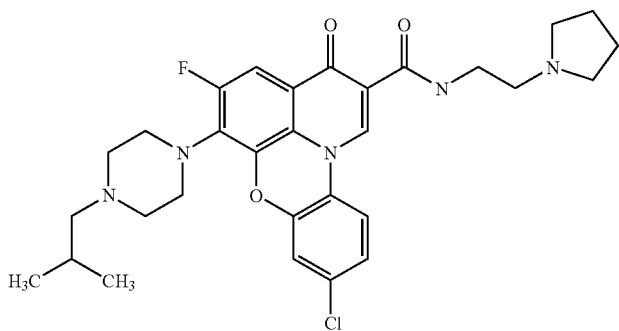 | 7.5 |

| | | |
|---|---|---|
| 44 | 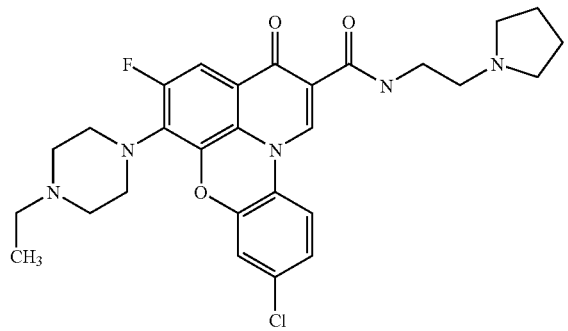 | 4.8 |
| 45 | 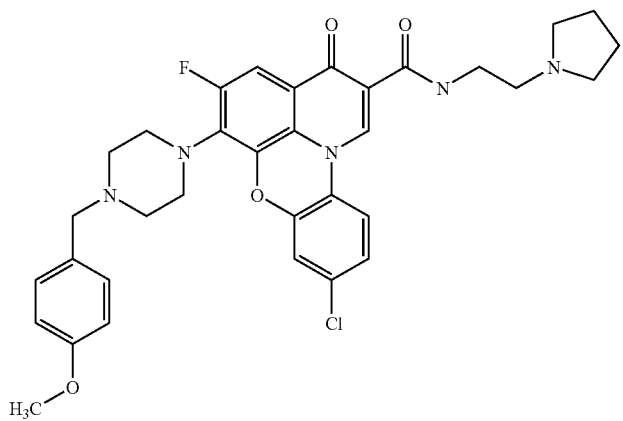 | 7.5 |
| 46 | 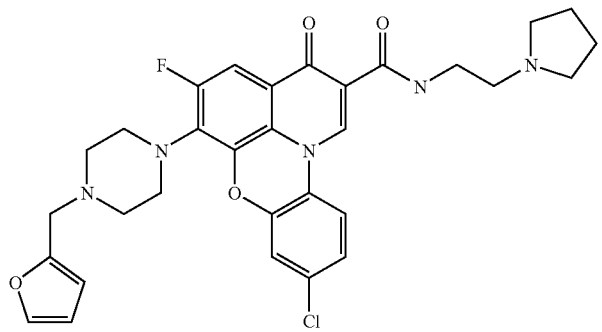 | 10 |
| 47 | 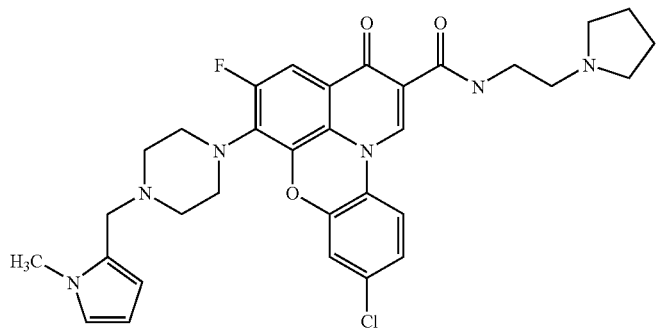 | 8.6 |

48

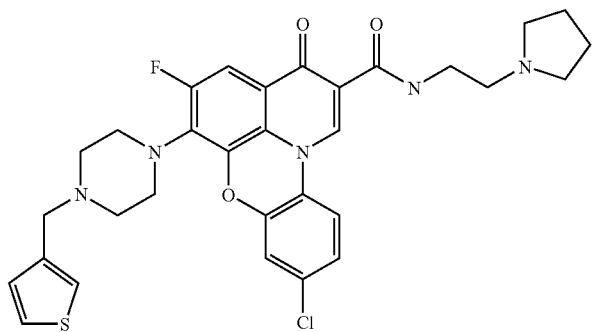

9.8

49

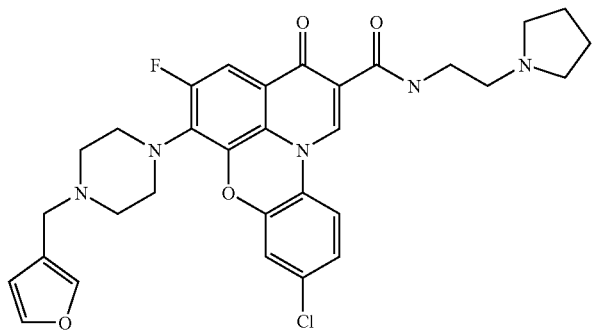

10

50

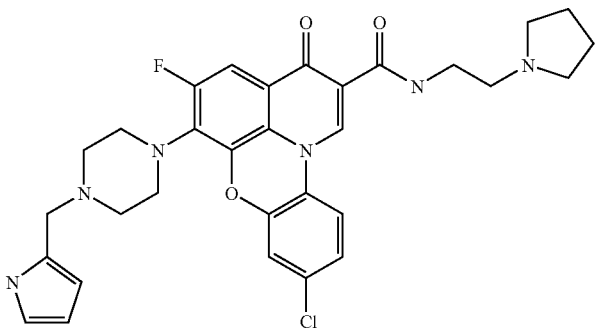

10

The compounds may be chiral or achiral. As used herein, a chiral compound is a compound that is different from its mirror image, and has an enantiomer. Methods of synthesizing chiral compounds and resolving a racemic mixture of enantiomers are well known to those skilled in the art. See, e.g., March, "*Advanced Organic Chemistry*," John Wiley and Sons, Inc., New York, (1985), which is incorporated herein by reference.

Furthermore, the present invention provides pharmaceutical compositions comprising compounds having formula 1, 1A, 2 or 3. For example, the pharmaceutical composition may comprise a compound having formula 1, 1A, 2 or 3, polyethylene glycol, and propylene glycol in a buffer solution.

The compounds described herein may interact with regions of DNA that can form quadruplexes. Because regions of DNA that can form quadruplexes are regulators of biological processes such as oncogene transcription, modulators of quadruplex biological activity can be utilized as cancer therapeutics. Molecules that interact with regions of DNA that can form quadruplexes can exert a therapeutic effect on certain cell proliferative disorders and related conditions. Particularly, abnormally increased oncogene expression can cause cell proliferative disorders, and quadruplex structures typically down-regulate oncogene expression. Examples of oncogenes include but are not limited to MYC, HIF, VEGF, ABL, TGF, PDGFA, MYB, SPARC, HUMTEL, HER, VAV, RET, H-RAS, EGF, SRC, BCL1, BCL2, DHFR, HMGA, and other oncogenes known to one of skill in the art.

Molecules that bind to regions of DNA that can form quadruplexes can exert a biological effect according to different mechanisms, which include for example, stabilizing a native quadruplex structure, inhibiting conversion of a native quadruplex to duplex DNA by blocking strand cleavage, and stabilizing a native quadruplex structure having a quadruplex-destabilizing nucleotide substitution and other sequence specific interactions. Thus, compounds that bind to regions of DNA that can form quadruplexes described herein may be administered to cells, tissues, or organisms for the purpose of down-regulating oncogene transcription and thereby treating cell proliferative disorders.

Determining whether the biological activity of native DNA that can form quadruplexes is modulated in a cell, tissue, or organism can be accomplished by monitoring quadruplex biological activity. Quadruplex forming regions of DNA biological activity may be monitored in cells, tissues, or organisms, for example, by detecting a decrease or increase of gene transcription in response to contacting the quadruplex forming DNA with a molecule. Transcription can be detected by directly observing RNA transcripts or observing polypeptides translated by transcripts, which are methods well known in the art.

Molecules that interact with quadruplex forming DNA and quadruplex forming nucleic acids can be utilized to treat many cell proliferative disorders. Cell proliferative disorders include, for example, colorectal cancers and hematopoietic neoplastic disorders (i.e., diseases involving hyperplastic/neoplastic cells of hematopoietic origin such as those arising from myeloid, lymphoid or erythroid lineages, or precursor cells thereof). The diseases can arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML) (Vaickus, Crit. Rev. in *Oncol/Hemotol.* 11:267-297 (1991)). Lymphoid malignancies include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. Cell proliferative disorders also include cancers of the colorectum, breast, lung, liver, pancreas, cervical, lymph node, colon, prostate, brain, head and neck, skin, liver, kidney, and heart. Compounds that interact with regions of DNA that can form quadruplexes also can be utilized to target cancer related processes and conditions, such as increased angiogenesis, by inhibiting angiogenesis in a subject.

The present invention provides a method for reducing cell proliferation or for treating or alleviating cell proliferative disorders, comprising contacting a system having a DNA capable of forming a quadruplex with a compound having formula 1, 1A, 2 or 3. The system may be a group of cells or one or more tissues. In one embodiment, the system is a subject in need of a treatment of a cell proliferative disorder (e.g., a mammal such as a mouse, rat, monkey, or human).

The present invention also provides a method for treating or ameliorating a cancer associated with c-Myc overexpression, by administering a compound that interacts with a c-MYC quadruplex forming region to a subject in need thereof. Examples of cancers associated with c-Myc overexpression include but are not limited to colorectal cancer, prostate cancer, and pancreatic cancer. Furthermore, the present invention provides a method for inhibiting angiogenesis and optionally treating a cancer associated with angiogenesis, comprising administering a compound that interacts with a vascular endothelial growth factor (VEGF) quadruplex forming region to a subject in need thereof, thereby reducing angiogenesis and optionally treating a cancer associated with angiogenesis.

Compounds that interact with quadruplex forming regions of DNA can also be used to reduce a microbial infection, such as a viral infection. Retroviruses offer a wealth of potential targets for G-quadruplex targeted therapeutics. G-quadruplex structures have been implicated as functional elements in at least two secondary structures formed by either viral RNA or DNA in HIV, the dimer linker structure (DLS) and the central DNA flap (CDF). Additionally, DNA aptamers which are able to adopt either inter- or intramolecular quadruplex structures are able to inhibit viral replication. In one example, DNA aptamers are able to inhibit viral replication by targeting the envelope glycoprotein (putatively). In another example, DNA aptamers inhibit viral replication by targeting the HIV-integrase respectively, suggesting the involvement of native quadruplex structures in interaction with the integrase enzyme.

Dimer linker structures, which are common to all retroviruses, serve to bind two copies of the viral genome together by a non-covalent interaction between the two 5' ends of the two viral RNA sequences. The genomic dimer is stably associated with the gag protein in the mature virus particle. In the case of HIV, the origin of this non-covalent binding may be traced to a 98 base-pair sequence containing several runs of at least two consecutive guanines (e.g., the 3' for the formation of RNA dimers in vitro). An observed cation (potassium) dependence for the formation and stability of the dimer in vitro, in addition to the failure of an antisense sequence to effectively dimerize, has revealed the most likely binding structure to be an intermolecular G-quadruplex.

Prior to integration into the host genome, reverse transcribed viral DNA forms a pre-integration complex (PIC) with at least two major viral proteins, integrase and reverse transcriptase, which is subsequently transported into the nucleus. The Central DNA Flap (CDF) refers to 99-base length single-stranded tail of the +strand, occurring near the center of the viral duplex DNA, which is known to a play a role in the nuclear import of the PIC. Oligonucleotide mimics of the CDF have been shown to form intermolecular G-quadruplex structures in cell-free systems.

Thus, compounds that recognize quadruplex forming regions can be used to bind and/or stabilize the dimer linker structure and thus prevent de-coupling of the two RNA strands. Also, by binding to the quadruplex structure formed by the CDF, protein recognition and/or binding events for nuclear transport of the PIC may be disrupted. In either case, a substantial advantage can exist over other anti-viral therapeutics. Current Highly Active Anti-Retroviral Therapeutic (HAART) regimes rely on the use of combinations of drugs targeted towards the HIV protease and HIV integrase. The requirement for multi-drug regimes is to minimize the emergence of resistance, which will usually develop rapidly when agents are used in isolation. The source of such rapid resistance is the infidelity of the reverse transcriptase enzyme which makes a mutation approximately once in every 10,000 base pairs. An advantage of targeting viral quadruplex structures over protein targets is that the development of resistance is slow or is impossible. A point mutation of the target quadruplex can compromise the integrity of the quadruplex structure and lead to a non-functional copy of the virus. A single therapeutic agent based on this concept may replace the multiple drug regimes currently employed, with the concomitant benefits of reduced costs and the elimination of harmful drug/drug interactions.

The present invention provides a method for reducing a microbial titer in a system, comprising contacting a system having a native DNA quadruplex forming region with a compound having formula 1, 1A, 2 or 3. The system may be one or more cells or tissues. Examples of microbial titers include but are not limited to viral, bacterial or fungal titers. In a particular embodiment, the system is a subject in need of a treatment for a viral infection (e.g., a mammal such as a mouse, rat, monkey, or human). Examples of viral infections include infections by a hepatitis virus (e.g., hepatitis B or C), human immunodeficiency virus (HIV), rhinovirus, herpes-zoster virus (VZV), herpes simplex virus (e.g., HSV-1 or HSV-2), cytomegalovirus (CMV), vaccinia virus, influenza virus, encephalitis virus, hantavirus, arbovirus, West Nile virus, human papilloma virus (HPV), Epstein-Barr virus, and respiratory syncytial virus. The present invention also provides a method for treating HIV infection by administering a compound having formula 1, 1A, 2 or 3 to a subject in need thereof, thereby reducing the HIV infection.

Identifying Compounds that can Bind to Guadruplex Forming Regions of DNA

Compounds described herein are identified as compounds that can bind to quadruplex forming regions of DNA where a biological activity of this region, often expressed as a "signal," produced in a system containing the compound is different than the signal produced in a system not containing the compound. While background signals may be assessed each time a new molecule is probed by the assay, detecting the background signal is not required each time a new molecule is assayed.

Examples of quadruplex forming nucleic acid sequences are set forth in the following Table 2:

TABLE 2

| SEQUENCE | SEQ ID NO | ORIGIN |
|---|---|---|
| TG$_4$AG$_3$TG$_4$AG$_3$TG$_4$AAGG | 1 | CMYC |
| GGGGGGGGGGGGCGGGGCGGGGCGGGGAGGGGC | 2 | PDGFA |
| G$_8$ACGCG$_3$AGCTG$_5$AG$_3$CTTG$_4$CCAG$_3$CG$_4$CGCTTAG$_5$ | 3 | PDGFB/c-sis |
| AGGAAGGGGAGGGCCGGGGGGAGGTGGC | 4 | CABL |
| AGGGGCGGGGCGGGGCGGGGGC | 5 | RET |
| GGGAGGAAGGGGCGGGAGCGGGGC | 6 | BCL-2 |
| GGGGGCGGGGCGGGCGCAGGGGGAGGGGGC | 7 | Cyclin D1/BCL-1 |
| CGGGGCGGGGCGGGGCGGGGC | 8 | H-RAS |
| AGAGGAGGAGGAGGTCACGGAGGAGGAGGAGAAGGAGGAGGAGGAA | 9 | CMYB |
| (GGA)$_4$ | 10 | VAV |
| AGAGAAGAGGGGAGGAGGAGGAGGAGAGGAGGAGGCGC | 11 | HMGA2 |
| GGAGGGGAGGGG | 12 | CPIM |
| AGGAGAAGGAGGAGGTGGAGGAGGAGG | 13 | HER2/neu |
| AGGAGGAGGAGAATGCGAGGAGGAGGGAGGAGA | 14 | EGFR |
| GGGGCGGGCCGGGGGCGGGGTCCCGGCGGGGCGGAG | 15 | VEGF |
| CGGGAGGAGGAGGAAGGAGGAAGCGCG | 16 | CSRC |

In addition to determining whether a test molecule or test nucleic acid gives rise to a different signal, the affinity of the interaction between the nucleic acid and the compound may be quantified. $IC_{50}$, $K_d$, or $K_i$ threshold values may be compared to the measured $IC_{50}$ or $K_d$ values for each interaction, and thereby identify a test molecule as a quadruplex interacting molecule or a test nucleic acid as a quadruplex forming nucleic acid. For example, $IC_{50}$ or $K_d$ threshold values of 10 μM or less, 1 μM or less, and 100 nM or less are often utilized. In another example, threshold values of 10 nM or less, 1 nM or less, 100 pM or less, and 10 pM or less may be utilized to identify quadruplex interacting molecules and quadruplex forming nucleic acids.

Many assays are available for identifying compounds that have affinity for quadruplex forming regions of DNA. In some of these assays, the biological activity is the quadruplex nucleic acid binding to a compound and binding is measured as a signal. In other assays, the biological activity is a polymerase arresting function of a quadruplex and the degree of arrest is measured as a decrease in a signal. In certain assays, the biological activity is transcription and transcription levels can be quantified as a signal. In another assay, the biological activity is cell death and the number of cells undergoing cell death is quantified. Another assay monitors proliferation rates of cancer cells. Examples of assays are fluorescence binding assays, gel mobility shift assays (see, e.g., Jin & Pike, Mol. Endocrinol. (1996) 10:196-205), polymerase arrest assays, transcription reporter assays, cancer cell proliferation assays, and apoptosis assays (see, e.g., Amersham Biosciences (Piscataway, N.J.)), and embodiments of such assays are described hereafter. Also, topoisomerase assays can be utilized to determine whether the quadruplex interacting molecules have a topoisomerase pathway activity (see, e.g., TopoGEN, Inc. (Columbus, Ohio)).

Gel Electrophoretic Mobility Shift Assay (EMSA)

An EMSA is useful for determining whether a nucleic acid forms a quadruplex and whether a nucleotide sequence is quadruplex-destabilizing. EMSA is conducted as described previously (Jin & Pike, Mol. Endocrinol. 10: 196-205 (1996)) with minor modifications. Generally, synthetic single-stranded oligonucleotides are labeled in the 5'-terminus with T4-kinase in the presence of [γ-$^{32}$P] ATP (1,000 mCi/mmol, Amersham Life Science) and purified through a sephadex column. $^{32}$P-labeled oligonucleotides (~30,000 cpm) are then incubated with or without various concentrations of a testing compound in 20 μl of a buffer containing 10 mM Tris pH 7.5, 100 mM KCl, 5 mM dithiothreitol, 0.1 mM EDTA, 5 mM $MgCl_2$, 10% glycerol, 0.05% Nonedit P-40, and 0.1 mg/ml of poly(dI-dC) (Pharmacia). After incubation for 20 minutes at room temperature, binding reactions are loaded on a 5% polyacrylamide gel in 0.25×Tris borate-EDTA buffer (0.25× TBE, 1×TBE is 89 mM Tris-borate, pH 8.0, 1 mM EDTA). The gel is dried and each band is quantified using a phosphoimager.

DMS Methylation Protection Assay

Chemical footprinting assays are useful for assessing quadruplex structure. Quadruplex structure is assessed by determining which nucleotides in a nucleic acid are protected or unprotected from chemical modification as a result of being inaccessible or accessible, respectively, to the modifying reagent. A DMS methylation assay is an example of a chemical footprinting assay. In such an assay, bands from EMSA are isolated and subjected to DMS-induced strand cleavage. Each band of interest is excised from an electrophoretic mobility shift gel and soaked in 100 mM KCl solution (300 μl) for 6 hours at 4° C. The solutions are filtered (microcentrifuge) and 30,000 cpm (per reaction) of DNA solution is diluted further with 100 mM KCl in 0.1×TE to a total volume of 70 μl (per reaction). Following the addition of 1 μl salmon sperm DNA (0.1 μg/μl), the reaction mixture is incubated with 1 μl DMS solution (DMS:ethanol; 4:1; v:v) for a period of time. Each reaction is quenched with 18 μl of stop buffer (b-mercaptoethanol:water:NaOAc (3 M); 1:6:7; v:v:v). Following ethanol precipitation (twice) and piperidine cleavage, the reactions are separated on a preparative gel (16%) and visualized on a phosphoimager.

Polymerase Arrest Assay

An arrest assay includes a template nucleic acid, which may comprise a quadruplex forming sequence, and a primer nucleic acid which hybridizes to the template nucleic acid 5' of the quadruplex-forming sequence. The primer is extended by a polymerase (e.g., Taq polymerase), which advances from the primer along the template nucleic acid. In this assay, a quadruplex structure can block or arrest the advance of the enzyme, leading to shorter transcription fragments. Also, the arrest assay may be conducted at a variety of temperatures, including 45° C. and 60° C., and at a variety of ion concentrations.

An example of the Taq polymerase stop assay is described in Han, et al., *Nuci. Acids Res.* (1999) 27:537-542, which is a modification of that used by Weitzmann, et al., *J. Biol. Chem.* (1996) 271:20958-20964. Briefly, a reaction mixture of template DNA (50 nM), Tris.HCl (50 mM), $MgCl_2$ (10 mM), DTT (0.5 mM), EDTA (0.1 mM), BSA (60 ng), and 5'-end-labeled quadruplex nucleic acid (~18 nM) is heated to 90° C. for 5 minutes and allowed to cool to ambient temperature over 30 minutes. Taq Polymerase (1 μl) is added to the reaction mixture, and the reaction is maintained at a constant temperature for 30 minutes. Following the addition of 10 μl stop buffer (formamide (20 ml), 1 M NaOH (200 μl), 0.5 M EDTA (400 μl), and 10 mg bromophenol blue), the reactions are separated on a preparative gel (12%) and visualized on a phosphoimager. Adenine sequencing (indicated by "A" at the top of the gel) is performed using double-stranded DNA Cycle Sequencing System from Life Technologies. The general sequence for the template strands is TCCAACTATG-TATAC (SEQ ID NO. 19)-INSERT-TTAGCGACACG-CAATTGCTATAGTGAGTCGTATTA (SEQ ID NO.20), where "INSERT" refers to a nucleic acid sequence comprising a quadruplex forming sequence (See e.g., Table 2). Bands on the gel that exhibit slower mobility are indicative of quadruplex formation.

High Throughput Polymerase Arrest Assay

A high throughput polymerase arrest assay has been developed. The assay comprises contacting a template nucleic acid, often DNA, with a primer, which also is often DNA; contacting the primer/template complex with a compound described herein (also referred to as a "test compound"); contacting the primer/template complex with a polymerase; and separating reaction products. The assay often includes the step of denaturing the primer/template complex mixture and then renaturing the complex, which often is carried out before a test molecule is added to the system. Multiple assays often are carried out using varying concentrations of a test compound, such that an $IC_{50}$ value can be obtained, for example. The reaction products often include extended primers of different lengths. Where a test compound does not significantly interact with a quadruplex structure in the template, the primer often is extended to the end of the template.

Where a test compound significantly interacts with a quadruplex structure in the template, the primer often is extended only to the quadruplex structure in the template and no further. Thus, the reaction mixture often includes at least two reaction products when a test compound interacts with a quadruplex structure in the template, one having a completely extended primer and one having an incompletely extended primer, and these two reaction products are separated. The products may be separated using any convenient separation method, such as mass spectrometry and in one embodiment, capillary electrophoresis.

The reaction products often are identified by detecting a detectable label linked to the primer. The detectable label may be non-covalently linked to the 5' end of the primer (e.g., a biotin molecule covalently linked to the 5' end of the primer which is non-covalently linked to an avidin molecule joined to a detectable label). The detectable label may be joined to the primer at any stage of the assay, sometimes before the primer is added to the system, after the primer is extended, or after the products are separated. The detectable label often is covalently linked to the primer using a procedure selected based upon the nature of the chemical groups in the detectable label.

Many methods for covalently linking detectable labels to nucleic acids are available, such as chemically coupling an allylamine-derivatized nucleotide to a succinimidyl-ester derivative of a detectable label, and then generating a primer using the labeled nucleotide. (See, e.g., *Nature Biotech* (2000) 18:345-348 and http address info.med.yale.edu/genetics/ward/tavi/n_coupling.html). A spacer (often between 5-16 carbon atoms long) sometimes is incorporated between the detectable label and the nucleotide. Any convenient detectable label may be utilized, including but not limited to a radioactive isotope (e.g., $^{125}I$, $^{131}I$, $^{35}S$, $^{32}P$, $^{14}C$ or $^{3}H$); a light scattering label (e.g., a spherical gold or silver label; Genicon Sciences Corporation, San Diego, Calif. and U.S. Pat. No. 6,214,560); an enzymic or protein label (e.g., GFP or peroxidase); or another chromogenic label or dye sometimes is utilized. Often, a fluorescent label is utilized (e.g., aminomethyl coumarin (AMCA); diethyl aminomethyl coumarin (DEAC); cascade blue (CB); fluorescein isothiocyanate (FITC); Oregon green (OG); Alexa 488 (A488); rhodamine green (RGr); lanthanide chelate (e.g., europium), carboxyrhodamine 6G (R6G); tetramethyl rhodamine (TAMRA); Texas Red (TxR); Cy3; Cy3.5; Cy5, Cy5.5 and carboxynaphtofluorescein (CNF), digoxigenin (DIG); and 2,4-dinitrophenyl (DNP)). Other fluorophores and attendant excitation and emission wavelengths are described in Anantha, et al., *Biochemistry* (1998) 37:2709-2714 and Qu & Chaires, *Methods Enzymol* (2000) 321:353-369).

In an embodiment, a primer oligonucleotide covalently linked to a fluorescent label is contacted with template DNA. The resulting complex is contacted with a test molecule and then contacted with a polymerase capable of extending the primer. The reaction products then are separated and detected by capillary electrophoresis. A longer primer sequence was used for practicing this embodiment as compared to embodiments where the primer includes no covalently-linked fluorophore or where capillary electrophoresis is not utilized for separation. Deoxynucleotides are added at any stage of the assay before the separation, often when the primer is contacted with the template DNA. The template DNA/primer complex often is denatured (e.g., by increasing the temperature of the system) and then renatured (e.g., by cooling the system) before a test compound is added).

Quadruplex Binding Assay

Generally, a 5'-fluorescent-labeled (FAM) primer (P45, 15 nM) was mixed with template DNA (15 nM) in a Tris-HCL buffer (15 mM Tris, pH 7.5) containing 10 mM $MgCl_2$, 0.1 mM EDTA and 0.1 mM mixed deoxynucleotide triphosphates (dNTP's). In one example, the FAM-P45 primer (5'-6FAM-AGTCTGACTGACTGTACGTAGCTAATAC- GACTCACTATAG CAATT-3') (SEQ ID NO. 17) and the c-Myc template DNA (5'-TCCAACTATGTATACTGGGG AGGGTGGGGAGGGTGGGGAAGGTTAGC-GACACGCAATTGCTATAGTGAGTCGTATT AGCTACG-TACAGTCAGTCAGACT-3') (SEQ ID NO. 18) were synthesized and HPLC purified by Applied Biosystems. The mixture was denatured at 95° C. for 5 minutes and, after cooling down to room temperature, was incubated at 37° C. for 15 minutes.

After cooling down to room temperature, 1 mM $KCl_2$ and the test compound (various concentrations) were added and the mixture incubated for 15 minutes at room temperature. The primer extension was performed by adding 10 mM KCl and Taq DNA Polymerase (2.5 U/reaction, Promega) and incubating at 70° C. for 30 minutes. The reaction was stopped by adding 1 µl of the reaction mixture to 10 µl Hi-Di Formamide mixed and 0.25 µl LIZ120 size standard. Hi-Di Formamide and LIZ120 size standard were purchased from Applied Biosystems. The partially extended quadruplex arrest product was between 61 or 62 bases long and the full-length extended product was 99 bases long. The products were separated and analyzed using capillary electrophoresis. Capillary electrophoresis was performed using an ABI PRISM 3100-Avant Genetic Analyzer. The assay was performed using compounds described above, and µM concentrations reported in Table 1 (Tables 1A-1F) are concentrations at which 50% of the DNA was arrested in the assay (i.e., the ratio of shorter partially extended DNA (arrested DNA) to full-length extended DNA is 1:1).

Transcription Reporter Assay

In a transcription reporter assay, test quadruplex DNA is coupled to a reporter system, such that a formation or stabilization of a quadruplex structure can modulate a reporter signal. An example of such a system is a reporter expression system in which a polypeptide, such as luciferase or green fluorescent protein (GFP), is expressed by a gene operably linked to the potential quadruplex forming nucleic acid and expression of the polypeptide can be detected. As used herein, the term "operably linked" refers to a nucleotide sequence which is regulated by a sequence comprising the potential quadruplex forming nucleic acid. A sequence may be operably linked when it is on the same nucleic acid as the quadruplex DNA, or on a different nucleic acid. An exemplary luciferase reporter system is described herein.

A luciferase promoter assay described in He, et al., *Science* (1998) 281:1509-1512 often is utilized for the study of quadruplex formation. Specifically, a vector utilized for the assay is set forth in reference 11 of the He, et al., document. In this assay, HeLa cells are transfected using the lipofectamin 2000-based system (Invitrogen) according to the manufacturer's protocol, using 0.1 µg of pRL-TK (*Renilla* luciferase reporter plasmid) and 0.9 µg of the quadruplex-forming plasmid. Firefly and *Renilla* luciferase activities are assayed using the Dual Luciferase Reporter Assay System (Promega) in a 96-well plate format according to the manufacturer's protocol.

Circular Dichroism Assay

Circular dichroism (CD) is utilized to determine whether another molecule interacts with a quadruplex nucleic acid. CD is particularly useful for determining whether a PNA or PNA-peptide conjugate hybridizes with a quadruplex nucleic acid in vitro. PNA probes are added to quadruplex DNA (5 µM each) in a buffer containing 10 mM potassium phosphate (pH 7.2) and 10 or 250 mM KCl at 37° C. and then allowed to stand for 5 minutes at the same temperature before recording spectra. CD spectra are recorded on a Jasco J-715 spectropolarimeter equipped with a thermoelectrically controlled single cell holder. CD intensity normally is detected between 220 nm and 320 nm and comparative spectra for quadruplex DNA alone, PNA alone, and quadruplex DNA with PNA are generated to determine the presence or absence of an interaction (see, e.g., Datta, et al., JACS (2001) 123:9612-9619). Spectra are arranged to represent the average of eight scans recorded at 100 nm/min.

Fluorescence Binding Assay

An example of a fluorescence binding assay is a system that includes a quadruplex nucleic acid, a signal molecule, and a test molecule. The signal molecule generates a fluorescent signal when bound to the quadruplex nucleic acid (e.g., N-methylmesoporphyrin IX (NMM)), and the signal is altered when a test compound competes with the signal molecule for binding to the quadruplex nucleic acid. An alteration in the signal when test molecule is present as compared to when test compound is not present identifies the test compound as a quadruplex interacting compound.

50 µl of quadruplex nucleic acid or a nucleic acid not capable of forming a quadruplex is added in 96-well plate. A test compound also is added in varying concentrations. A typical assay is carried out in 100 µl of 20 mM HEPES buffer, pH 7.0, 140 mM NaCl, and 100 mM KCl. 50 µl of the signal molecule NMM then is added for a final concentration of 3 µM. NMM is obtained from Frontier Scientific Inc, Logan, Utah. Fluorescence is measured at an excitation wavelength of 420 nm and an emission wavelength of 660 nm using a FluroStar 2000 fluorometer (BMG Labtechnologies, Durham, N.C.). Fluorescence often is plotted as a function of concentration of the test compound or quadruplex-targeted nucleic acid and maximum fluorescent signals for NMM are assessed in the absence of these molecules.

Cell Proliferation Assay

In a cancer cell proliferation assay, cell proliferation rates are assessed as a function of different concentrations of test compounds added to the cell culture medium. Any cancer cell type can be utilized in the assay. In one embodiment, colon cancer cells are cultured in vitro and test compounds are added to the culture medium at varying concentrations. A useful colon cancer cell line is colo320, which is a colon adenocarcinoma cell line deposited with the National Institutes of Health as accession number JCRB0225. Parameters for using such cells are available at the http address cellbank.nihs.gojp/cell/data/jcrb0225.htm.

Formulation of Compounds

As used herein, the term "pharmaceutically acceptable salts, esters and amides" includes but are not limited to carboxylate salts, amino acid addition salts, esters and amides of the compounds, as well as the zwitterionic forms thereof, which are known to those skilled in the art as suitable for use with humans and animals. (See, e.g., Gerge, S. M., et al., "Pharmaceutical Salts," *J. Pharm. Sci.* (1977) 66:1-19, which is incorporated herein by reference.)

Any suitable formulation of the compounds described herein can be prepared. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art. For example, pharmaceutically acceptable salts may be obtained by reacting a sufficiently basic compound such as an amine with a suitable acid affording a physiologically acceptable anion. Alkali metal (e.g., sodium, potassium or lithium) or alkaline earth metal (e.g., calcium) salts of carboxylic acids also are made.

A compound may be formulated as a pharmaceutical composition and administered to a mammalian host in need of such treatment. In one embodiment, the mammalian host is human. Any suitable route of administration may be used, including but not limited to oral, parenteral, intravenous, intramuscular, topical and subcutaneous routes.

In one embodiment, a compound is administered systemically (e.g., orally) in combination with a pharmaceutically acceptable vehicle such as an inert diluent or an assimilable edible carrier. They may be enclosed in hard or soft shell gelatin capsules, compressed into tablets, or incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may be varied and may conveniently be between about 2 to about 60% of the weight of a given unit dosage form. The amount of active compound in such therapeutically useful compositions is such that an effective dosage level will be obtained.

Tablets, troches, pills, capsules, and the like also may contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form is pharmaceutically acceptable and substantially non-toxic in the amounts employed. In addition, the active compound may be incorporated into sustained-release preparations and devices.

The active compound also may be administered intravenously or intraperitoneally by infusion or injection. Solutions of the active compound or its salts may be prepared in a buffered solution, often phosphate buffered saline, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The compound is sometimes prepared as a polymatrix-containing formulation for such administration (e.g., a liposome or microsome). Liposomes are described for example in U.S. Pat. No. 5,703,055 (Felgner, et al.) and Gregoriadis, Liposome Technology vols. I to III (2nd ed. 1993).

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in liquid form. Compounds often are administered as compositions or formulations, in combination with a dermatologically acceptable carrier, which may be a solid or a liquid. Examples of useful dermatological compositions used to deliver compounds to the skin are known (see, e.g., Jacquet, et al. (U.S. Pat. No. 4,608,392), Geria (U.S. Pat. No. 4,992,478), Smith, et al. (U.S. Pat. No. 4,559,157) and Wortzman (U.S. Pat. No. 4,820,508).

Compounds may be formulated with a solid carrier, which include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Generally, the concentration of the compound in a liquid composition often is from about 0.1 wt % to about 25 wt %, sometimes from about 0.5 wt % to about 10 wt %. The concentration in a semi-solid or solid composition such as a gel or a powder often is about 0.1 wt % to about 5 wt %, sometimes about 0.5 wt % to about 2.5 wt %. A compound composition may be prepared as a unit dosage form, which is prepared according to conventional techniques known in the pharmaceutical industry. In general terms, such techniques include bringing a compound into association with pharmaceutical carrier(s) and/or excipient(s) in liquid form or finely divided solid form, or both, and then shaping the product if required.

Table 3 shows various formulations which may be used with compounds described herein. For example, a compound may be formulated having dosages from 10 mg/mL to 20 mg/mL solution, using the formulations herein. In Table 3, the designation "D5W" refers to deionized water with 5% dextrose. Each component in each formulation may be varied without affecting the activity of the compound. In one example, the compound is formulated in a solution comprising polyethylene glycol and propylene glycol in a buffer solution such as a phosphate buffer.

humans are known to the art (see, e.g., U.S. Pat. No. 4,938,949). Such systems can be used for determining the $LD_{50}$ (the dose lethal to 50% of the population) and the $ED_{50}$ (the dose therapeutically effective in 50% of the population) of a compound. The dose ratio between a toxic and therapeutic effect is the therapeutic index and it can be expressed as the ratio $ED_{50}/LD_{50}$. The compound dosage often lies within a range of circulating concentrations for which the $ED_{50}$ is associated with little or no toxicity. The dosage may vary within this range depending upon the dosage form employed and the route of administration utilized. For any compounds used in the methods described herein, the therapeutically effective dose can be estimated initially from cell culture assays. A dose sometimes is formulated to achieve a circulating plasma concentration range covering the $IC_{50}$ (i.e., the concentration of the test compound which achieves a half-maximal inhibition of symptoms) as determined in in vitro assays, as such information often is used to more accurately determine useful doses in humans. Levels in plasma may be measured, for example, by high performance liquid chromatography.

TABLE 3

| Formulations | % (w/w) | Compound (mL) + Placebo solution (mL) | pH of the Placebo solution | pH of the formulated solution (10 mg/mL) |
|---|---|---|---|---|
| 1. Mannitol | 4 | 35 ml + 35 mL | 6.1 | 6.1 |
| Sucrose | 0.5 | | | |
| 5% D5W solution | 95.5 | | | |
| 2. Mannitol | 4 | 35 ml + 35 mL | 6 | 5.8 |
| 50 mM $PO_4$ buffer, pH = 6.0 | 96 | | | |
| 3. Mannitol | 4 | 35 ml + 35 mL | 5 | 5 |
| 50 mM Citrate buffer, pH = 5.0 | 96 | | | |
| 4. Mannitol | 4 | 35 ml + 35 mL | 6 | 6 |
| 5% D5W | 96 | | | |
| 5. Test compound (20 mg/mL) | 1 | 35 ml + 35 mL | 6.4 | 6.1 |
| 5% D5W | 99 | | | |
| 6. PEG 300 | 7 | 5 ml + 5 mL | N/A | 5.80 |
| Propylene glycol | 9 | | | |
| 5% D5W | 84 | | | |
| 7. PEG 300 | 7 | 5 ml + 5 mL | N/A | 5.8 |
| Propylene glycol | 9 | | | |
| 50 mM $PO_4$ buffer, pH = 6.0 | 84 | | | |
| 8. Mannitol | 4 | 5 ml + 5 mL | N/A | 5.7 |
| PEG 300 | 20 | | | |
| 50 mM $PO_4$ buffer, pH = 6.0 | 76 | | | |
| 9. Mannitol | 4 | 5 ml + 5 mL | N/A | 5.8 |
| Propylene glycol | 10 | | | |
| 50 mM $PO_4$ buffer, pH = 6.0 | 86 | | | |

The compound composition may be formulated into any dosage form, such as tablets, capsules, gel capsules, liquid syrups, soft gels, suppositories, and enemas. The compositions also may be formulated as suspensions in aqueous, non-aqueous, or mixed media. Aqueous suspensions may further contain substances which increase viscosity, including for example, sodium carboxymethylcellulose, sorbitol, and/or dextran. The suspension may also contain one or more stabilizers.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

Dosages

A useful compound dosage often is determined by assessing its in vitro activity in a cell or tissue system and/or in vivo activity in an animal system. For example, methods for extrapolating an effective dosage in mice and other animals to Another example of effective dose determination for a subject is the ability to directly assay levels of "free" and "bound" compound in the serum of the test subject. Such assays may utilize antibody mimics and/or "biosensors" generated by molecular imprinting techniques. The compound is used as a template, or "imprinting molecule", to spatially organize polymerizable monomers prior to their polymerization with catalytic reagents. Subsequent removal of the imprinted molecule leaves a polymer matrix which contains a repeated "negative image" of the compound and is able to selectively rebind the molecule under biological assay conditions (see, e.g., Ansell, et al., *Current Opinion in Biotechnology* (1996) 7:89-94 and in Shea, *Trends in Polymer Science* (1994) 2:166-173).

Such "imprinted" affinity matrixes are amenable to ligand-binding assays, whereby the immobilized monoclonal antibody component is replaced by an appropriately imprinted matrix (see, e.g., Vlatakis, et al., *Nature* (1993) 361:645-647). Through the use of isotope-labeling, "free" concentration of compound can be readily monitored and used in calculations of $IC_{50}$. Such "imprinted" affinity matrixes can also be designed to include fluorescent groups whose photon-emitting properties measurably change upon local and selective binding of compound. These changes can be readily assayed in real time using appropriate fiberoptic devices, in turn allowing the dose in a test subject to be quickly optimized based on its individual $IC_{50}$. An example of such a "biosensor" is discussed in Kriz, et al., *Analytical Chemistry* (1995) 67:2142-2144.

Exemplary doses include milligram or microgram amounts of the compound per kilogram of subject or sample weight, for example, about 1 microgram per kilogram to about 500 milligrams per kilogram, about 100 micrograms per kilogram to about 5 milligrams per kilogram, or about 1 microgram per kilogram to about 50 micrograms per kilogram. It is understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid described herein, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The following examples are offered to illustrate but not to limit the invention.

EXAMPLES

The following are exemplary procedures for synthesizing substituted quinobenzoxazines analogs.

Example 1

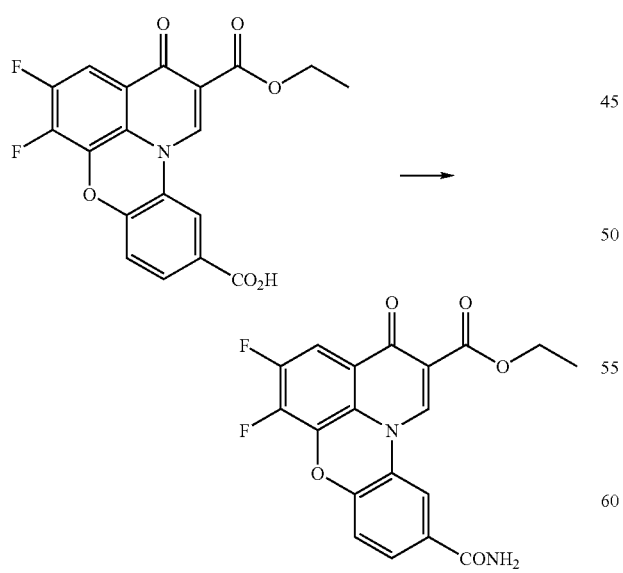

Phenoxazine carboxylic acid (655 mg, 0.846 mmol) was suspended in NMP (5 ml) and diisopropylethylamine (0.22 ml, 1.26 mmol). HBTU (481 mg, 1.268 mmol) was then added whilst maintaining the temperature below 10° C. After stirring for 1 h anhydrous ammonia gas was bubbled into the reaction for approximately 20 mins. The reaction was then stirred overnight, followed by quenching with water. The resulting mixture was extracted with dichloromethane (3×50 ml) which was dried and evaporated to yield the amide (300 mg, 42%).

Example 2

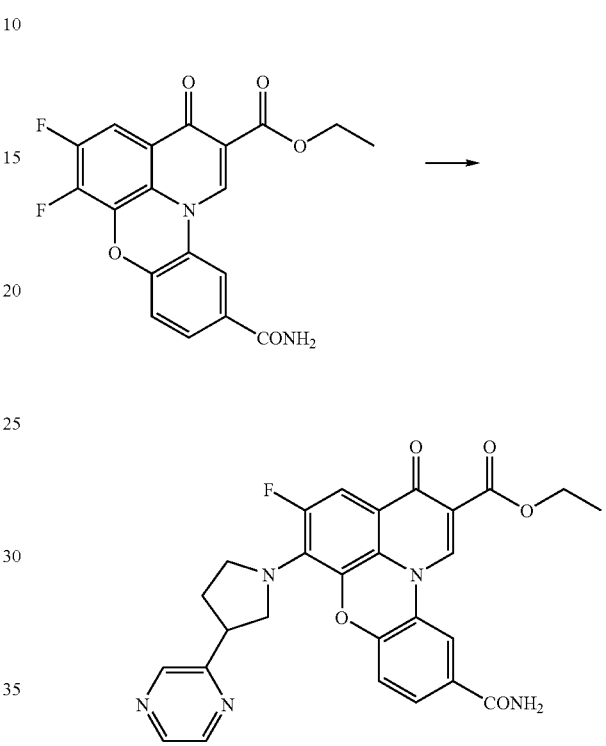

The amide (283 mg, 0.738 mmol) was suspended in anhydrous NMP and diisopropylethylamine (0.19 ml, 1.2 mmol) was added. 2-Pyrazinepyrrolidine (165 mg, 1.1 mmol) was then added and the reaction heated at 100° C. for 5 h. A further 230 mg of 2-pyrazinepyrrolidine was then added and the reaction heated and stirred overnight. Addition of water to the reaction yielded a crude solid that was further purified by flash chromatography ($SiO_2$, 2% MeOH in dichloromethane) to yield 54 mg of the pyrazine amide.

Example 3

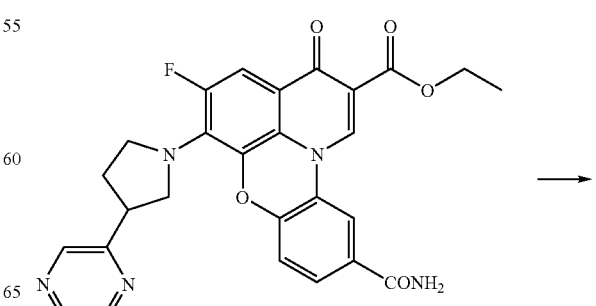

-continued

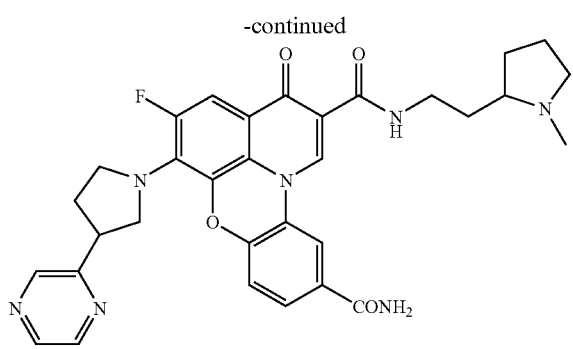

The pyrazine substituted annulated phenoxazine (53 mg, 0.1028 mmol), 2-aminoethylpyrrolidine (132 mg, 1.03 mmol) and aluminum chloride (51 mg, 0.255 mmol) were added to dichloromethane (1 ml) and stirred at room temperature under argon for 3 h. The mixture was then evaporated to a residue and was then washed with saturated aqueous sodium potassium tartaric acid. The resulting mixture was extracted with 3×10 ml dichloromethane and the extracts dried (Na$_2$SO$_4$) and evaporated. The compound was then isolated using preparative thin layer chromatography (Al$_2$O$_3$, 3% MeOH in dichloromethane) to yield the pyrazine pyrrolidine amide (30 mg, 50%) as a yellow solid.

Example 4

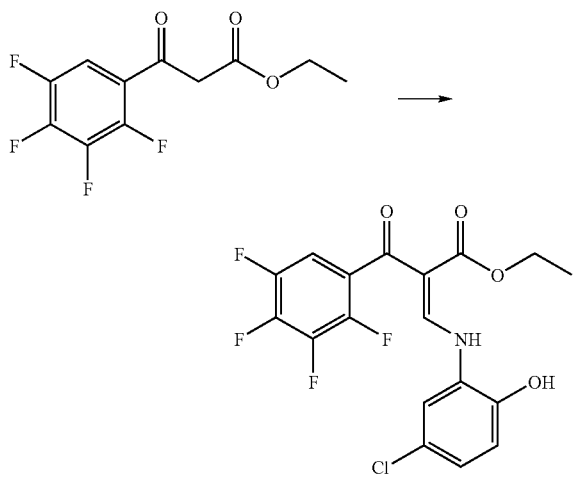

To a 250 mL roundbottom flask was added the tetrafluoroketoester (20.0 g, 75.8 mmol), triethylorthoformate (17.2 mL, 113.6 mmol) and acetic anhydride (14.3 mL, 151.6 mmol) and the reaction mixture was heated to 145° C. for 2 hours. The reaction was allowed to cool to room temperature and placed on high vacuum (ca 0.5 mm Hg) for 1 hour. The resulting oil was dissolved in ethanol (200 mL) and 2-amino-4-chlorophenol (12.0 g, 83.4 mmol) was added at room temperature and the solution became briefly clear and then product began to precipitate. The reaction was allowed to stir for 4 hours and was then filtered and washed with ethanol (200 mL) to afford the enamine as a yellow solid (22.0 g, 52.8 mmol).

Example 5

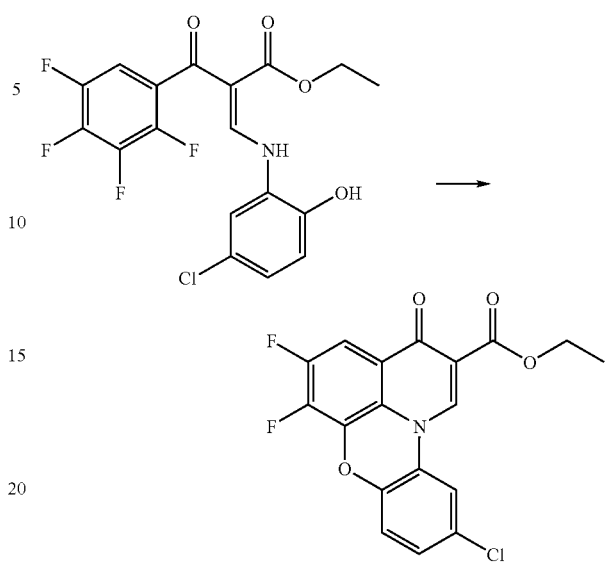

To a solution of the enamine (22.0 g, 52.8 mmol) in dry DMF (100 mL) was added potassium carbonate (8.4 g, 60.7 mmol) and the mixture was heated to 120° C., with constant stirring, for 2 hours. The mixture was allowed to cool to room temperature without stirring and was allowed to remain at room temperature for an additional hour. The crystalline solid was collected by filtration, washing with water. Recrystallization from THF afforded the difluoroester as a white crystalline solid (20.71 g).

Example 6

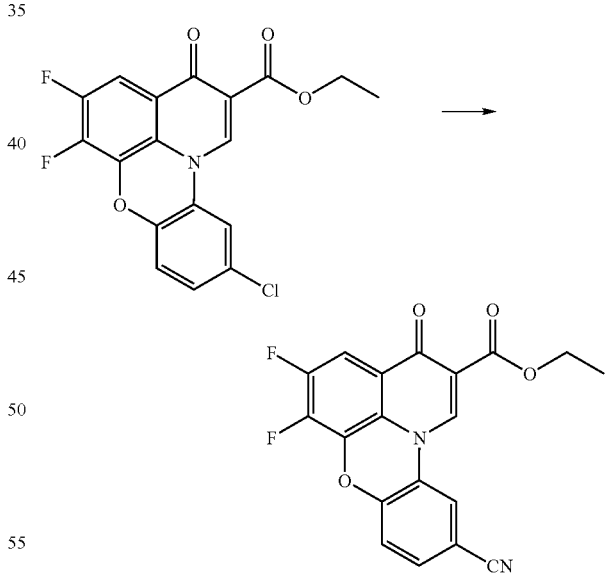

Difluoroester (244 mg, 0.646 mmol) in anhydrous dimethylacetamide (2 ml) was freeze thawed under nitrogen and then zinc powder (200 mesh, 10 mg, 0.153 mg) and zinc cyanide (46 mg, 0.392 mmol) added, followed by Pd$_2$(DBA)$_3$ (10 mg). The reaction was stirred for 16 h and then a second batch of zinc (10 mg) and zinc cyanide (46 mg) was then added. The resulting mixture was heated to 160° C. for 6 h. The reaction was then cooled, diluted with ethyl acetate and filtered through a celite pad. Evaporation of the ethyl acetate followed by flash chromatography (SiO$_2$, 5% MeOH in dichloromethane) yielded the nitrile (38 mg) as a brown solid.

Example 7

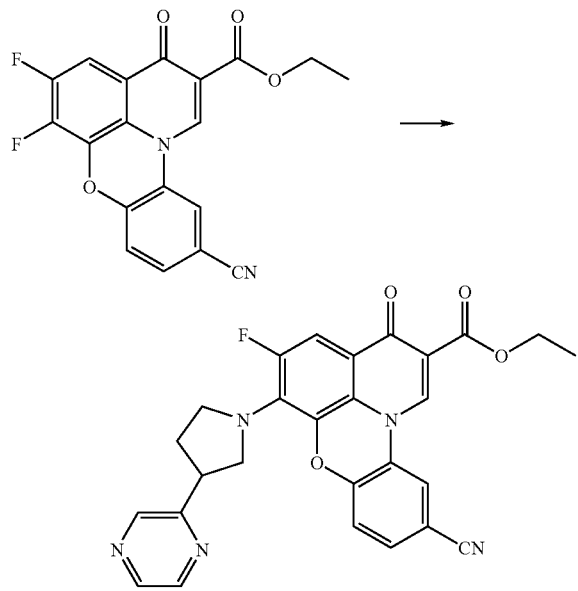

The nitrile (55 mg, 0.1423 mmol) was suspended in anhydrous NMP (1 ml) and diisopropylethylamine (0.30 ml, 0.172 mmol) added. 2-Pyrazinepyrrolidine (17 mg, 0.114 mmol) was then added and the reaction heated at 100° C. for 5 h. Addition of water yielded a crude solid that was further purified by flash chromatography (SiO$_2$, 2% MeOH) in dichloromethane to yield 25 mg of the pyrazine nitrile

Example 8

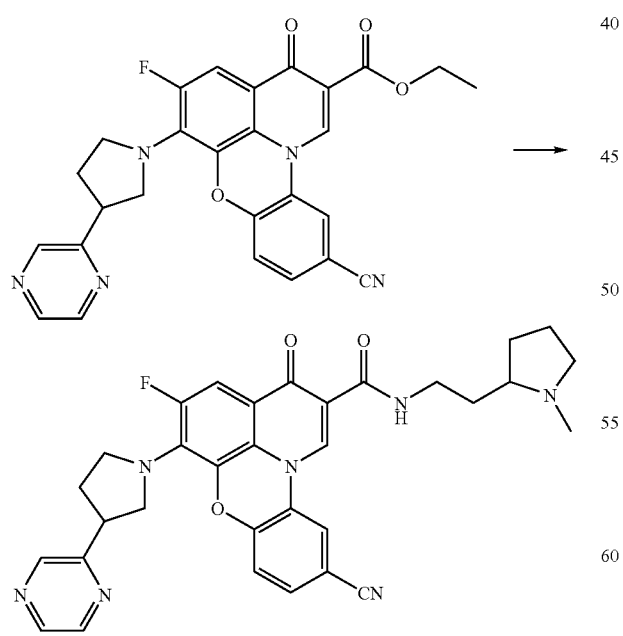

The pyrazine nitrile (94 mg, 0.19 mmol), 2-(aminoethyl)-1-methylpyrrolidine (41 uL, 0.19 mmol) and aluminum chloride (17 mg, 0.13 mmol) were added to dichloromethane (2 ml) and stirred at room temperature under argon for 16 h. The mixture was then evaporated to a residue which was washed with saturated aqueous sodium potassium tartaric acid. The mixture was then extracted with 3×10 ml dichloromethane and the extracts dried (Na$_2$SO$_4$) and evaporated. The compound was then isolated using preparative thin layer chromatography (Al$_2$O$_3$, 3% MeOH in dichloromethane) to yield the methylpyrazine nitrile 24 mg as a yellow solid.

Example 9

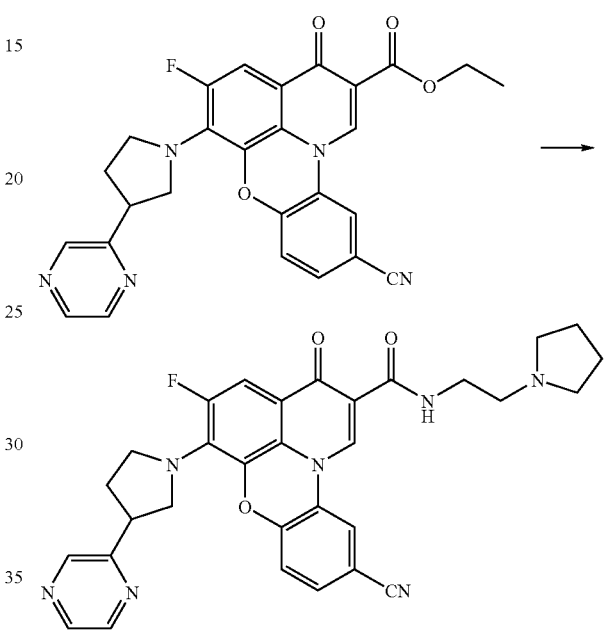

The pyrazine nitrile (91 mg, 0.18 mmol), 2-(aminoethyl) pyrrolidine (35 uL, 0.28 mmol) and aluminum chloride (37 mg, 0.28 mmol) were added to dichloromethane (2 ml) and stirred at room temperature under argon for 16 h. The mixture was then evaporated to a residue which was washed with saturated aqueous sodium potassium tartaric acid. The mixture was then extracted with dichloromethane (3×10 ml) and the extracts dried (Na$_2$SO$_4$) and evaporated.

The compound was then isolated using preparative thin layer chromatography (Al$_2$O$_3$, 3% MeOH in dichloromethane) to yield the pyrazine nitrile (48 mg) as a yellow solid.

Example 10

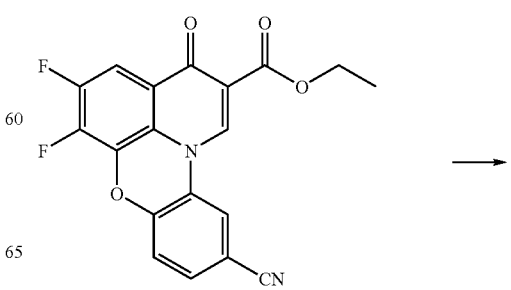

-continued

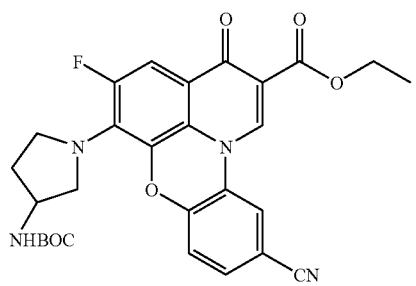

The nitrile (204 mg, 0.06 mmol) was suspended in anhydrous NMP (1 ml) and diisopropylethylamine (0.30 ml, 0.172 mmol) was added. 2-BOC aminopyrrolidine (75 mg, 0.114 mmol) was then added and the reaction heated at 100° C. for 5 h. Addition of water yielded a crude solid that was further purified by flash chromatography (SiO₂, 2% MeOH) in dichloromethane to yield 125 mg of the BOC nitrile.

Example 11

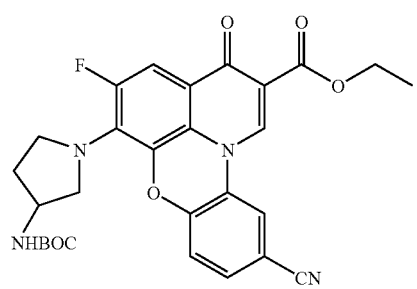

The BOC nitrile (132 mg, 0.18 mmol), 2-morpholinoethylamine (50 uL, 0.28 mmol) and aluminum chloride (37 mg, 0.28 mmol) were added to dichloromethane (2 ml) and stirred at room temperature under argon for 16 h. The mixture was then evaporated to a residue which was washed with saturated aqueous sodium potassium tartaric acid. The mixture was then extracted with 3×10 ml dichloromethane and the extracts dried (Na₂SO₄) and evaporated. The mixture was the dissolved in trifluoroacetic acid (0.5 ml), stirred for 0.5 h then blown to a residue. The compound was then isolated using preparative thin layer chromatography (Al₂O₃, 3% MeOH in dichloromethane) to yield the aminopyrrolidine nitrile (48 mg) as a yellow solid.

Example 12

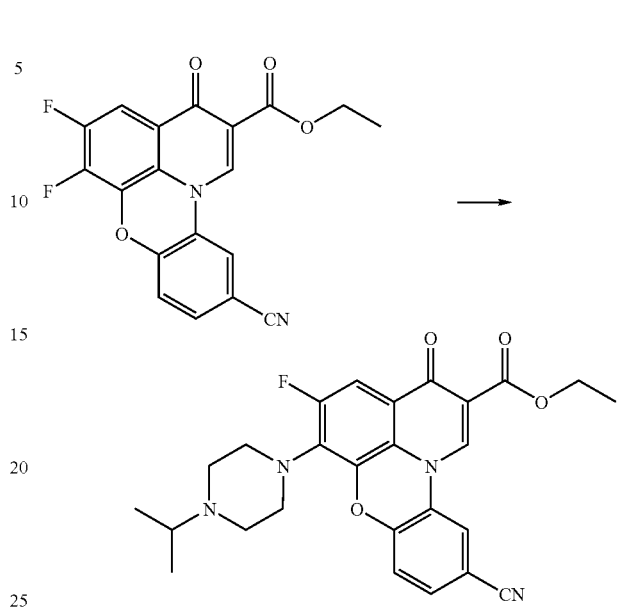

The nitrile (204 mg, 0.06 mmol) was suspended in anhydrous NMP (1 ml) and diisopropylethylamine (0.30 ml, 0.172 mmol) was added. 2-Isopropylpiperidine (75 mg, 0.114 mmol) was then added and the reaction heated at 100° C. for 5 h. Addition of water yielded a crude solid that was further purified by flash chromatography (SiO₂, 2% MeOH) in dichloromethane to yield 155 mg of the isopropyl nitrile.

Example 13

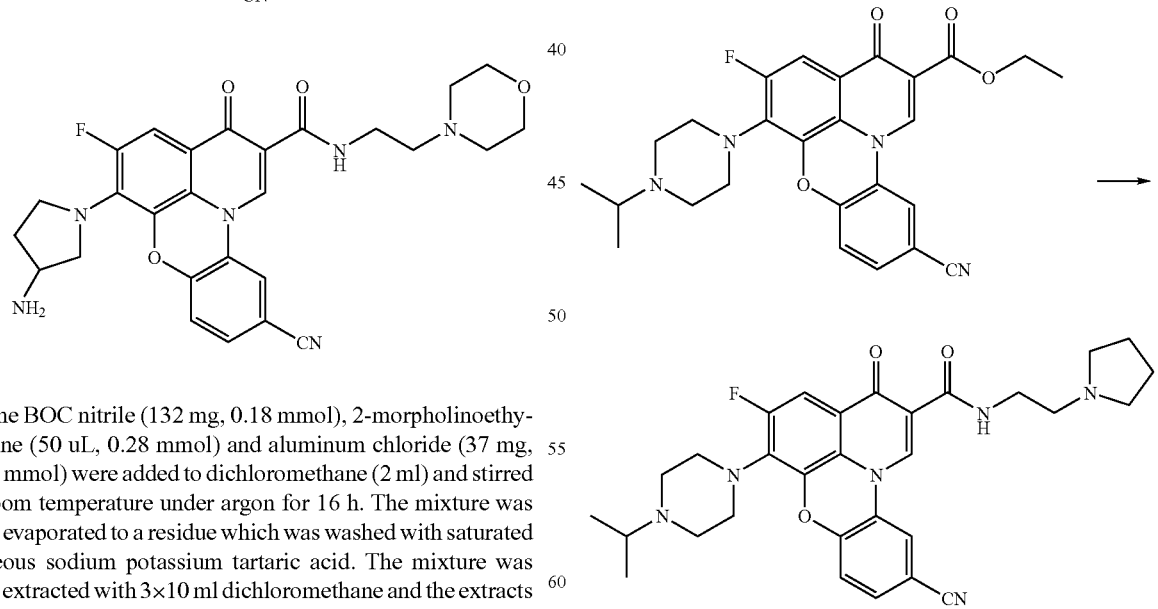

The isopropyl nitrile (126 mg, 0.18 mmol), 2-(aminoethyl) pyrrolidine (35 uL, 0.28 mmol) and aluminum chloride (37 mg, 0.28 mmol) were added to dichloromethane (2 ml) and stirred at room temperature under argon for 16 h. The mixture was then evaporated to a residue which was washed with saturated aqueous sodium potassium tartaric acid. The mixture was then extracted with 3×10 ml dichloromethane and the extracts dried (Na₂SO₄) and evaporated.

The compound was then isolated using preparative thin layer chromatography (Al₂O₃, 3% MeOH in dichloromethane) to yield the isopropyl pyrrolidine nitrile, 76 mg as a yellow solid.

Example 14

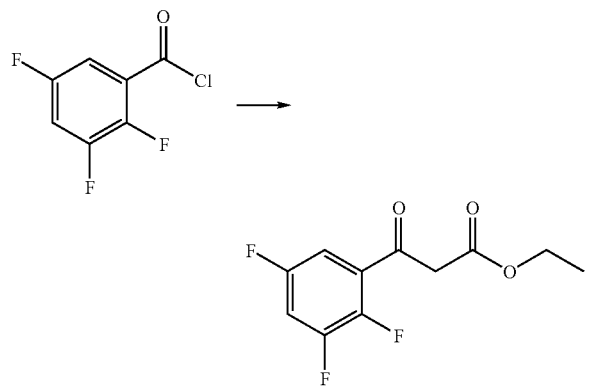

Ethylmalonate potassium salt (9.94 g, 58 mmol) was suspended in acetonitrile, under argon, and cooled with stirring to 5° C. Magnesium chloride (7.58 g, 79.6 mmol) was then added in portions, maintaining the temperature between 5-10° C., and stirred for a further 0.5 h before 2,3,4-trifluorobenzoyl chloride (10.33 g, 53.1 mmol) in acetonitrile (20 ml) was added. The reaction was then stirred for a further 5 mins. and triethylamine (14.8 ml, 106 mmol) was added dropwise, so as to maintain a temperature of 5-10° C. The reaction was then allowed to warm to room temperature and stirred for a further two hours before quenching with 2M HCl (175 ml). The resulting mixture was extracted with toluene (2×250 ml) and the extracts were then evaporated to yield the keto ester (12.79 g, 98%) which was used without further purification.

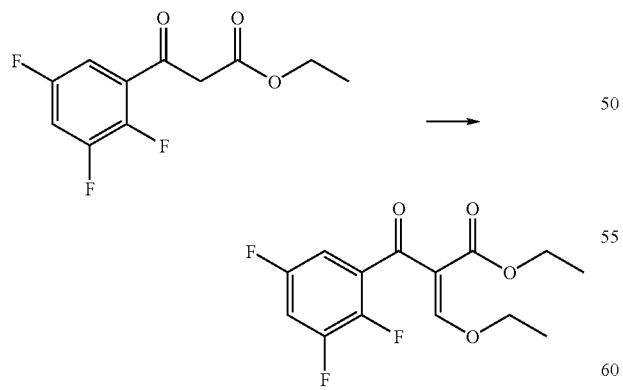

Crude keto ester (5.3 g, 21.5 mmol), triethylorthoformate (5.4 ml, 32.5 mmol) and acetic anhydride (4.1 ml, 43.4 mmol) were mixed and heated to reflux for 2 h. The reaction was then cooled and evaporated to yield the vinyl ether as a viscous oil (6.55 g, 100%) which was approximately 80% pure.

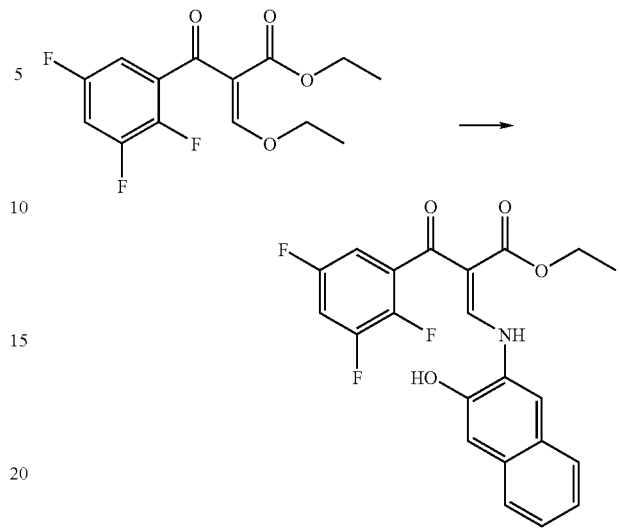

The vinyl ether (6.45 g, 21.34 mmol) and 3-amino-2-napthol (3.09 g, 19.41 mmol) were mixed in ethanol (20 ml and stirred at room temperature for 40 minutes. The resulting mixture was filtered and the solid washed with EtOH to yield the enamine as a greenish brown solid (5.52 g, 68% yield) that was approximately 90% pure.

Example 15

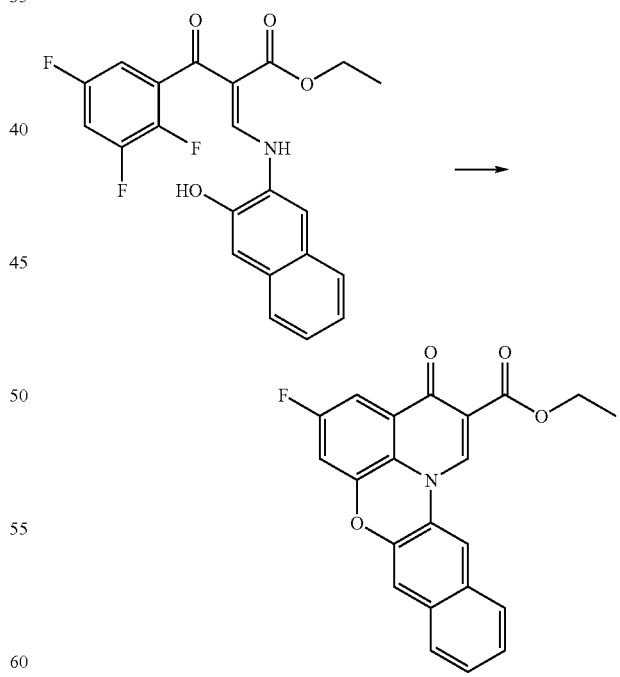

The enamine (3.112 g, 7.49 mmol)) was added to DMF (15 ml) and potassium carbonate (1.24 g, 8.97 mmol) and stirred and heated to 100° C. for 5 hr. Upon cooling the annulated phenoxazine crystallized out of the reaction mixture. The reaction was filtered and the solid was washed with water (50

Example 16

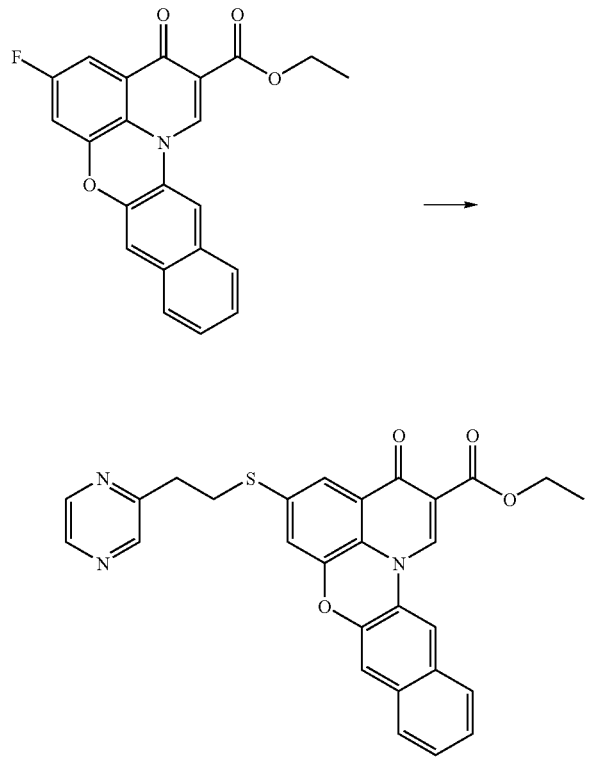

2-Pyrazine-ethanol (0.35 ml, 2.85 mmol), annulated phenoxazine (214 mg, 0.57 mmol), potassium carbonate (158 mg, 1.143 mmol) and NMP (1 ml) were mixed and heated at 100° C. for 1 h. The reaction was then quenched in water and stirred overnight which yielded a crude solid. Flash chromatography of the solid (SiO2, 2% MeOH in Dichloromethane) yielded 91 mg (32%) of the pyrazine substituted annulated phenoxazine as a yellow solid.

Example 17

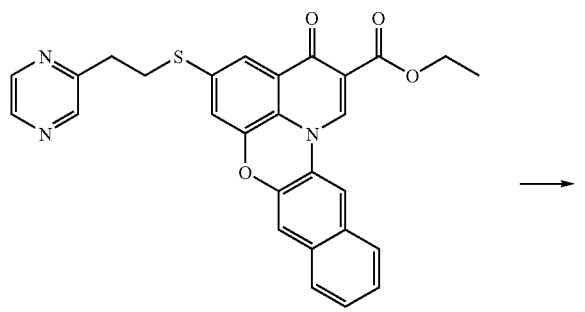

-continued

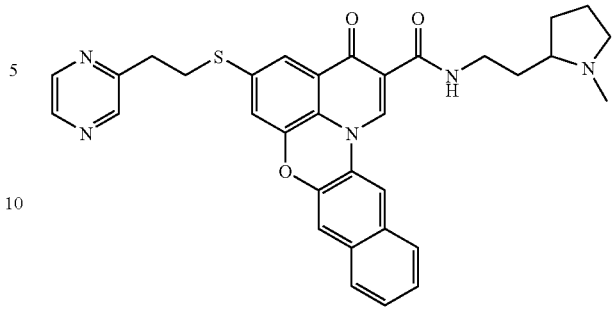

The pyrazine substituted annulated phenoxazine (43 mg, 0.08677 mmol), 2-(aminoethyl)-1-methlypyrrolidine (20 uL, 0.138 mmol) and aluminum chloride (17 mg, 0.13 mmol) were added to dichloromethane (1 ml) and stirred at room temperature under argon for 16 h. A further 20 mg of aluminum chloride was then added and the mixture stirred for a further 6 h. The mixture was then evaporated to a residue which was washed with saturated aqueous sodium potassium tartaric acid. The mixture was then extracted with 3×10 ml dichloromethane and the extracts dried (Na$_2$SO$_4$) and evaporated. The compound was then isolated using preparative thin layer chromatography (Al$_2$O$_3$, 3% MeOH in dichloromethane) to yield the pyrazine methylpyrrolidine (20 mg, 40%) as a yellow solid.

Example 18

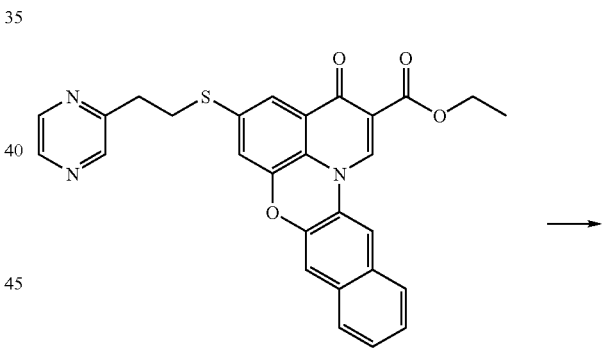

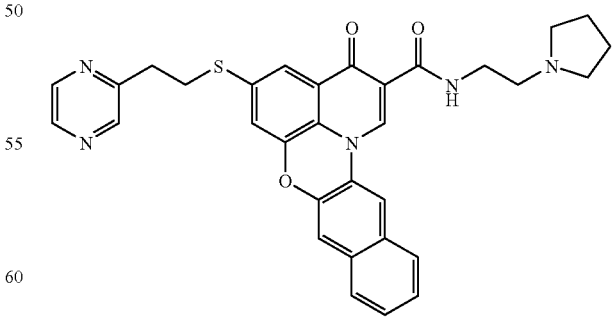

The pyrazine substituted annulated phenoxazine (37 mg, 0.07466 mmol), 2-aminoethylpyrrolidine (15 uL, 0.118 mmol) and aluminum chloride (20 mg, 0.15 mmol) were added to dichloromethane (1 ml) and stirred at room temperature under argon for 16 h. The mixture was then evaporated to a residue which was washed with saturated aqueous sodium potassium tartaric acid. The mixture was then extracted with 3×10 ml dichloromethane and the extracts dried (Na₂SO₄) and evaporated. The compound was then isolated using preparative thin layer chromatography (Al₂O₃, 3% MeOH in dichloromethane) to yield the pyrazine pyrrolidine (21 mg, 50%) as a yellow solid.

Example 19

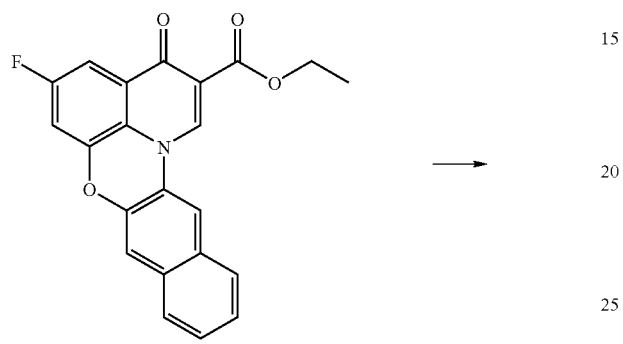

The annulated phenoxazine (218 mg, 0.581 mmol) 2-pyrazine ethanol (0.5 ml, 4.07 mmol), potassium carbonate (400 mg, 2.9 mmol) in 1 ml of anhydrous NMP were mixed and heated for 5.5 h at 100° C. The reaction was then quenched in water and extracted with dichloromethane (3×10 ml). The extract was evaporated and purified by flash chromatography (SiO₂, 1% MeOH in dichloromethane) to yield 24 mg (11%) of the thiol as a yellow solid.

Example 20

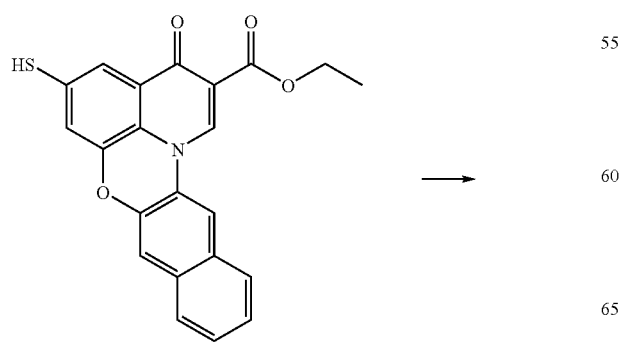

-continued

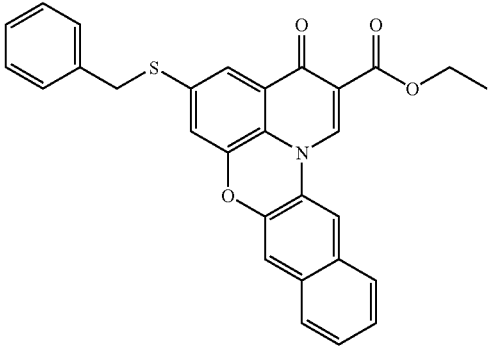

The thiol (21 mg, 0.054 mmol), benzyl bromide (8 uL, 0.07 mmol) and triethylamine (10 ul, 0.072 mmol) were added to anhydrous dichloromethane (1.5 ml) and stirred for 6 h at room temperature. The mixture was then quenched with water, and the organics extracted with dichloromethane (3×10 ml) and evaporated to a residue. Preparative thin layer chromatography (SiO₂, 1% MeOH in dichloromethane) yielded the benzyl phenoxazine (20 mg, 80%) as a yellow solid.

Example 21

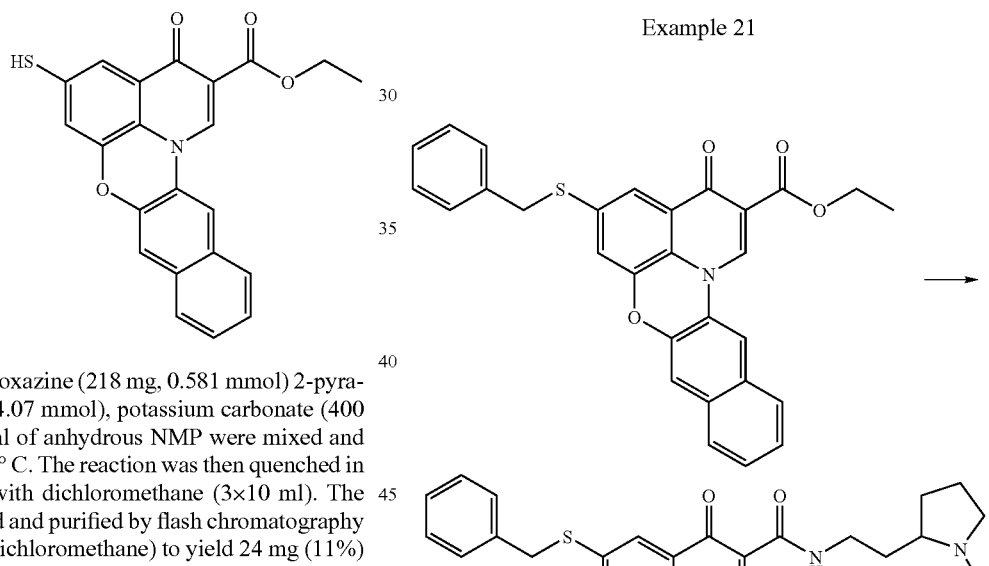

Benzyl phenoxazine (20 mg, 0.0417 mmol), 2-(2-aminoethyl)-1-methylpyrrolidine (12 ul, 0.083 mmol) and aluminum chloride (11 mg, 0.0825 mmol) were mixed in anhydrous dichloromethane (1 ml) and stirred for 1 h. The mixture was then evaporated to a residue which was washed with saturated aqueous sodium potassium tartaric acid. The mixture was then extracted with 3×10 ml dichloromethane and the extracts dried (Na₂SO₄) and evaporated. The compound was isolated using preparative thin layer chromatography

Example 22

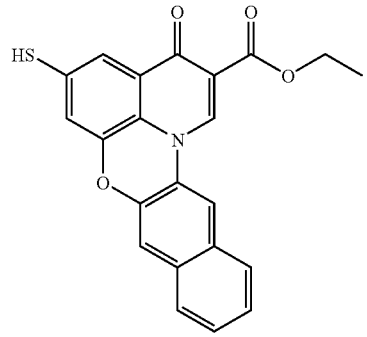

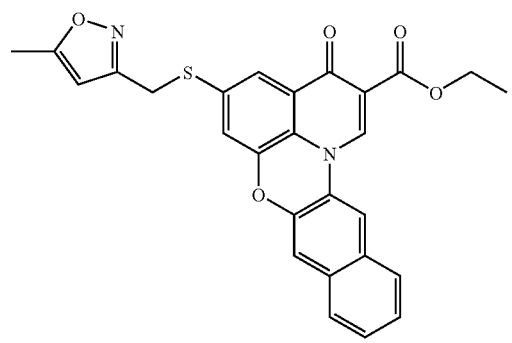

The thiol (35 mg, 0.09 mmol), 3-(chloromethyl)-5-methylisoxazole (14 mg, 0.106 mmol) and triethylamine (5 ul, 0.1076 mmol) were added to anhydrous dichloromethane (1.5 ml) and stirred for 6 h at room temperature. The mixture was quenched with water, the organics extracted with dichloromethane (3×10 ml) and evaporated to a residue. Preparative thin layer chromatography (SiO2, 1% MeOH in dichloromethane) yielded the isoxazole phenoxazine (19 mg, 37%) as a yellow solid.

Example 23

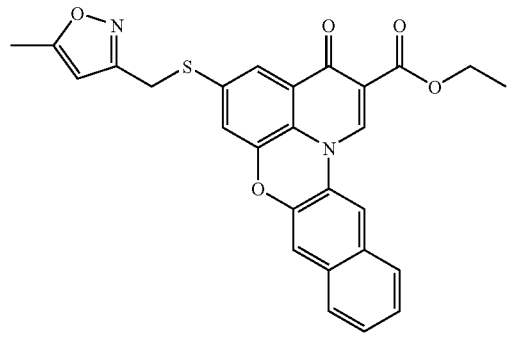

($Al_2O_3$, 3% MeOH in Dichloromethane) to yield the benzyl methylpyrrolidine (18 mg, 77%) as a yellow solid.

-continued

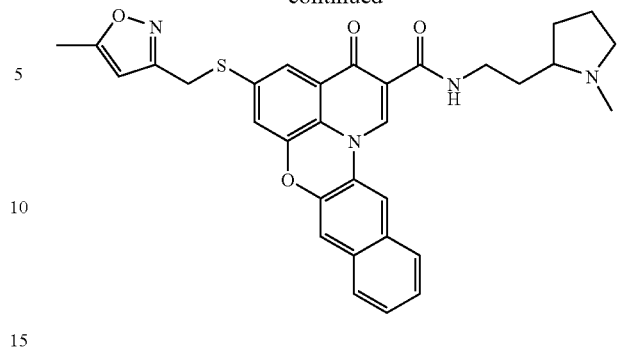

Isoxazole phenoxazine (14 mg, 0.1181 mmol), 2-(2-aminoethyl)-1-methylpyrrolidine (20 ul, 0.138 mmol) and aluminum chloride (25 mg, 0.1874 mmol) were mixed in anhydrous dichloromethane (1 ml) and stirred for 1 h. The mixture was then evaporated to a residue which was washed with saturated aqueous sodium potassium tartaric acid. The mixture was extracted with 3×10 ml dichloromethane and the extracts dried ($Na_2SO_4$) and evaporated. The compound was then isolated using preparative thin layer chromatography ($Al_2O_3$, 3% MeOH in Dichloromethane) to yield the isoxazole methylpyrrolidine (19 mg, 77%) as a yellow solid.

Example 24

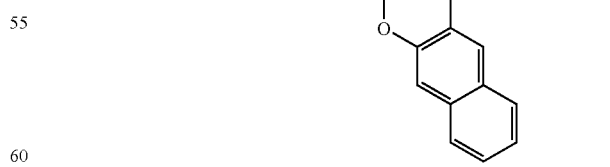

The thiol (32 mg, 0.127 mmol), 4-bromomethylpyridine hydrobromide (40 mg, 0.106 mmol) and triethylamine (32 ul, 0.2296 mmol) were added to anhydrous dichloromethane (1.5 ml) and stirred for 6 h at room temperature. The mixture was quenched with water, the organics extracted with dichloromethane (3×10 ml) and evaporated to a residue. Preparative thin layer chromatography (SiO$_2$, 1% MeOH in dichloromethane) yielded the 4-pyridinyl phenoxazine (13 mg, 22%) as a yellow solid.

Example 25

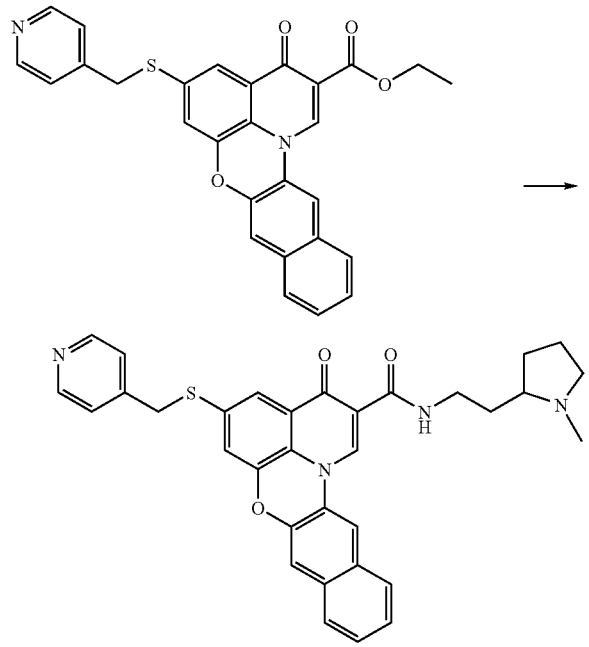

4-Pyridinyl phenoxazine (13 mg, 0.1181 mmol), 2-(2-aminoethyl)-1-methylpyrrolidine (22 ul, 0.1518 mmol) and aluminum chloride (27 mg, 0.2025 mmol) were mixed in anhydrous dichloromethane (1 ml) and stirred for 1 h. The mixture was then evaporated to a residue which was washed with saturated aqueous sodium potassium tartaric acid. The mixture was then extracted with 3×10 ml dichloromethane and the extracts dried (Na$_2$SO$_4$) and evaporated. The compound was then isolated using preparative thin layer chromatography (Al$_2$O$_3$, 3% MeOH in dichloromethane) to yield the 4-pyridinyl methylpyrrolidine (11 mg) as a yellow solid.

Example 26

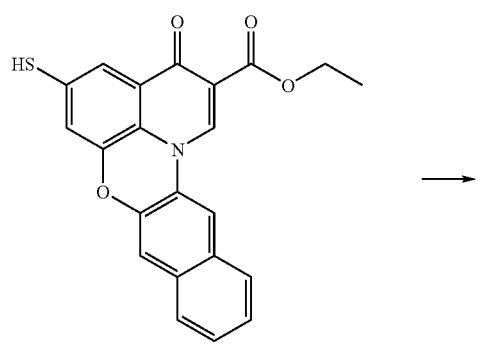

-continued

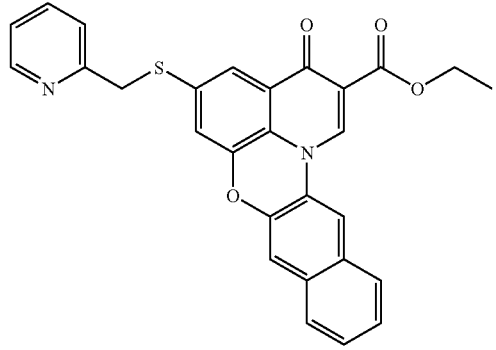

The thiol (30 mg, 0.127 mmol), 2-bromomethylpyridine hydrobromide (24 mg, 0.077 mmol) and triethylamine (24 ul, 0.179 mmol) were added to anhydrous dichloromethane (1.5 ml) and stirred for 6 h at room temperature. The mixture was quenched with water, the organics extracted with dichloromethane (3×10 ml) and evaporated to a residue. Preparative thin layer chromatography (SiO2, 1% MeOH in dichloromethane) yielded the 2-pyridinyl phenoxazine (28 mg, 69%) as a yellow solid.

Example 27

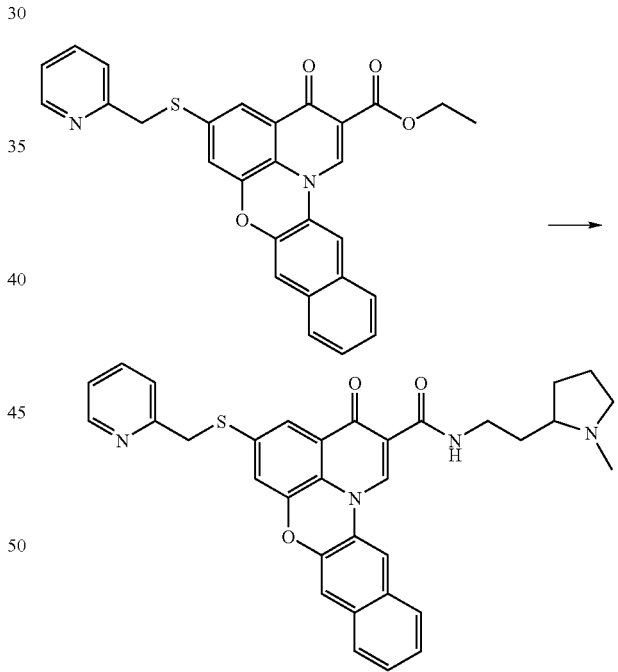

2-Pyridinyl phenoxazine (28 mg,), 2-(2-aminoethyl)-1-methylpyrrolidine (17 ul, 0.1173 mmol) and aluminum chloride (21 mg, 0.1575 mmol) were mixed in anhydrous dichloromethane (1 ml) and stirred for 1 h. The mixture was then evaporated to a residue which was washed with saturated aqueous sodium potassium tartaric acid. The mixture was then extracted with 3×10 ml dichloromethane and the extracts dried (Na$_2$SO$_4$) and evaporated. The compound was then isolated using preparative thin layer chromatography (Al$_2$O$_3$, 3% MeOH in dichloromethane) to yield the 2-pyridinyl methylpyrrolidine (17.5 mg) as a yellow solid.

Example 28

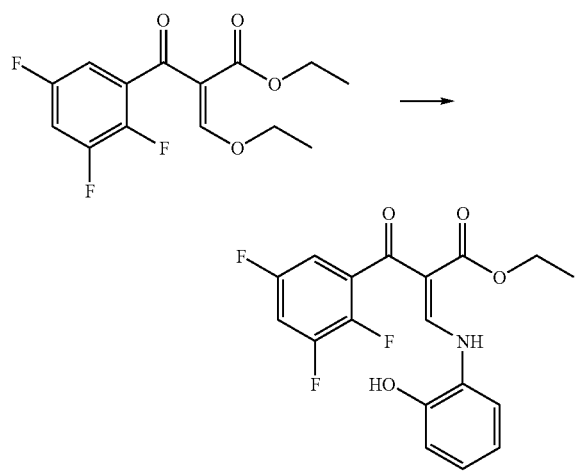

The vinyl ether (3.2 g, 10 mmol) and 3-amino-2-phenol (1.09 g, 10 mmol) were mixed in ethanol (10 ml) and stirred at room temperature. The resulting mixture was filtered and the solid washed with EtOH to yield the benzenl enamine (2.42 g, 72% yield).

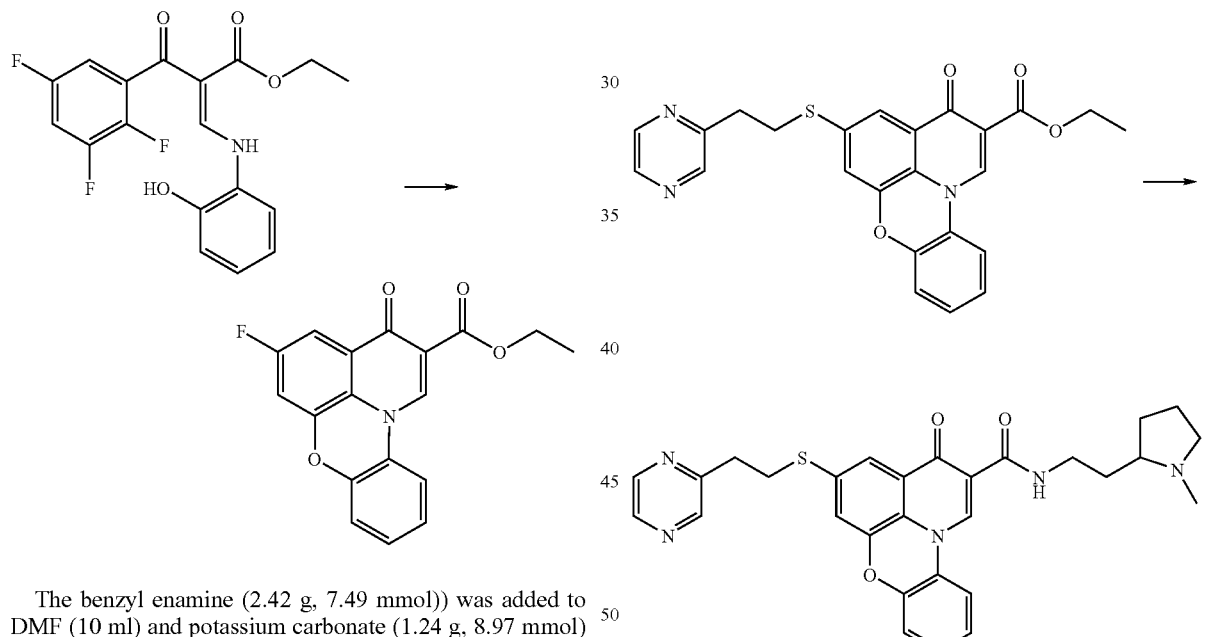

The benzyl enamine (2.42 g, 7.49 mmol)) was added to DMF (10 ml) and potassium carbonate (1.24 g, 8.97 mmol) and stirred and heated to 100° C. for 5 hr. Upon cooling the phenoxazine crystallized out of the reaction mixture (1.07 g, 63%).

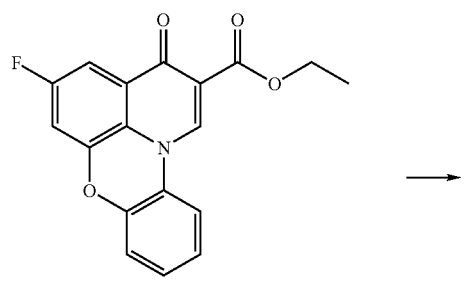

2-Pyrazine-ethanol (0.42 ml, 3.4 mmol), phenoxazine (145 mg, 0.57 mmol), potassium carbonate (158 mg, 1.143 mmol) and NMP (1 ml) were mixed and heated at 100° C. for 1 h. The reaction was then quenched in water and stirred overnight which yielded a crude solid. Flash chromatography (SiO2, 2% MeOH in Dichloromethane) yielded 182 mg (61%) of the pyrazine substituted phenoxazine as a yellow solid.

Example 29

2-Pyridinyl phenoxazine (46 mg,), 2-(2-aminoethyl)-1-methylpyrrolidine (20 ul, 0.13 mmol) and aluminum chloride (21 mg, 0.1575 mmol) were mixed in anhydrous dichloromethane (1 ml) and stirred for 1 h. The mixture was then evaporated to a residue which was washed with saturated aqueous sodium potassium tartaric acid. The mixture was then extracted with 3×10 ml dichloromethane and the extracts dried (Na$_2$SO$_4$) and evaporated. The compound was then isolated using preparative thin layer chromatography (Al$_2$O$_3$, 3% MeOH in dichloromethane) to yield the 2-pyridinyl methylpyrrollidine (25 mg) as a yellow solid.

Example 30

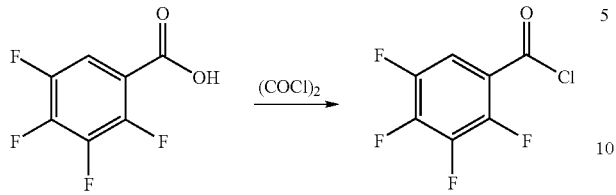

To a solution of 2,3,4,5-tetrafluorobenzoic acid (100 g, 510 mmol), in methylene chloride (0.5 L) was added oxalyl chloride (68 g, 540 mmol) and DMF (ca 3 drops) and the reaction mixture was allowed to stir at room temperature overnight allowing for the produced gasses to escape. The solvent was removed in vacuo and the vessel was placed on high vacuum (ca 0.5 mm Hg) for 2 hours to afford the acid chloride as a viscous oil (105 g) and was used in the subsequent reaction without further purification.

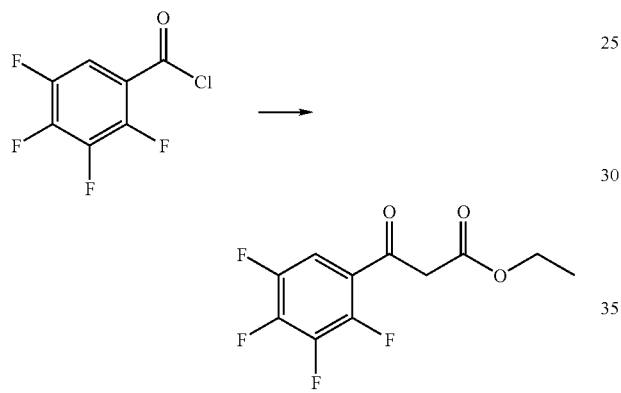

To a suspension of potassium ethyl malonate (97 g, 570 mmol) and magnesium chloride (55 g, 570 mmol) in acetonitrile and the suspension was chilled to 0° C. To this suspension was added the crude 2,3,4,5-benzoyl chloride (105 g, 520 mmol) over 5 minutes. Triethylamine was slowly added at a rate sufficient to keep the reaction temperature below 10° C. and the mixture was allowed to warm to room temperature and was stirred overnight. The solvent was removed in vacuo and replaced with toluene (300 mL) and 1N HCl (500 mL) was added and the mixture was allowed to stir for 1 hour. The organic layer was separated and washed with 1N HCl (100 mL) and brine (100 mL) and dried over sodium sulfate, filtering over a pad of silica gel (50×100 mm), eluting with ethyl acetate. The solvent was removed in vacuo and the resulting oil was dissolved in ethanol/water (9:1) and was allowed to crystallize overnight. The resulting crystals were Isolated by filtration, washing with ethanol/water (8:2) to afford the ketoester (43.75 g, 166 mmol) as a white crystalline solid.

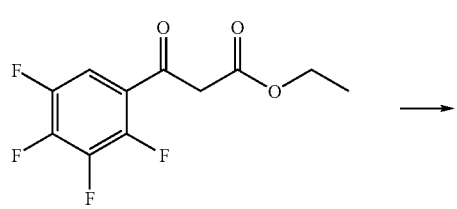

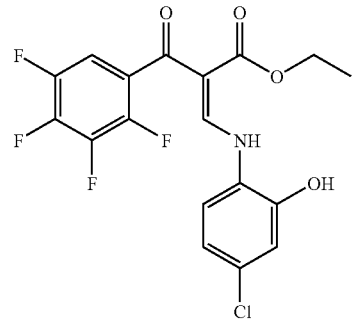

To a 250 mL roundbottom flask was added the tetrafluoroketoester (10.0 g, 37.9 mmol), triethylorthoformate (8.6 mL, 56.8 mmol) and acetic anhydride (7.15 mL, 75.8 mmol) and the reaction mixture was heated to 145° C. for 2 hours. The reaction was allowed to cool to room temperature and placed on high vacuum (ca 0.5 mm Hg) for 1 hour. The resulting oil was dissolved in ethanol (100 mL) and 2-amino-5-chlorophenol (5.98 g, 41.7 mmol) was added at room temperature and the solution became briefly clear and then product began to precipitate. The reaction was allowed to stir for 4 hours and was then filtered and washed with ethanol (100 mL) to afford the enamine as a yellow solid (12.45 g, 29.9 mmol).

Example 31

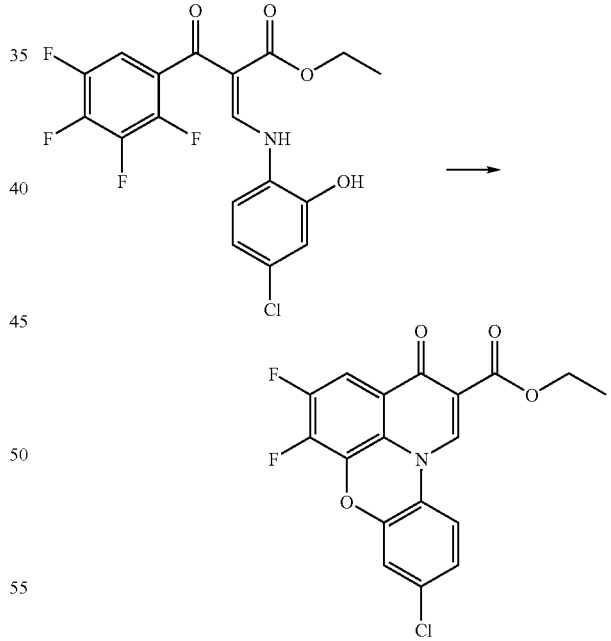

To a solution of the enamine (12.45 g, 29.9 mmol) in dry DMF (50 mL) was added potassium carbonate (4.94 g, 1.1 eq.) and the mixture was heated to 120° C., with constant stirring, for 2 hours. The mixture was allowed to cool to room temperature without stirring and was allowed to remain at room temperature for an additional hour. The crystalline solid was collected by filtration, washing with water. Recrystallization from THF afforded the difluoroester as a white crystalline solid (11.38 g).

Example 32

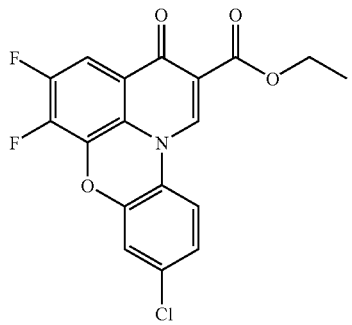 

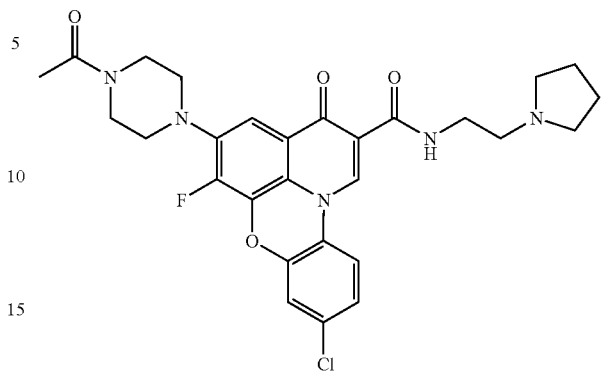

To a microwave reactor tube was added the difluoroamide (60 mg, 0.13 mmol), 1-acetylpiperazine (26 mg, 0.2 mmol) and 1-methylpyrrolidine-2-one (0.5 mL) and the mixture was treat with microwave radiation for 3 minutes (250° C.). The mixture was allowed to cool to room temperature and purified by mass-directed liquid chromatography, separating the 6-isomer (2.8 mg) from the 7-isomer (39 mg). The isolated fractions were dried in vaccuo to afford the acetylated piperazine as the TFA salt.

Example 34

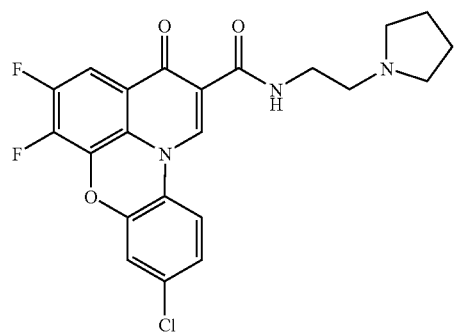

To a solution of the difluoroester (2.0 g, 5.3 mmol) in methylene chloride (10 mL) was added 1-(2-aminoethyl) pyrrolidine (0.79 g, 6.9 mmol) followed by aluminum chloride (1.05 g, 8.0 mmol). The reaction mixture was allowed to stir at room temperature for 1 hour then quenched with a concentrated solution of potassium sodium tartrate (25 mL) and 1N NaOH (10 mL), allowing stirring to continue for an additional hour. The mixture was diluted with methylene chloride (100 mL) and further extracted 3 times with methylene chloride (50 mL). The resulting organic layer was dried over sodium sulfate and concentrated in vaccuo. The resulting solid was triturated from ethyl acetate to afford the amide as a tan solid (2.0 g, 4.5 mmol).

Example 33

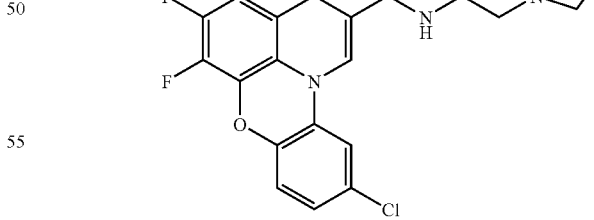

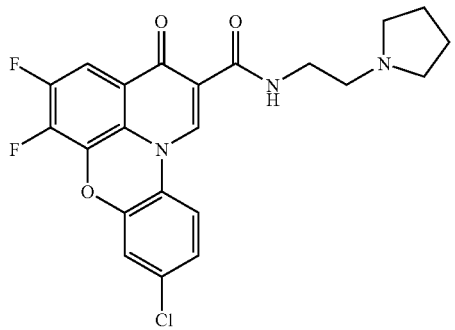 

To a solution of the difluroester (2.0 g, 5.3 mmol) in methylene chloride (10 mL) was added 1-(2-aminoethyl) pyrrolidine (0.79 g, 6.9 mmol) followed by aluminum chloride (1.05 g, 8.0 mmol). The reaction mixture was allowed to stir at room temperature for 1 hour then quenched with a concentrated solution of potassium sodium tartrate (25 mL) and 1N NaOH (10 mL), allowing stirring to continue for an additional hour. The mixture was diluted with methylene chloride (100 mL) and further extracted 3 times with methylene chloride (50 mL). The resulting organic layer was dried over sodium sulfate and concentrated in vaccuo. The resulting solid was triturated from ethyl acetate to afford the amide as a tan solid (1.85 g, 4.16 mmol).

Example 35

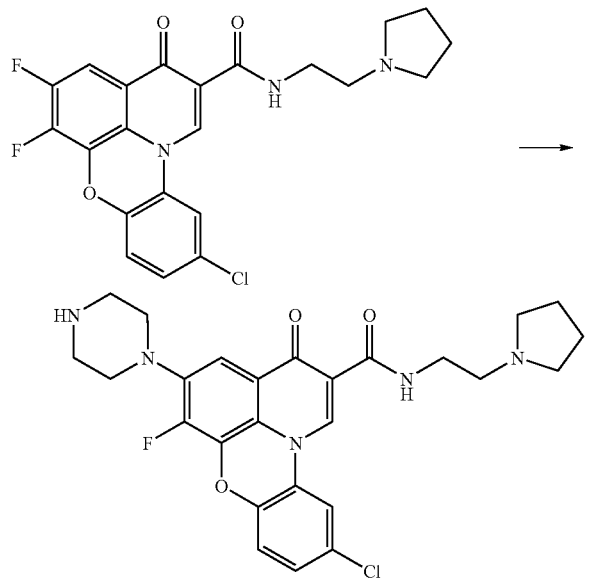

To a microwave reactor tube was added the difluoroamide (60 mg, 0.13 mmol), tert-butoxycarbonyl piperazine (38 mg, 0.2 mmol) and 1-methylpyrrolidine-2-one (0.5 mL) and the mixture was treat with microwave radiation for 3 minutes (250° C.). The mixture was allowed to cool to room temperature and purified by mass-directed liquid chromatography, separating the 6-isomer (0.8 mg) from the 7-isomer (7.9 mg). The isolated fractions were dried in vaccuo to afford the piperazine as the bis-TFA salt.

Example 36

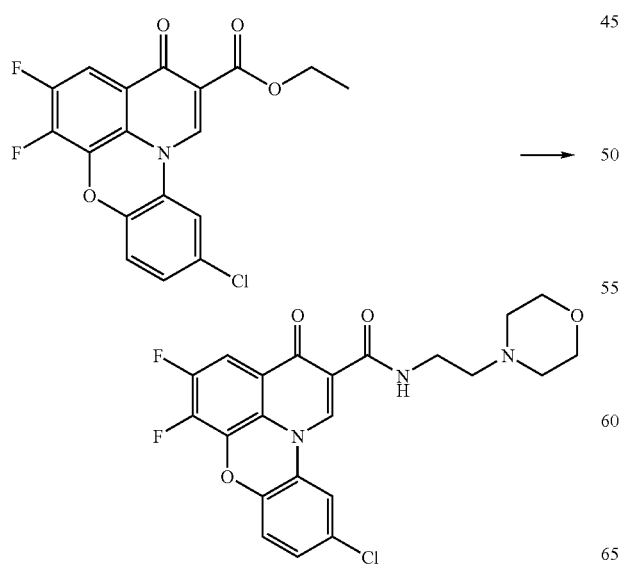

To a solution of the difluroester (2.0 g, 5.3 mmol) in methylene chloride (10 mL) was added 4-(2-aminoethyl)-morpholine (0.79 g, 6.9 mmol) followed by aluminum chloride (1.05 g, 8.0 mmol). The reaction mixture was allowed to stir at room temperature for 1 hour then quenched with a concentrated solution of potassium sodium tartrate (25 mL) and 1N NaOH (10 mL), allowing stirring to continue for an additional hour. The mixture was diluted with methylene chloride (100 mL) and further extracted 3 times with methylene chloride (50 mL). The resulting organic layer was dried over sodium sulfate and concentrated in vaccuo. The resulting solid was triturated from ethyl acetate to afford the amide as a tan solid (2.02 g, 4.38 mmol).

Example 37

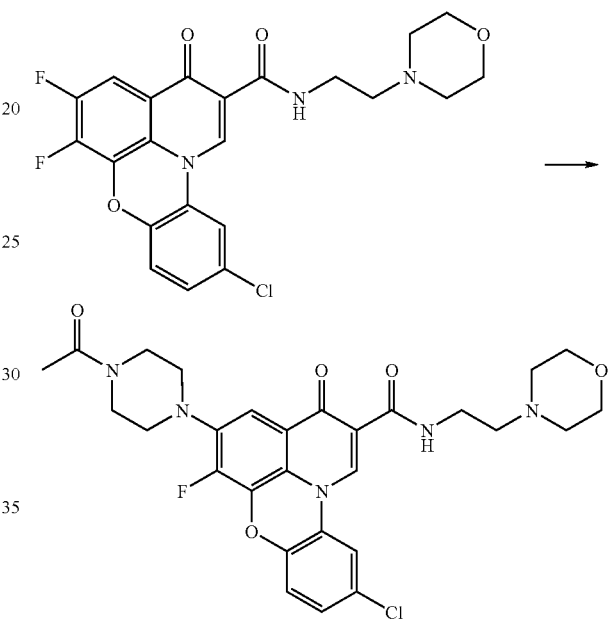

To a microwave reactor tube was added the difluoroamide (60 mg, 0.13 mmol), 1-acetylpiperazine (26 mg, 0.2 mmol) and 1-methylpyrrolidine-2-one (0.5 mL) and the mixture was treat with microwave radiation for 3 minutes (250° C.). The mixture was allowed to cool to room temperature and purified by mass-directed liquid chromatography, separating the 6-isomer (2.0 mg) from the 7-isomer (29.7 mg). The isolated fractions were dried in vaccuo to afford the acetylated piperazine as the TFA salt.

Example 38

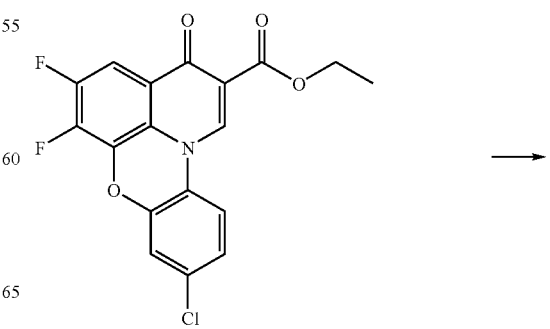

-continued

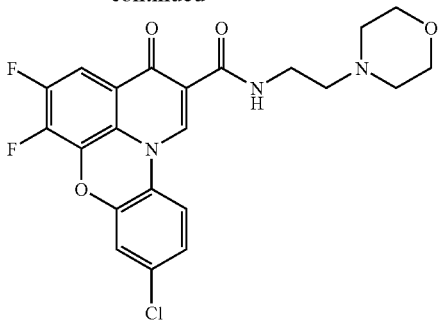

To a solution of the difluroester (2.0 g, 5.3 mmol) in methylene chloride (10 mL) was added 4-(2-aminoethyl)-morpholine (0.79 g, 6.9 mmol) followed by aluminum chloride (1.05 g, 8.0 mmol). The reaction mixture was allowed to stir at room temperature for 1 hour then quenched with a concentrated solution of potassium sodium tartrate (25 mL) and 1N NaOH (10 mL), allowing stirring to continue for an additional hour. The mixture was diluted with methylene chloride (100 mL) and further extracted 3 times with methylene chloride (50 mL). The resulting organic layer was dried over sodium sulfate and concentrated in vaccuo. The resulting solid was triturated from ethyl acetate to afford the amide as a tan solid (2.3 g, 4.99 mmol).

Example 39

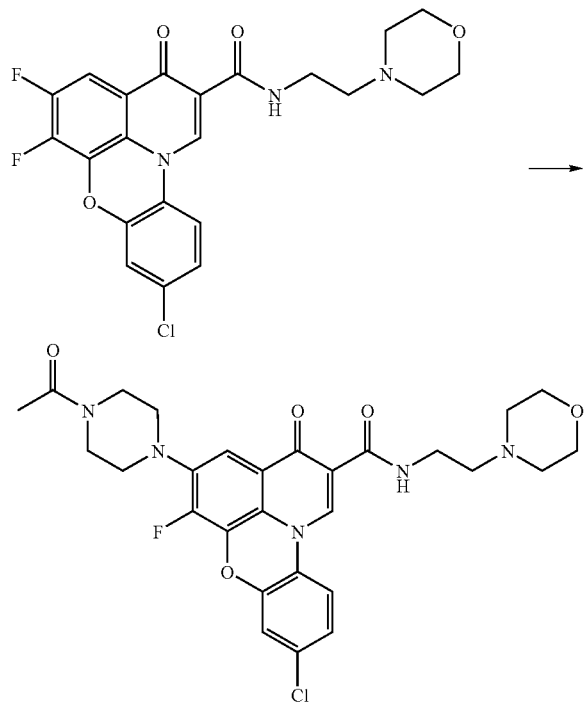

To a microwave reactor tube was added the difluoroamide (60 mg, 0.13 mmol), 1-acetylpiperazine (26 mg, 0.2 mmol) and 1-methylpyrrolidine-2-one (0.5 mL) and the mixture was treat with microwave radiation for 3 minutes (250° C.). The mixture was allowed to cool to room temperature and purified by mass-directed liquid chromatography, separating the 6-isomer (1.2 mg) from the 7-isomer (18 mg). The isolated fractions were dried in vaccuo to afford the acetylated piperazine as the TFA salt.

Example 40

Cell Proliferation and/or Cytotoxicity Assay

The antiproliferative effects of the present compounds may be tested using a cell proliferation and/or cytotoxicity assay, following protocols described below.

Cell culture. Human cervical epithelial cells (HeLa cells) are obtained from American Type Culture Collection (Manassas, Va.). Cells are grown in Eagle's minimum essential medium (MEM, Hyclone, Utah) supplemented with 2 mM Glutamine, 0.1 mM nonessential amino acid, 1 mM Na Pyruvate, 1.5 g/L $NaHCO_3$, 50 mg/L gentamicin, and 10% fetal bovine serum (Hyclone, USA) in a humidified atmosphere of 5% $CO_2$ at 37° C.

MTS assays. Antiproliferative effects of anticancer drugs are tested by the CellTiter 96 $AQ_{ueous}$ assay (Promega, Wis.), which is a colorimetric assay for determining the number of viable cells. (See, e.g., Wang, L., et al., *Methods Cell Sci* (1996) 18:249-255).

Generally, cells (2,000 to 5,000 cells/well) are seeded on 96 well flat bottom plates (Corning, N.Y.) in 100 μl of culture medium without any anticancer drug on day 0, and the culture medium is exchanged for that contained anticancer drugs at various concentrations on day 1. After incubation for 3 days under normal growth conditions (on day 4), the monolayers are washed once in PBS, and the medium is switched to 100 μl of PBS in each of the 96 well plate. After mixing MTS and PMS at the ratio of 20:1, 20 μl of MTS/PMS solution is added to each of the 96 well plate and incubated for 4 hours in a humidified atmosphere of 5% $CO_2$ at 37° C. The absorbance was read at 490 nm using FLUOstar Galaxy 96 well plate reader (BMG Labtechnologies, Germany).

Example 41

Measurement of mRNA Values in Cell Assays

Real-time quantitative PCR (QPCR) method may be used to detect the changes of the target c-myc and the endogenous reference GAPDH gene copies in the same tube. Generally, cells (15,000 cells/well) are seeded on 96 well flat bottom plates (Corning, N.Y.) and incubated under normal growth conditions for overnight. The next day, the culture medium is exchanged for that containing anticancer drugs at various concentrations and incubated for 4 hrs in a humidified atmosphere of 5% $CO_2$ at 37° C. Total RNA (tRNA) is extracted using the RNeasy 96 Kit (QIAGEN, CA). The concentration of the tRNA is determined by the RiboGreen RNA Quantitation Reagent (Molecular Probes, Oreg.).

A reverse-transcription (RT) reaction may be conducted using 50 ng of tRNA from each well in a 25 μl reaction containing 1×TaqMan RT buffer, 2.5 uM random hexamers, 5.5 mM $MgCl_2$, 0.5 mM each deoxynucleoside triphosphate (dNTP), 30 U MultiScribe Reverse Transcriptase, and 10 U RNase inhibitor. RT reactions are incubated for 10 min at 25° C., reverse-transcribed for 30 min at 48° C., inactivated for 5 min at 95° C., and placed at 4° C. All RT reagents may be purchased from Applied Biosystems, CA.

Real-Time QPCR reaction may be performed in a 50 μl reaction containing the 5 μl of cDNA, 1× Universal PCR Master Mix, 1×c-myc Pre-Developed Primers and Probe set, and 0.8×GAPDH Pre-Developed Primers and Probe set.

Because of the relative abundance of GAPDH gene in Hela, GAPDH primers and probe concentration may be adjusted to get accurate threshold cycles ($C_T$) for both genes in the same tube. The threshold cycle ($C_T$) indicates the fractional cycle number at which the amount of amplified target reaches a fixed threshold. By doing so, the GAPDH amplification is stopped before it can limit the common reactants available for amplification of the c-myc. The ΔRn value represents the normalized reporter signal minus the baseline signal. ΔRn increases during PCR as amplicon copy number increases until the reaction approaches a plateau.

The c-myc probe is labeled with 6FAM™ dye-MGB and the GAPDH probe is labeled with VIC™ dye-MGB. Preincubation is performed for 2 min at 50° C. to activate AmpErase UNG enzyme and then for 10 min at 95° C. to activate AmpliTaq DNA Polymerase. DNA is amplified for 40 cycles of 15 sec at 95° C. and 1 min at 60° C. Human c-myc and GAPDH cDNA are amplified, detected, and quantitated in real time using the ABI Prism 7000 Sequence Detection system (Applied Biosystems, CA), which is set to detect both 6-FAM and VIC reporter dyes simultaneously.

The data may be analyzed using the ABI PRISM Sequence Detection System and Microsoft Excel. Relative quantitation is done using the standard curve and comparative $C_T$ method at the same time, and both methods gave equivalent results. The cycle at which the amplification plot crosses the $C_T$ is known to accurately reflect relative mRNA values. (See, Heid, et al., *Genome Res.* (1996) 6:986-994; Gibson, et al., *Genome Res.* (1996) 6:995-1001). QPCR reactions are set up in triplicate at each cDNA sample and the triplicate $C_T$ values are averaged. All reagents including Pre-Developed Primers and probe set may be purchased from Applied Biosystems, CA.

Example 42

In Vitro Characterization

Various methods were used for in vitro characterization of the compounds of the present invention, including but not limited to i) stop assays; ii) quadruplex/duplex competition assay; iii) quadrome footprints; and iv) direct assay in the absence of a competitor molecule.

Stop Assays. Stop assays are high throughput, first-pass screens for detecting drugs that bind to and stabilize the target G-quadruplex. Generally, DNA template oligonucleotide is created, which contains the nucleotide sequence of the "target" quadruplex against which drug screening is desired. A fluorescently labeled primer DNA is then annealed to the 3' end of the template DNA. A DNA polymerase such as Taq polymerase is then introduced to synthesize a complementary strand of DNA by extending from the fluorescently labeled primer. When the progress of the Taq polymerase is unhindered, it synthesizes a full-length copy of the template. Addition of a test drug that merely binds to duplex DNA but does not bind selectively the quadruplex region results in a decrease in synthesis of full length product and a concomitant increase in variable-length DNA copies. If, however, the test drug selectively binds to and stabilizes the quadruplex, the progress of polymerase arrests only at the quadruplex, and a characteristic "Stop Product" is synthesized.

Compounds are initially screened at a single concentration, and "hits" are re-assayed over a range of doses to determine an $IC_{50}$ value (i.e., the concentration of drug required to produce an arrest product/full-length product ratio of 1:1). These products are visualized by capillary electrophoresis.

Quadruplex/Duplex Competitor Assay. The selectivity of compounds for the target quadruplex sequence relative to duplex DNA may be measured using a competition assay (i.e., "selectivity screen"). This selectivity screen uses the stop assay as a reporter system to measure the relative ability of an externally added DNA sequence to compete with the target quadruplex structure formed in the DNA template for binding of the drug. For example, the competitors are the c-myc quadruplex sequence, which is identical to the quadruplex sequence present in the template DNA; or a plasmid DNA which mimics complex genomic duplex DNA. The degree to which each competitor successfully "soaks up" drug in solution is reflected by the quantitative decrease in synthesis of the stop product. In this manner, the relative binding affinities of drug to both the target quadruplex and duplex DNA are determined.

Quadrome Footprints. Compounds may also be evaluated for their ability to bind to other native quadruplex structures of biological relevance, including quadruplex control elements that regulate a range of different oncogenes. The resulting data are used to create a Quadrome footprint.

Direct Interaction Assay. Compounds may be evaluated for their ability to interact directly with nucleic acids capable of forming a quadruplex structure, wherein the nucleic acid is not a telomeric nucleic acid. The assay may be performed in the same or different vessels. For example, a compound may be contacted with each nucleic acid in the same vessel. Alternatively, a compound may be separately contacted with each of the nucleic acids tested in a different vessel. A telomeric nucleic acid as used herein represents a region of highly repetitive nucleic acid at the end of a chromosome. As used herein, a direct interaction is measured without the presence of a competitor nucleic acid.

An interaction between the compound and the nucleic acid may be determined for example, by measuring $IC_{50}$ values, which are indicative of the binding and/or quadruplex stabilization. The selectivity of interactions may be determined, for example, by comparing measured $IC_{50}$ values. For example, the lowest $IC_{50}$ values may be used to indicate a strong interaction between the compound and the nucleic acid, while highest $IC_{50}$ values show a poor interaction; thus, showing selectivity of interaction. The reaction products may be characterized by capillary electrophoresis.

Example 43

Direct Interaction Assay

Generally, a 5'-fluorescent-labeled (FAM) primer (P45, 15 nM) is mixed with template DNA (15 nM) in a Tris-HCL buffer (15 mM Tris, pH 7.5) containing 10 mM $MgCl_2$, 0.1 mM EDTA and 0.1 mM mixed deoxynucleotide triphosphates (dNTP's). The mixture is denatured at 95° C. for 5 minutes and, after cooling down to room temperature, is incubated at 37° C. for 15 minutes. After cooling down to room temperature, 1 mM $KCl_2$ and the test compound (various concentrations) are added and the mixture incubated for 15 minutes at room temperature.

The primer extension is performed by adding 13 mM KCl and Taq DNA Polymerase (2.5 U/reaction, Promega) and incubating at 70° C. for 20 minutes. The reaction is stopped by adding 1 μl of the reaction mixture to 10 μl Hi-Di Formamide mixed and 0.25 μl LIZ120 size standard. The method is repeated with the addition of various concentrations of competitor nucleic acids at the first step, along with the primer and template sequences. The G-quadruplex binding ligand is added at the concentration previously established to produce a 1:1 ratio of stop-product to full-length product. A CC50 for each nucleic acid competitor is defined as the concentration of competitor required to change the ratio of arrest product to full-length product from 1:1 to 1:2. The nucleic acid sequences of quadruplexes that may be used for this assay are set forth in Table 4.

TABLE 4

(STOP TEMPLATES)

TGFB3-81
TATACGGGGTGGGGGAGGGAGGGATTAGCGACACGCAATTGCTATAGTGA
GTCGTATTAGCTACGTACAGTCAGTCAGACT

HRAS-85
TATACCGGGCGGGGCGGGGCGGGGCTTAGCGACACGCAATTGCTATA
GTGAGTCGTATTAGCTACGTACAGTCAGTCAGACT

BCL2-97(full)
TAGGGGCGGGCGCGGGAGGAAGGGGCGGGAGCGGGGCTGTTAGCGACAC
GCAATTGCTATAGTGAGTCGTATTAGCTACGTACAGTCAGTCAGACT HMGA-97
TTAGAGAAGAGGGGAGGAGGAGGAGGAGAGGAGGAGGCGCTTAGCGACAC
GCAATTGCTATAGTGAGTCGTATTAGCTACGTACAGTCAGTCAGACT MYC99
TCCAACTATGTATACTGGGGAGGGTGGGGAGGGTGGGGAAGGTTAGCGAC
ACGCAATTGCTATAGTGAGTCGTATTAGCTACGTACAGTCAGTCAGACT IMOTIF99
TCCAACTATGTATACCCTTCCCCACCCTCCCCACCCTCCCCATTAGCGAC
ACGCAATTGCTATAGTGAGTCGTATTAGCTACGTACAGTCAGTCAGACT Humtel-95
TCATATATGACTACTTAGGGTTAGGGTTAGGGTTAGGGTTACTGCCACGC
AATTGCTATAGTGAGTCGTATTAGCTACGTACAGTCAGTCAGACT SRC89
ATGATCACCGGGAGGAGGAGGAAGGAGGAAGCGCGCTGCCACGCAATTGC
TATAGTGAGTCGTATTAGCTACGTACAGTCAGTCAGACT Primer:
(45 MER)
AGTCTGACTGACTGTACGTAGCTAATACGACTCACTATAGCAATT

Example 44

Cytochrome P450 (CYP450) Inhibition Assay

The compounds of the present invention may be evaluated for potential inhibitory activity against cytochrome P450 P450 isoenzymes. Generally, six reaction tubes with 100 μL of a solution containing 50 mM potassium phosphate, pH 7.4, 2.6 mM NADP+, 6.6 mM glucose 6-phosphate, 0.8 U of glucose 6-phosphate dehydrogenase/mL and 1:6 serial dilutions of the test compound are prepared along with six tubes of 1:6 serial dilutions of a suitable positive control inhibitor. The reactions are initiated by adding 100 μL of a pre-warmed enzyme/substrate solution to the reaction tubes. A zero time-point control reaction is prepared by adding 50 μL of acetonitrile to 100 μL of cofactor solution to inactivate the enzymes, then adding 100 μL of enzyme/substrate solution. A control reaction with no inhibitor is also prepared. After a suitable incubation at 37 C, the reactions are terminated by the addition of 50 μL of acetonitrile. The reactions are analyzed for the metabolite forms of the probe substrate using LC/MS/MS.

Example 45

Evaluation of Compound Efficacy in Tumor Suppression

An experiment for evaluating the efficacy of compounds of the present invention in athymic nude mouse models of human carcinoma is designed as follows. Male or female animals (mouse, Sim) (NCR, nu/nu) aged five to six weeks and weighing more than 20 grams will be used. The animals are purposely bred and will be experimentally naïve at the outset of the study. Tumors will be propagated either from injected cells or from the passage of tumor fragments. Cell lines to be used include, but are not limited to, MiaPaca, PC3, HCT116, HT29 and BT474.

Cell implantation. One to ten million cells suspended in 0.1 ml culture media with or without Matrigel (Collaborative Biomedical Products, Inc, Bedford, Mass.) will be inoculated subcutaneously in the right flank of sixty animals. There will only be one injection per animal. Within 7-14 days of injection tumors will develop to a study use size of approximately 1.0 cm$^3$. A small subset (<10/60) animals will be considered Donors and tumors will be grown 10-28 days and to a size of 1.5 cm$^3$ in order to be used for serial transplantation. For estrogen dependent tumor lines (i.e. BT474), female mice will have estrogen pellets implanted subcutaneously between the shoulder blades via 10 gauge trocar three days before cells or tumor fragments are injected/implanted.

Fragment transplantation. Donor animals with be euthanized and tumors surgically excised and cut into 2 mm$^3$ size fragments using aseptic technique. Animals to be implanted will be lightly anesthetized with isoflurane. The area to implanted will be cleansed with 70% alcohol and betadine. A single fragment will then be implanted subcutaneously using a trocar.

Efficacy studies. Groups of 50-60 tumor bearing animals will be randomly divided into three to eight groups containing 7 animals each, as described in Table 5.

TABLE 5

| Group No. | Number of Males/ Females | Dose Level | Dose Vol. (μL) | Dose Solution Conc. (mg/mL) | Number Euthanized on: Day 28-42 |
|---|---|---|---|---|---|
| 1 | N = 7 | Negative Control* | 250 | | all |
| 2 | N = 7 | Positive Control** | 10-400 IP | 2 to 5 IP | all |
| | | | 10-250 IV | 2.5 to 5 IV | |
| | | | 125-500 PO | 10 PO | |
| Group 3-8 | N = 7/grp <56 total | Test Compound 1 to 25 IP 1 to 50 IV 50 to 200 PO | 10-400 IP 10-250 IV 125-500 PO | 2.5 to 5 IP 2.5 to 5 IV 10 PO | all |

*Vehicle/Diluent
**Commercially available anticancer compounds including, but not limited to, Taxol, CPT11 and Gemcitabine will be used as positive controls.

Dosing Procedure. Compounds will be administered QD, QOD, Q3D or once weekly via IP, IV (lateral tail vein) or PO. Animals will be dosed in a systematic order that distributes the time of dosing similarly across all groups. For bolus IP and PO dosing, animals will be manually restrained. For IV bolus dosing or short term IV infusion (one minute), animals will be mechanically restrained but not sedated. Disposable sterile syringes will be used for each animal/dose.

Example 46

Evaluation of Maximum Tolerated Doses

An experiment for evaluating the maximum tolerate dose (MTD) of compounds of the present invention is designed as follows. Selection for animal models is as previously described in Example 45.

Acute Toxicity Studies. To determine the MTD after a single dose, sixty naive animals will be randomly divided into groups containing 10 animals (5 male and 5 female) and will receive either one compound via two routes of administration or two compounds via a single route of administration. A single 50 mg/kg IV dose has been shown to be tolerated, and is used as the preliminary low dose levels. The low dose for oral studies is based on projected tolerability and will be adjusted downward if necessary. Designed dose levels, dose volumes and dose solution concentration are described in Table 6.

TABLE 6

| Group No. | Number of Males and Females | Dose Level (mg/kg) | Dose Vol. (µL) | Dose Solution Conc. (mg/mL) | Number Euthanized on: Day 7 |
|---|---|---|---|---|---|
| 1 | | Test compound #1 | | | all |
| | N = 5 M | 50 IV | 250 IV | 5 IV | |
| | N = 5 F | 100 PO | 500 PO | 5 PO | |
| 2 | | Test compound #1 | | | all |
| | N = 5 M | 75 IV | 250 IV | 8.25 IV | |
| | N = 5 F | 200 PO | 500 PO | 10 PO | |
| 3 | | Test compound #1 | | | all |
| | N = 5 M | 100 IV | 250 IV | 10 IV | |
| | N = 5 F | 300 PO | 500 PO | 15 PO | |
| 4 | | Test compound #2 | | | all |
| | N = 5 M | 50 IV | 250 IV | 5 IV | |
| | N = 5 F | 100 PO | 500 PO | 5 PO | |
| 5 | | Test compound #2 | | | all |
| | N = 5 M | 75 IV | 250 IV | 8.25 IV | |
| | N = 5 F | 200 PO | 500 PO | 10 PO | |
| 6 | | Test compound #2 | | | all |
| | N = 5 M | 100 IV | 250 IV | 10 IV | |
| | N = 5 F | 300 PO | 500 PO | 15 PO | |

SubChronic Studies. To characterize dose-response relationships following repeated doing, twenty-five naive animals will be randomly divided into groups containing 5 animals each as described in Table 7. Each two week study will test only one compound via a single routes of administration at an optimal dose derived from data collected in prior acute toxicity studies.

TABLE 7

| Group No. | Number of Males or Females | Dose Level (mg/kg) | Dose Vol. (µL) | Dose Solution Conc. (mg/mL) | Number Euthanized on: Day 14 |
|---|---|---|---|---|---|
| 1 | N = 5 | Negative Control | 250 IV 500 PO | Depends on Dose Level | all |
| 2 QD | N = 5 | Test Compound As Determined in MTD Studies | 250 IV 500 PO | Depends on Dose Level | all |
| 3 QOD | N = 5 | Test Compound As Determined in MTD Studies | 250 IV 500 PO | Depends on Dose Level | all |
| 4 Q3D | N = 5 | Test Compound As Determined in MTD Studies | 250 IV 500 PO | Depends on Dose Level | all |
| 5 Q7D | N = 5 | Test Compound As Determined in MTD Studies | 250 IV 500 PO | Depends on Dose Level | all |

Dosing Procedure. Compounds will be administered QD, QOD, Q3D or Q7D via IV (lateral tail vein) or PO. Animals will be dosed in a systematic order that distributes the time of dosing similarly across all groups. For PO dosing, animals will be manually restrained. For IV bolus dosing or short term IV infusion (one minute), animals will be mechanically restrained but not sedated. Disposable sterile syringes will be used for each animal/dose.

Example 47

Evaluation of Pharmacokinetic Properties

Pharmacokinetic studies for evaluating pharmacokinetic properties of the compounds herein are designed as follows. Male animals (mouse, Balb/c or rat, SD) aged five to six weeks. For rat models, rats weighing more than 200 grams will be used. Twenty animals will randomly divided into 4 groups, as shown in Table 8. One group with be untreated and samples taken to be used as a base line. The other three groups will be and administered a single dose of compounds by intravenous injection.

TABLE 8

| Group No. | No. of Animals | Time followed by injection (h) |
|---|---|---|
| 1 | 2 | Naïve |
| 2 | 6 | .25, 2, 8 |
| 3 | 6 | .5, 4, 12 |
| 4 | 6 | 1, 6, 24 |

Dosing Procedure. Compounds will be administered via IV (lateral tail vein), IP or PO. Animals will be dosed in a systematic order that distributes the time of dosing similarly across all groups. For IP and PO dosing, animals will be manually restrained. For IV bolus dosing or short term IV infusion (one minute), animals will be mechanically restrained but not sedated. Disposable sterile syringes will be used for each animal/dose.

Approximately 0.5 ml of blood will be collected from the naive animals via cardiac puncture prior to the first dose Terminal blood samples (0.5 ml) will be collected via cardiac puncture from two animals per group per time point according to the above chart. All samples will be placed in tubes containing lithium heparin as anticoagulant and mixed immediately by inverting. They will be centrifuged and the plasma flash frozen in liquid nitrogen, stored at −70° C. or greater and analyzed for drug levels.

Example 48

Determination of in Vitro Metabolic Stability in Hepatocytes

The protocol is designed to determine the stability of a new chemical entity in the presence of hepatocytes (human, rat, dog, monkey) in in vitro incubations. The test article will be incubated with hepatocytes and suitable media for various times at 37° C. The reaction mixtures will be extracted and analyzed by LC/MS/MS for the parent compound and anticipated metabolites. If applicable, a half-life will be calculated for the consumption of the test article. Metabolism controls will be run for comparison of the half-life values with that obtained for the test article. The metabolism controls are tolbutamide, desipramine and naloxone, and these compounds have defined pharmacokinetics corresponding to low, moderate and high in vivo clearance values, respectively.

Metabolic Stability Study. Generally, solutions of the test compounds are prepared along with a cocktail solution of metabolism controls that are intended to provide a reference for enzyme activity. The reactions are initiated by combining these pre-warmed solutions with hepatocyte suspensions and with a media control solution. Control zero samples are taken from these reactions immediately after initiation. Additional samples are taken at appropriate time points. Each sample is immediately placed in a terminating solution (acidified MeCN containing IS) to stop the reaction. Hepatocyte blank suspensions and test compound standard solutions are prepared.

Samples and standards for the test compound as well as appropriate blanks are subjected to a custom sample preparation procedure and analyzed for the parent and/or metabolite form of the test compound using HPLC coupled with tandem mass spectrometry. Samples and standards for the metabolism controls are subjected to the analytical method described herein. Where Krebs Henseleit buffer is added, the buffer is bubbled with 5% $CO_2$ in air at room temperature for 5-10 minutes before adding BSA to a final concentration of 0.2% w/v. The volume of terminating solution and the method of sample preparation will be determined for the test article during method development.

Test Article/Media Solution. A solution of the test article will be prepared by adding an appropriate volume of the stock solution to 0.2% BSA in Krebs Henseleit buffer equilibrated with 5% $CO_2$ in air. The final concentration will be 20 μM and the final assay concentration at initiation of the reactions will be 10 μM.

Metabolism Controls/Media Solution. A solution of tolbutamide, desipramine and naloxone will be prepared by adding an appropriate volume of each 10 mM stock solution to 0.2% BSA in Krebs Henseleit buffer equilibrated with 5% $CO_2$ in air. The final concentration will be 20 μM for each metabolism control and the final assay concentration will be 10 μM at initiation of the reactions.

Hepatocyte Suspension Solution. The hepatocytes will be thawed and isolated according to the vendor (Invitrotech, Inc.) instructions. During the final step of the procedure, the viability of the cells will be determined using the method of trypan blue exclusion. Then, the hepatocytes will be resuspended with 0.2% BSA in Krebs Henseleit buffer equilibrated with 5% $CO_2$ in air so the final concentration is 0.5 million viable cells/mL. The concentration at the initiation of the reactions will be 0.25 million viable cells/mL.

Initiating Test Article Incubation. Equal volumes of the test article solution prepared in step 2.1.3 will be dispensed into four polypropylene scintillation vials. The vials are pre-warmed for 5-10 minutes at 37° C. with 95% humidity and 5% $CO_2$. Equal volumes of 0.2% BSA in Krebs Henseleit buffer equilibrated with 5% $CO_2$ in air will be added to two of the vials and mixed thoroughly. Immediately after initiating the reaction, a timer is started and a 100 μL sample is removed from each vial and placed into a 1.7-mL centrifuge tube containing a suitable volume of terminating solution. These samples will serve as media controls to check for non-enzymatic degradation and non-specific binding to the vessel.

Equal volumes of the hepatocyte suspension prepared in step 2.1.5 will be added to two of the vials and mixed thoroughly. Immediately after initiating the reaction, a timer is started and a 100 μL sample is removed from each vial and placed into a 1.7-mL centrifuge tube containing a suitable volume of terminating solution. All vials are placed in an incubator maintained at 37° C., 95% humidity and 5% $CO_2$.

Initiating Metabolism Control Incubation. Equal volumes of the metabolism control solution prepared in step 2.1.4 will be dispensed into two polypropylene scintillation vials. The vials are pre-warmed for 5-10 minutes at 37° C. with 95% humidity and 5% $CO_2$. Equal volumes of the hepatocyte suspension prepared in step 2.1.5 will be added to each of the two vials and mixed thoroughly. Immediately after initiating the reaction, a timer is started and a 100 μL sample is removed from each vial and placed into a 1.7-mL centrifuge tube containing an equal volume of terminating solution. All vials are placed in an incubator maintained at 37° C., 95% humidity and 5% $CO_2$.

Sample Collection. The vials will be gently shaken and samples (100 μL) will be removed and placed into a 1.7-mL centrifuge tube containing an appropriate volume of terminating solution according to the following schedule: Test article samples are taken after 5, 10, 15, 30, 60, 90 and 120 minutes; metabolism control samples are taken after 30, 60, 90 and 120 minutes. Immediately after removal of the samples, the vials are placed back in the incubator until the last sample is collected.

Blank Preparation. A sample (100 μL) of the hepatocyte suspension will be added to an equal volume of 0.2% BSA in Krebs Henseleit buffer and mixed thoroughly. A 100 μL sample of this solution will be removed and placed into a 1.7-mL centrifuge tube containing the same volume of terminating solution used for the test article reaction. A sample of the incubation medium (0.2% BSA in Krebs Henseleit buffer) will be placed into a 1.7-mL centrifuge tube containing the same volume of terminating solution used for the test article reaction.

Sample Preparation and Analysis. All vials will be centrifuged at 16,000 g for 3 minutes. The supernatants will be placed into polypropylene autosampler vials and stored at 4° C. (<1 day) or −70° C. (>1 day) until analysis. The test article solutions will be analyzed using HPLC/MS/MS conditions according to standard procedures. In one example, the following HPLC conditions may be used: column (Phenomenex Synergi Hydro-RP, 100.0×2.0 mm, 5 μm); guard column (Phenomenex C18, 4.0×2.0 mm, 5 μm); flow rate (0.3 mL/min); column temperature at 45° C.; injection volume at 10 μL; and ambient autosampler temperature.

Example 49

Determination of in Vitro Metabolic Stability in Microsomes

The protocol is designed to determine the stability of a new chemical entity in the presence of liver microsomes (human, rat, dog, monkey) in in vitro incubations. The test article will be incubated with microsomes and suitable media for various times at 37° C. The reaction mixtures will be extracted and analyzed by LC/MS/MS for the parent compound and anticipated metabolites. If applicable, a half-life will be calculated for the consumption of the test article. Metabolism controls will be run for comparison of the half-life values with that obtained for the test article. The metabolism controls are tolbutamide, desipramine and testosterone, and these compounds have defined pharmacokinetics corresponding to low, moderate and high in vivo clearance values, respectively.

Metabolic Stability Study. Generally, six pre-warmed reaction vials with 100 μL of a solution containing 50 mM potassium phosphate, pH 7.4, 2.6 mM NADP+, 6.6 mM glucose 6-phosphate, 0.8 U/mL of glucose 6-phosphate dehydrogenase and 1, 10 or 50 μM of the test compound are prepared. Similar reactions with metabolic controls representing low (tolbutamide), moderate (desipramine), and high (testosterone) clearance compounds are run simultaneously with the same enzyme solution. The reactions are initiated by adding 100 μL of a pre-warmed enzyme solution and incubated at 37° C. The zero time-point reaction is prepared by adding 50 μL of acetonitrile (containing internal standard) to the test compound/cofactor solution prior to adding the enzyme solution. After 15, 30, 60, 90 and 120 minutes, a reaction tube is removed from the water bath and the reaction is terminated with 50 μL of acetonitrile containing internal standard. The reactions are extracted and the samples are analyzed for the parent form of the test compound and one metabolite using a C18 column with MS/MS detection. Each assay is performed in duplicate.

Cofactor/Test compound Solution Concentrations. A stock solution of 10 mM NCE will be prepared in 10% DMSO (v/v). For all assays, a 2, 20 or 100 μM solution of the test article will be prepared in 50 mM potassium phosphate, pH 7.4, 2.6 mM NADP+, 6.6 mM glucose 6-phosphate and 0.8 U/mL of glucose 6-phosphate dehydrogenase (cofactor solution).

Cofactor/Metabolism Control Solution Concentrations. Stock solutions of the metabolism controls (tolbutamide, desipramine, and testosterone) will be used to prepare a 6 μM solution of the metabolism control in cofactor solution described in step Enzyme Solution Concentrations. The enzyme solutions will be prepared by adding liver microsomes to 50 mM potassium phosphate, pH 7.4, to a final concentration of 1 mg/mL. All microsomes were purchased from XenoTech or Invitro-Tech, Inc.

Initiating the Reactions. All the reaction tubes will be pre-warmed at 37° C. in a water bath for about 3-5 minutes. The zero time-point control reaction will be prepared for each replicate by adding 50 μL of acetonitrile containing 15.9 μM nebularine (internal standard) to 100 μL of cofactor solution to inactivate the enzymes, and then vortex mixing. The reactions will be initiated by adding 100 μL of the enzyme solution to each of the tubes and vortex mixing. All the tubes, including the zero time-point control, will be incubated in a 37° C. water bath. The final concentrations of all components in the tubes after initiating the reactions are 50 mM potassium phosphate, pH 7.4, 1.3 mM NADP+, 3.3 mM glucose 6-phosphate, 0.4 U/mL of glucose 6-phosphate dehydrogenase, 0.5 mg/mL liver microsomes and 1, 10 or 50 μM test article.

Terminating and Extracting the Reactions. After 15, 30, 60, 90 and 120 minutes at 37° C., the reactions will be terminated by the addition of 150 μL of acetonitrile containing 15.9 μM nebularine (internal standard). The zero time-point control is removed from the water bath after 120 minutes. All vials will be centrifuged at 16,000 g for 3 minutes. The supernatants will be placed into polypropylene autosampler vials and stored at 4° C. (<1 day) or −70° C. (>1 day) until analysis.

Analysis of Test Article Solutions. The test article solutions will be analyzed using HPLC/MS/MS conditions according to standard procedures, such as those described in Example 60.

Example 50

Bacterial Mutagenicity Test

This Mutagenicity Assessment assay (Ames Assay) evaluates the potential of the test article extracts to induce histidine (his) reversion in *S. typhimurium* (his− to his+) or tryptophan (trp) reversion in *E. coli* (trp− to trp+) caused by base changes or frameshift mutations in the genome of tester organisms.

Generally, a plate incorporation assay is conducted with five strains of *Salmonella typhimurium* (TA97a, TA98, TA100, TA102, and TA1535) and one strain of *Escherichia coli* (WP2-uvrA−) in the presence and absence of an exogenous mammalian activation system (S9). The test article was dissolved in 5% dextrose. A series of dilutions are then prepared in saline just prior to testing. A Range Finding Study is also conducted for this assay to determine the appropriate doses for definitive mutagenicity assessment.

Test Material Preparation

A stock solution of test article is prepared at 20.0 mg/mL as follows: 1.0 g test article is added to 15.0 mL of 0.1 HCl for 1 minute. The test article is stirred for 15 minutes at room temperature. Next 33.0 mL of deionized water is added and allowed to stir for 30 minutes. The pH is then adjusted to 3.53. Lower doses are prepared by dilution in 5% dextrose from this stock immediately prior to use. To minimize any change of degradation, the test article solutions are kept on ice after preparation and until just prior to dosing procedures. The test article is administered in vitro, through a solvent compatible with the test system.

Genotypic Characterization of the Test Strains

Working stocks of test strains will be confirmed for genotypic markers and acceptable spontaneous reversion rates. All working stocks should demonstrate a requirement for histidine or tryptophan (*E. coli* only). Additionally, the following conformations will be made with each assay, as appropriate: sensitivity to crystal violet due to the rfa wall mutation; sensitivity to ultraviolet light due to the deletion of the uvrB gene (uvrA in *E. coli*), resistance to ampicillin due to the presence of the pKM101 plasmid; and resistance to tetracycline due to the presence of the pAQ1 plasmid. Spontaneous reversion rates for the strains will be determined using the negative controls.

Test articles that are water-soluble will be preferentially dissolved in isotonic saline. Test articles that are not water-soluble will be dissolved in Dimethylsulfoxide (DMSO). If DMSO is anticipated to cause adverse reactions with the test article, the test article will be suspended in carboxymethyl-cellulose. In order to aid in dissolution, heating, vigorous vortexing or alternative solvents may be employed.

Test System

This assay is conducted in accordance with the plate incorporation methodology originally described by Ames (Ames et al., *Mutation Research* (1975) 31:347-364) and updated by Maron and Ames (Maron et al., *Mutation Research* (1983) 113:173-215). This assay has historically been used to detect mutation in a gene of a histidine requiring strain to produce a histidine independent strain or concordantly, to detect mutation in a gene of a tryptophan requiring strain to produce a tryptophan independent strain. In addition, it has been shown to detect diverse classes of chemical mutagens which produce heritable DNA mutations of a type which are associated with adverse effects.

The *Salmonella typhimurium* strains to be used in this assay, TA97a, TA98, TA100, and TA102 are described by Maron and Ames, supra; Green et al., *Mutation Research* (1976) 38:33-42); and Brusick et al., *Mutation Research* (1980) 76:169-190)). *S. typhimurium* strain TA1535 and *E. coli* strain Wp2-uvrA$^-$ may be obtained from American Type Culture Collection, Manassas, Va. (ATCC numbers: 29629 and 49979, respectively). All working stocks of test strains will be confirmed for genotypic markers and acceptable reversion rates. Working stocks should demonstrate a requirement for histidine or tryptophan (*E. coli* only).

Experimental Methods

Master plates of the tester strains are prepared from frozen working stocks. To create working cultures for each bacterial strain used in the assay, a single colony is transferred from the master plate into Oxoid nutrient broth and incubated, with shaking, at 37±2° C. until an optical density (at 650 nm) of 0.6-1.6 was reached. This overnight culture is used for the mutagenicity test and for genotypic confirmation. Genotype tests are performed as described in the protocol.

For both the dose range and mutagenicity test, a top agar consisting of 0.6% Difco agar in 0.5% NaCl is melted and a solution of 0.5 mM L-histidine/0.5 mM biotin or 0.5 mM L-tryptophan is added to the melted top agar at a ratio of 10 mL per 100 mL agar. The supplemented agar is aliquotted, 2 mL per tube and held at 45-47° C. To prepare the top agar for treatment, 0.1 mL of the test article or control, 0.1 mL of the bacterial culture and 0.5 mL of phosphate buffered saline are added to the molten agar. The mixture is briefly vortexed and poured onto a room temperature minimal glucose agar plate (1.5% Difco agar, 2% glucose, in Vogel-Bonner medium E). Metabolic activation is provided by adding 0.5 mL of the S9 mix in place of the PBS. The plates are allowed to harden and then incubated 48-72 hours at 37±2° C. All plates are counted using an automatic image analysis system. Negative control and test article treated plates were also examined for the presence of a bacterial lawn.

Exogenous Metabolic Activation

The in vitro metabolic activation system used in this assay is comprised of Sprague Dawley rat liver enzymes and a cofactor pool. The enzymes are contained in a preparation of liver microsomes (S9 fraction) from rates treated with Arochlor to induce the production of enzymes capable of transforming chemicals to more active forms. Immediately prior to use, the S9 is thawed and mixed with a cofactor pool to contain 5% S9, 5 mM glucose 6-phosphate, 4 mM β-nicotineadenine dinucleotide phosphate, 8 mM MgCl$_2$ and 33 mM KCl in a 200 mM phosphate buffer at pH 7.4.

Dose Levels and Replicates

The test article is tested in triplicate at five dose levels (20.0, 10.0, 5.0, 2.5, and 1.25 mg/mL) along with appropriate vehicle (5% dextrose) and positive controls in the dose range assay. This is equivalent to 2.0, 1.0, 0.5, 0.25, and 0.125 mg/plate.

For the definitive assay, three dose levels are chosen (10.0, 10.0, and 5.0 mg/mL), which is equivalent to 2.0, 1.0, and 0.5 mg/plate. All treatments, including negative and positive control, are plated in triplicate against test strains TA97a, TA98, TA 00, TA102, TA1535, and WP2-uvrA$^-$ in the presence and absence of metabolic activation. These doses are chosen based on inducing a range of test article toxicity and maximizing the applied dose.

Control Substances

Control substances may be prepared and used in the mutagenicity assay as described in Table 9.

TABLE 9

| Control | Strain | Metabolic Activation | Concentration |
|---|---|---|---|
| ICR-191 Acridine | TA97a | No | 1.0 µg/plate |
| 2-nitrofluorene | A98 | No | 10.0 µg/plate |
| Sodium azide | TA100 and TA1535 | No | 1.5 µg/plate |
| 1-methyl-3-nitro-1-nitrosognanidine | WP2-uvrA$^-$ | No | 4.0 µg/plate |
| 2-aminoanthracene | all strains (except TA1535) | Yes | 10.0 µg/plate |
| 2-aminoanthracene | TA1535 | Yes | 1.6 µg/plate |

Negative (Vehicle) Control

Tester strains are plated with untreated dextrose solution at the corresponding maximum concentration (0.1 mL), with and without S9. These plates serve as the negative controls and provide information regarding background lawn and revertant colony formation.

Dose Range Assay

The initial dose range assay starts at the maximum concentration of 2.0 mg/plate. The four lower doses to be tested are diluted in a 1:2 dilution series.

Reverse Mutation Assay

Each separate bacterial strain, with and without S9, is considered a separate experiment with its own concurrent positive and vehicle controls. All plates are scored with an automated colony counter and a printout of the data was made. The positive controls consists of direct-acting mutagens and mutagens requiring metabolic transformation. A two-fold or greater increase in reversion rates is observed for all strains with the appropriate positive control. The negative control article reversion rates for each strain should be within or slightly below the expected ranges from laboratory historical data. An induced positive result for any strain would be demonstrated by at least a two-fold increase in the number of revertant colonies per plate over the negative control values.

Example 51

In Vitro Chromosome Aberration Assay in CHO Cells

The Chromosomal Aberration Assay is one of several in vitro tests that can be used to screen materials for their potential genetic toxicity. Chromosome aberrations are mutations which have been associated with carcinogenesis. Therefore, the chromosome aberration assay is relevant for testing potential mutagens and carcinogens (Galloway et al., *Environ. Mut.* (1985) 7:1-51; Galloway et al., *Environ. Mut.* (1987) 10:1-175). This Chromosome Aberration Assay evaluates the potential of the test article extracts to induce damage in Chinese Hamster Ovary Cells (CHO). This test will be conducted in the presence and absence of an exogenous mammalian activation system (S9) over three treatment periods. All negative control treated preparations should demonstrate normal levels of spontaneously occurring aberrations while positive control treated cultures should demonstrate dramatic, dose dependent increases in aberrant chromosomes.

This assay is designed to determine whether a test material is clastogenic, i.e., whether it has the capacity to break chromosomes. Clastogenicity is an important endpoint because it is through chromosomal breakage and inappropriate rejoining that certain oncogenes (e.g., myc) can be activated and certain tumor suppressor genes (e.g., those suppressing retinoblastoma) can be inactivated). In this test, mammalian Chinese Hamster Ovary (CHO) cells are exposed to the test material and blocked in metaphase using a spindle poison. Visualization of chromosomes is performed microscopically after hypotonic swelling, fixing and staining the treated CHO cells. Agents found to be capable of inducing chromosome breakage have a high probability of being carcinogens and also have the potential for inducing heritable chromosomal defects.

The CHO-$K_1$, cell line (ATCC number: CCL-61) is a proline auxotroph with a modal chromosome number of 20 and a population doubling time of 10-14 hours. This system has been shown to be sensitive to the clastogenic activity of a variety of chemicals (Preston et al., *Mutation Res.* (1981) 87:143-188). CHO cells were grown and maintained in McCoy's 5A medium supplemented with 10% fetal calf serum, 1% L-glutamine (2 mM), penicillin (100 units/mL), and streptomycin (100 μg/mL). Cultures are incubated in 5-7% $CO_2$ with loose caps in a humidified incubator at 37±2° C.

Test Procedures

A stock solution is prepared at 5 mg/mL. Lower doses are prepared by dilution in 5% dextrose from this stock immediately prior to use. To minimize any chance of degradation, the test article solutions are kept on ice after preparation and until just prior to dosing procedures.

Cells are seeded at approximately 1-1.5×$10^6$ cells per 75 $cm^2$ tissue culture flask in 10 mL fresh medium one day prior to treatment. For treatment, spent medium is replaced with fresh growth medium and the test article extract, negative or positive control is added to each flask. Positive controls are dosed in 0.1 mL volumes to minimize vehicle toxicity. The test article dilutions and negative control are dosed in 1 mL volumes. Fresh medium is added to bring the total treatment volume to 10 mL. For the portion of the test with metabolic activation, the S9 activation mix is added to serum free medium at 1.5%, (v/v) final concentration. All treatments are carried out in duplicate. The cells are incubated at 37±2° C. in the presence of the test article extract, the S9 reaction mixture (metabolic activation portion of the study only) and growth medium. The assay is divided into three treatment periods: 3 hours, 3 hours with S9 activation, and 20 hours.

After the treatment period, all flasks are evaluated microscopically for gross manifestations of toxicity. i.e., morphological changes in cells or significant cell detachment. All flasks are washed twice with phosphate buffered saline (PBS). Normal growth medium containing 10% fetal bovine serum (FBS) is added to the freshly washed cells and the flasks are returned to the incubator for an additional 14.5-15.5 hours. Microscopic evaluation is performed immediately prior to harvest. Two hours prior to harvest, 1 μg of colcemid is added (0.1 μg/mL final concentration) to all flasks to accumulate dividing cells.

The test article extracts are tested in duplicate at six dose levels (0.5, 0.16, 0.05, 0.016, 0.005, and 0.0016 ml/mL final concentration in culture) along with appropriate vehicle and positive controls.

Metabolic Activation System

The use of a metabolic activation system is an important aspect for evaluation of a test article, as some compounds exist only in a promutagenic state. That is, they become mutagenic only after being acted upon by an outside metabolic source. In vitro test systems lack this ability to metabolize compounds unless an outside system such as S9 is added.

The in vitro metabolic activation system used in this assay is comprised of Sprague Dawley rat liver enzymes and an energy producing system necessary for their function (NADP and isocitric acid; core reaction mixture). The enzymes are contained in a preparation of liver microsomes (S9 fraction) from rats treated with Arochlor 1254 to induce enzymes capable of transforming chemicals to more active forms. The S9 may be purchased from Moltox (Boone, N.C.) and retained frozen at less than −70° C. until use. This S9 fraction is thawed immediately before use and added to the core reaction mixture.

Cell Fixation, Staining and Scoring

Metaphase cells are collected by mitotic shake off, swollen with 75 mM KCl, fixed in methanol:glacial acetic acid (3:1 v/v). Cells are pipetted onto glass slides after resuspension in fresh fixative and air dried. The slides are labeled with a blind code. Three slides are prepared from each treatment flask.

Slides are stained with Giemsa and permanently mounted. All slides are read under blind code with the exception of the high dose positive controls, which are evaluated first to ensure the aberration frequency was adequate. Two hundred cells per dose (100 from each of the duplicate flasks) are read from each of the doses. One hundred cells are read from each of the high dose positive controls in accordance with the following definitions and were scored as such.

Chromatid Type

TG (Chromatid Gap): "Tid Gap". An achromatic (unstained) region in one chromatid, the size of which is equal to or smaller than the width of a chromatid. These are noted but not usually included in final totals of aberrations, as they may not all be true breaks.

IG (Isochromatid Gap): "Chromosome Gap". The gaps are at the same locus in both sister chromatids. These are noted but are not usually included in final totals of aberrations, as they may not all be true breaks.

TB (Chromatid Break): An achromatic region in one chromatid, larger than the width of a chromatid. The associated fragment may be partially or completely displaced, or missing.

ID (Chromatid Deletion): Length of chromatid "cut" from midregion of a chromatid resulting in a small fragment or ring lying beside a shortened chromatid or a gap in the chromatid.

TR (Triradial): An exchange between two chromosomes, which results in a three-armed configuration. May have an associated acentric fragment.

QR (Quadriradial): The same as the triradial, but resulting in a four-armed configuration.

CR (Complex Rearrangement): An exchange among more than two chromosomes which is the result of several breaks and exchanges.

TI (Chromatid Interchange): Exchange within a chromosome involving one or both arms.

Chromosome Type

SB (Chromosome Break): Terminal deletion. Chromosome has a clear break forming an abnormal (deleted) chromosome with an acentric fragment that is dislocated and may remain associated or may appear anywhere in the cell.

DM (Double Minute Fragment): Chromosome interstitial deletion. These appear as small double "dots" or may be paired rings. In some cases, they cannot be distinguished from acentric fragments that result from exchanges or terminal deletions.

D (Dicentric): An exchange between two chromosomes that results in a chromosome with two centromeres. This is often associated with an acentric fragment in which it is classified as Dicentric with Fragment (DF).

MC (Multi-centric Chromosome): An exchange among chromosomes that results in a chromosome with more than two centromeres.

R (Ring): A chromosome that forms a circle containing a centromere. This is often associated with an acentric fragment, in which case it is classified as Ring with Fragment (RF). Acentric rings are also included in this category.

Ab (Abnormal Monocentric Chromosome): This is a chromosome whose morphology is abnormal for the karyotype, and often the result of such things as a translocation or pericentric inversion. Classification used if abnormally cannot be ascribed to, e.g., a reciprocal translocation.

T (Translocation): Obvious transfer of material between two chromosomes resulting in two abnormal chromosomes. When identifiable, scored at "T", not as "2 Ab".

Other

SD (Severely Damaged Cell): A cell with 10 or more aberrations of any type. A heavily damaged cell should be analyzed to identify the type of aberrations and may not have 10 or more, e.g., because of multiple fragments such as those found associated with a tricentric.

PU (Pulverized Chromosome): Despiralized or fragmented chromosome. This may simply be at a different stage of chromosome condensation.

P (+Pulverized Cell): More than one chromosome, up to the whole nucleus, is "pulverized".

PP (Polyploid Cell): A cell containing multiple copies of the haploid number of chromosomes. Polyploid cells are occasionally observed in normal bone marrow or cell culture. These are recorded but are not included in final totals of structural aberrations.

Control Substances

Control substances are prepared and used in this assay as described in published reports. Positive controls which may be used are: cyclophosphamide—High dose 15 µg/mL; cyclophosphamide—Low dose 5 µg/mL; mitomycin Cu—High dose 1.0 µg/mL; and citomycin C—Low dose 0.25 µg/mL. For negative (vehicle) control, the CHO cells are treated with the 5% dextrose negative controls with and without S9 activation. These treatments provide information regarding background numbers of aberrant cells.

Assay Validity Evaluation and Statistical Analysis

The total number of aberrations (% CA) of the solvent control culture(s) should fall within 1-14%. High dose positive controls should produce a statistically significant increase in the number of aberrations at the 95% confidence level (p<0.05) as determined by statistical analysis. Analysis of Variance (ANOVA) is used to identify significant differences between positive and negative control groups or test article and negative control groups. A difference is considered significant when the p value obtained was less than 0.05.

Example 52

Safety and Tolerance Determination in Dogs

This study is designed to determine the safety and tolerance of compounds at dose levels administered intravenously once daily to beagle dogs for five consecutive days. Safety parameters are monitored through observation, clinical pathology, and microscopic histopathology assessments.

Experimental Design

Table 10 summarizes the study design. The study will be conducted using three (3) test article and one (1) control article group. The control article is the solution (5% dextrose in water) used to dilute the test article prior to administration and was administered at the same volume as the high dose. The test article dosage levels for this study are approximately 12, 3.8, and 1.2 mg/kg. Test and control articles are administered once by intravenous (IV) infusion over approximately a one hour period on five consecutive days.

Blood samples for test article blood level analysis is taken as follows (i.e., pk/tk sampling). Approximately 1.0 mL of blood is taken from three male and three female dogs in the low dose group at approximately 20 minutes and 40 minutes from the start of the infusion, and then at the end of infusion (Time 0) and at 5, 10, 15, and 30 minutes, and 1, 2, 4, 8, 12, and 24 hours from the end of the infusion after the first and fifth doses. Also, prior to and immediately after Dose 1 and after Dose 5 for all animals, and for recovery animals prior to necropsy, approximately 5-10 second ECG tracings in a lead II configuration are obtained. Animals are terminated one (1) or 15 days after the last dose. Blood for hematology and clinical chemistry analysis is drawn pre-dose and prior to euthanasia at termination. Following euthanasia, a necropsy is performed to include collection of major organs for microscopic evaluation.

TABLE 10

| GROUP No. | ARTICLE[a] | DOSAGE (MG/KG) | PRIMARY No. ANIMALS (MALE/FEMALE) | RECOVERY (15 DAY) No. ANIMALS (MALE/FEMALE) |
|---|---|---|---|---|
| 1 | Control | 0.0 | 3/3 | 1/1 |
| 2 | Test Article | 12.0 | 3/3 | 1/1 |
| 3 | Test Article | 3.8 | 3/3 | 1/1 |
| 4 | Test Article | 1.2 | 3/3 | 1/1 |

[a]Delivered as an approximate 1 hour infusion

Test Methods

Animals are systematically assigned to groups as follows: The heaviest dog for a sex is assigned to Group 1, the next heaviest for that sex was assigned to Group 2, the next heaviest to Group 3, the next heaviest to Group 4, then continue with Groups 2, 3, 4, and 1, then Groups 3, 4, 1, and 2, continuing with this pattern until each group had a full complement of animals. The test and control article are administered at each dosing as an intravenous infusion into a cephalic or saphenous vein over approximately one hour.

Animals are weighed daily prior to dosing and prior to necropsy. All animals are observed for signs of pharmacological activity, behavioral changes, and toxicity immediately and one hour after dosing. Recovery animals are also observed once daily during the recovery period. Prior to and immediately after Doses 1 and 5 for all animals, and for recovery animals prior to necropsy, approximately five second ECG tracings in a lead II configuration are obtained. These tracings are used to provide data for interpretation of the rhythm and amplitude changes of the QRS-complex and T-wave and to measure QT intervals on a number of segments per tracing (approximately 5-10).

Blood Collection

PK/TK: Blood samples for test article blood level analysis are taken. Approximately 1 mL of blood is taken from three males and three females in the low dose group at approximately 20 minutes and 40 minutes from the start of the infusion, and then at the end of infusion (Time 0) and at 5, 10, 15, and 30 minutes, and 1, 2, 4, 8, 12, and 24 hours from the end of the infusion after the first and fifth dose. Plasma (lithium heparin anticoagulant) samples are prepared for analysis.

Clinical Pathology: After overnight fasting and prior to the first dose (baseline; all animals) and then prior to each necropsy, blood samples are taken for hematology and clinical chemistry. For hematology assays, blood collected at baseline and prior to necropsy (fasted) are analyzed for erythrocyte count, hematocrit, MCH, leukocyte count, differential WC, MCHC, hemoglobin, MCV, platelet count, PT, and APTT. For clinical chemistry assays, blood collected at baseline and prior to necropsy (fasted) are tested for: aspartate aminotransferase (ASP), globulin & A/G ratio, Alanine aminotransferase (ALT), sodium, alkaline phosphatase, potassium, gamma glutamyltransferase (GGT), chloride, glucose, calcium, blood urea nitrogen (BUN), total bilirubin, creatinine, inorganic phosphorus, total protein, cholesterol, albumin, and triglycerides.

Necropsy

Following blood sample collection, primary treatment and recovery group animals are sacrificed at their respective termination times and are necropsied. Major organs are collected, weighed, and preserved for microscopic evaluation. Necropsy included examination of the cranial, thoracic, abdominal and pelvic cavities, their viscera, the tissues, organs, and the carcass.

Statistical Methods

Statistical analysis of the clinical chemistry and hematology values and organ and body weight data will be performed to compare the test article groups to the control group. The statistical methods used for the data will be selected as appropriate: parametric data will be analyzed using a one way Analysis of Variance, non-parametric data will be analyzed using the Kurskai-Wallis test. A paired t-test will also be used to compare baseline and post treatment clinical chemistry and hematology values for each animal. Probability (p) values of 0.05 or less will be considered significant for all statistical tests.

Example 53

Safety and Tolerance Study in Rats

This study determines the safety and tolerance of a test compound at three dose levels administered intravenously once daily to rats for five consecutive days. Safety parameters will be monitored through observation, clinical pathology, and microscopic histopathology assessments. Selected animals will also undergo blood sample collection for pharmacokinetic/toxicokinetic evaluation.

Experimental Methods

Table 11 summarizes the study design. The study is conducted using three (3) test and one (1) control article groups. The high and low test article groups and the control group will consist of 28 animals each and were used to assess tolerance. The medium test article group will consist of 64 animals, of which 28 animals are used to assess tolerance and 36 animals are used to determine the level of test article in the blood at various time points after the first and fifth doses in the PK/TK portion of the study. The control article is the solution (5% dextrose in water; D5W) used to dilute the test article prior to administration and is administered at the same volume as the high dose test article group. The test article dosage levels for this study are 24, 7.6, and 2.4 mg/kg. Test and control articles are administered by intravenous (IV) injection into a tail vein over one minute on five consecutive days.

Blood samples for test article blood level analysis are taken as follows. Approximately 0.3-0.5 mL of blood is taken from three male and three female rats under anesthesia at each sample time point of pre-dose and at the end of injection (Time 0) and at approximately 0.08, 0.25, 0.5, 1, 2, 4, 8, 12, and 24 hours from the end of the injection after the first and fifth doses. Animals used to assess tolerance are terminated one day (for the primary group) or 15 days (for the recovery group) after the last dose. At termination of the tolerance test animals, blood for hematology and clinical chemistry analysis is drawn prior to euthanasia and following euthanasia. A necropsy is performed to include collection of major organs for microscopic evaluation. The animals used for the pk/tk blood sampling only to determine the level of test article are euthanized after the final blood sample was collected without any further sampling or observations.

TABLE 11

| GROUP No. | ARTICLE[a] | DOSAGE (MG/KG) | PRIMARY No. ANIMALS (MALE/FEMALE) | RECOVERY (15 DAY) No. ANIMALS (MALE/ FEMALE) |
|---|---|---|---|---|
| 1 | Control | 0.0 | 3/3 | 1/1 |
| 2 | Test Article | 12.0 | 3/3 | 1/1 |
| 3 | Test Article | 3.8 | 3/3 | 1/1 |
| 4 | Test Article | 1.2 | 3/3 | 1/1 |

[a]Delivered as an approximate 1 hour infusion

Test Methods

The test and control article are administered at each dosing as an intravenous infusion into a tail vein over approximately one minute. Animals are weighed daily prior to dosing and prior to necropsy. All animals are observed for signs of pharmacological activity, behavioral changes, and toxicity immediately and one hour after dosing. Recovery animals are also observed once daily during the recovery period. The control animals are dosed with approximately 6 mL/kg of D5W. The high, mid, and low dose test article animals are administered dosages of approximately 24 mg/kg, 7.6 mg/kg, and 2.4 mg/kg, respectively.

Blood Collection

PK/TK: Blood samples for test article blood level analysis are taken. Utilizing 18 male and 18 female medium dose animals, approximately 0.3-0.5 mL of blood is taken from three male and three female rats under anesthesia at each sampling time point of pre-dose and at the end of injection (Time 0), and at approximately 0.08, 0.25, 0.5, 1, 2, 4, 8, 12, and 24 hours from the end of the injection after the first and fifth dose. Blood sampling is via retro-orbital bleeding or cardiac puncture bleeding for an animal's terminal sample. Plasma (lithium heparin anticoagulant) samples are prepared for analysis. General procedures for chemical pathology, necropsy, and histopathology, as well as statistical methods, such as those previously described, are followed.

Example 54

Phosphorylated and Total p53 Assay Protocol

A phosphorylated and total p53 assay protocol is described as follows. On Day 1, cells are seeded at $2 \times 10^6$ cells/10 cm dish/10 mL medium. On day two, cells are treated as follows: control=0.05% DMSO (5 µl DMSO stock/10 ml medium); 1 µM test compound (1 µl Stock (10 mM)/10 ml medium); 2 µM test compound (2 µl Stock (10 mM)/10 ml medium); 3 µM test compound (3 µl Stock (10 mM)/10 ml medium); 4 µM test compound (4 µl Stock (10 mM)/10 ml medium) and 5 M test compound (5 µl Stock (10 mM)/10 ml medium).

On Day 3, cells are harvested and attached and floating cells are collected. Cells are washed twice with PBS, counted and collected at $4 \times 10^6$ cells/sample. The cell pellet is frozen at −80° C. until further use. On the same day or on Day 4, cells are extracted using a cell extraction buffer (3 mL cell extraction buffer, 300 µl protease inhibitor and 10 µl 0.3M PMSF). To each sample is added 200 µl Buffer, and the solution is vortexed and set on ice for 30 minutes, and subsequently vortexed after every 10 mins. The solution is then centrifuged at 13,000 rpm for 10 min, and 100 µl supernatant per tube are aliquoted and stored at −80° C.

Assay preparation (Day 5). An anti-rabbit IgG HRP solution is prepared by diluting 10 µl of 100× concentrate solution with 1 ml HRP diluent for each 8-well strip. A wash buffer solution is prepared by diluting the original vial (x25) using distilled water to make a x1 solution. Dilutions of p53 standard solution or p53 total solution are prepared as described in Table 12. To ensure complete reconstitution, standard 1 is mixed gently and allowed to sit for 10 minutes at room temperature.

TABLE 12

|  | Conc. | Standard Soln. | Dilution Buffer |
|---|---|---|---|
| Standard 1 | 100 Units/ml | Reconstitute 1 Vial worth 0.7 ml of standard Dil. Buffer* | |
| Standard 2 | 50 Units/ml | 250 µl of Standard 1 | 250 µl |
| Standard 3 | 25 Units/ml | 250 µl of Standard 2 | 250 µl |
| Standard 4 | 12.5 Units/ml | 250 µl of Standard 3 | 250 µl |
| Standard 5 | 6.25 Units/ml | 250 µl of Standard 4 | 250 µl |
| Standard 6 | 3.12 Units/ml | 250 µl of Standard 5 | 250 µl |
| Standard 7 | 1.6 Units/ml | 250 µl of Standard 6 | 250 µl |
| Standard 8 | 0 |  | 250 µl |

Test Procedure. Allow all solution to reach RT and mix gently before use. Take out and insert 8-well strips. Add 100 µl of standard dilution buffer to standard 8 well (0 ng/ml/well or 0 Units/well). Add nothing to the chromogen blank well. Add 100 µl of standard or diluted sample to the appropriate microtiter wells. Generally, the sample should be diluted with standard dilution buffer at least 1:10 or greater. Each sample is run in duplicates. Gently tap the side of the plate to thoroughly mix. Cover plate with plate cover and incubate for 2 hours at RT or o/n at 4 C. Wash wells with 400 µl working wash buffer 4 times. Let soak for 15-30 sec., and then aspirate the liquid. After washing, the plate is inverted and tapped dry on absorbance tissue. Add 100 µl of anti-p53 [pS15] or anti-p53 (total) (detection antibody) to each well except chromogen blank. Tap gently to mix; cover plate and incubate 1 hour at RT. Aspirate solution from wells thoroughly.

Wash wells with 400 µl working wash buffer four times. Let soak for 15-30 sec., and then aspirate the liquid. After washing, the plate is inverted and tapped try on absorbance tissue. Add 100 µof anti-rabbit IgG HRP working soln. to each well except chromogen blank. Cover plate and incubate 30 min at RT. Wash wells with 400 µl working wash buffer four times. Let soak for 15-30 sec., and then aspirate the liquid. After washing, the plate is inverted and tapped try on absorbance tissue. Add 100 µl of TMB (stabilized chromogen substrate) to each well and incubate for 30 min. at RT in the dark. The color will change to blue. Add 100 µl Stop soln. Tap plate gently to mix. The color should change to yellow. Read the plate at A450 nm by setting chromogen blank (=100 µl TMB+100 µl Stop soln) as blank. Read absorbance within 2 hours of assay completion.

Example 55

Caspase-3/7 Assay Protocol

A Caspase-3/7 assay protocol is described as follows. On Day 1, seed $0.015 \times 10_6$ HCT-116 cells/50 ul/well. Incubate o/n in 37° C. $CO_2$ incubator. On Day 2, remove 25 ul of medium from wells. Treat HCT-116 cells with 1, 3, and 5 uM test compound. Treat positive control group with Staurosporin 0.01, 0.1, 1 uM. Keep six negative control wells treated with medium only (add 25 ul of diluted sample to appropriate wells). Incubate for 24 h at 37° C. in a $CO_2$ incubator. On Day 3, prepare Apo-ONE Homogeneous Caspase-3/7 assay reagent (Promega) at 10 ul reagent/1 ml buffer. Add 50 ul of diluted reagent. Incubate one hour at room temp. Measure fluorescence at 485/520.

Example 56

Annexin V-Alexa 488 Staining Protocol

An Annexin V-Alexa 488 staining protocol is described as follows. Seed $1.5-2.0 \times 10^6$ HCT-116 cells/10 cm dish/10 ml medium. Incubate o/n or up to 24 hrs at 37° C. in $CO_2$ incubator. The following day, treat cells with 1, 2, 3, 4 and 5 µM test compound. Keep one or two untreated plates (medium only) as control plates. The following controls are used: untreated samples (no Alexa or propidium iodide), controls treated with propidium iodide or Alexa 488 only, and controls treated with both Alexa 488 and propidium iodide. Harvest cells (collect attached as well as floating cells). Wash cells twice with cold PBS. Re-suspend cells in 1× Annexin binding buffer.

Count cells and dilute in ~1× Annexin binding buffer to ~$1 \times 10^6$ cells/0.1 ml, preparing a sufficient volume to have 100 µl per assay. Add 5 µl of the Annexin V conjugate to each 100 µl of cell suspension. Add 4 µl of propidium iodide solution (stock=1 mg/ml) to each 100 µl of cell suspension. Incubate sample at RT for 15 minutes. Add 400 µl Annexin binding buffer, mix gently and keep samples on ice. Analyze stained cells immediately by flow cytometry.

Example 57

DNA Cell Cycle Analysis Protocol

A DNA cell cycle analysis protocol is described as follows. Seed $1.5-2.0 \times 10^6$ cells/10 cm dish (seed one extra dish for unstained cells). Incubate cells in 37° C. humidified 5% $CO_2$ incubator for 24 hours. For synchronizing cells in a low growth state to make cells quiescent, remove media and rinse once with serum-free media, add 10 ml of serum-free media to each dish. Incubate the cells for 24 hr in a 37° C. humidified 5% $CO_2$ incubator. Remove media and add treatment (diluted in serum contained media, 10 ml): 1-5 µM test compound plus control. Incubate the cells for 24 hr in a 37° C. humidified 5% $CO_2$ incubator.

To trypsinize/isolate cells, remove treatment. Add 3 ml trypsin/EDTA solution. Keep floating cells and combine with attached cells. Incubate for 5 min in a 37° C. humidified 5% $CO_2$ incubator. Add 3 ml media (containing FBS) to wells and pipette into centrifuge tube. Centrifuge at 1000 rpm for 5 minutes. Decant supernatant and re-suspend pellet in 2-3 ml PBS. Count cells and wash cells once by putting $2 \times 10^6$ cells/tube, adding 2 ml PBS and centrifuging at 1000 rpm for 5 minutes. Re-suspend pelleted cells in 0.3 ml cold PBS.

To fix cells, gently add 0.7 ml ice cold 70% ethanol drop wise to tube containing 0.3 ml of cell suspension in PBS while vortexing. Leave on Ice for one hour (or up to a few days at 4 C). Centrifuge at 1000 rpm for 5 minutes. Wash one time with cold PBS (1-2 ml). Centrifuge at 1000 rpm for 5 minutes. Re-suspend cell pellet in 0.25 ml cold PBS, add 5 µl of 10 mg/ml RNAse A (the final concentration being 0.2-0.5 mg/ml). Incubate at 37 C for 1 hour. Add 10 µl of 1 mg/ml of propidium iodide solution in deionized water (the final concentration being 10 µl/ml), and keep in the dark and at 4° C. until analysis. Analyze on FACS by reading on cytometer at 488 nm. Cells may be stained with propidium iodide on the same day of analysis.

Example 58

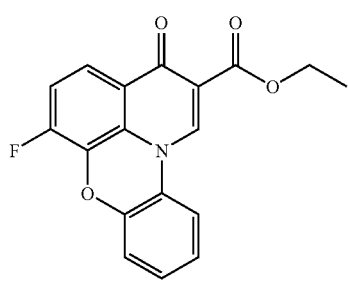

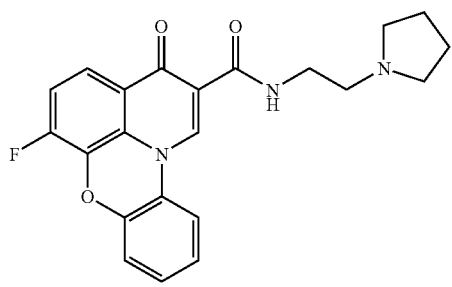

Fluoroquinolone ester (4.57 g) and 2-aminoethylpyrrolidine (3.0 ml) under an atmosphere of nitrogen were dissolved in dichloromethane (100 ml). With vigorous stirring, aluminum chloride (2.80 g) was added and the reaction stirred at room temperature for a further 2 h. The resulting mixture was washed with dilute sodium hydroxide and the organic layer separated and dried. The residue was recrystallized from methanol to yield the fluoroquinolone (5.24 g) as a white fluffy solid. $^1$H NMR (CDCl$_3$) δ 9.54 (bs, 1H), 9.25 (s, 1H), 7.9 (dd, 1H), 7.6 (dd, 1H), 7.2 (m, 3H), 3.7 (t, 2H), 2.91 (t, 2H), 1.80 (brm, 4H), 1.7 (brm, 4H).

Example 59

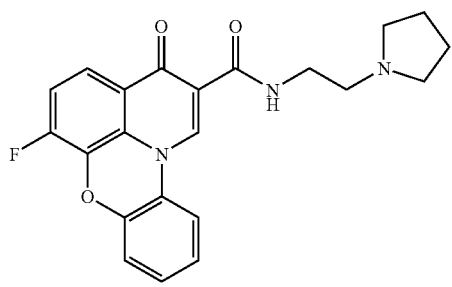

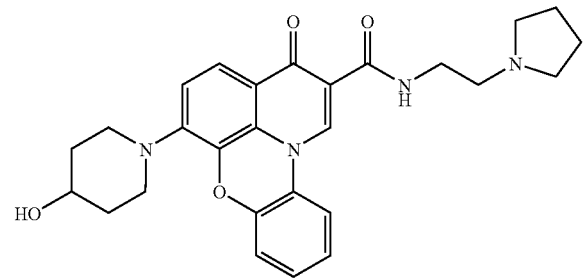

Fluoroquinolone (40 mg), 4-hydroxypiperidine (0.05 ml), diisopropylethylamineamine (0.05 ml) and N-methylpyrrolidine were mixed and heated at 190° C. for 15 min in a microwave reactor. The reaction was cooled, evaporated to a residue and purified on a reverse phase C18 column using gradient elution using 0.1% TFA in water and acetonitrile to yield 6 mg of product M+1$^+$475. $^1$H NMR (CDCl$_3$) δ 10.03 (t, 1H), 9.23 (s, 1H), 7.92 (d, 1H), 7.55 (d, 1H), 7.21 (m, 1H), 7.16 (dt, 1H), 7.11 (m, 2H), 3.94 (m, 1H), 3.65 (q, 2H), 3.52 (brm, 2H), 3.01 (dt, 2H), 2.76 (t, 2H), 2.62 (brm, 2H), 2.12 (btm, 2H), 1.18 (brm, 6H).

Example 60

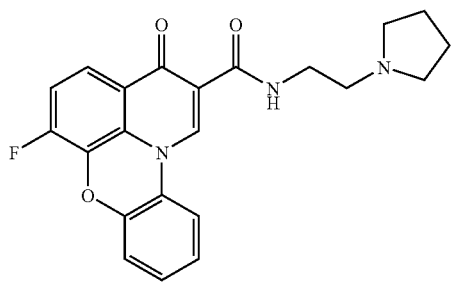

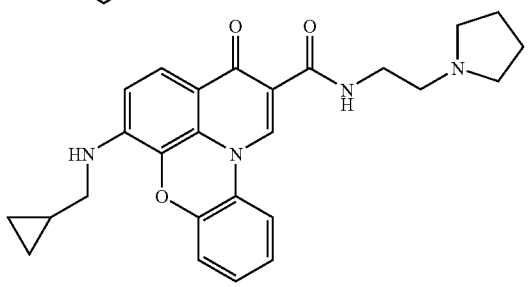

Fluoroquinolone (40 mg), cyclopropylmethylamine (0.05 ml), diisopropylethylamineamine (0.05 ml) and N-methylpyrrolidine were mixed and heated at 190° C. for 15 min in a microwave reactor. The reaction was cooled, evaporated to a residue and purified on a reverse phase C18 column using gradient elution using 0.1% TFA in water and acetonitrile to yield 17 mg of product M+1$^+$445. $^1$H NMR (CDCl$_3$) δ 10.11 (brt, 1H), 9.14 (s, 1H), 7.88 (d, 1H), 7.52 (dd, 1H), 7.19 (dt, 1H), 7.12 (m, 2H), 6.82 (d, 1H), 4.62 (t, 1H), 3.63 (q, 2H), 3.14 (t, 2H), 2.77 (t, 2H), 2.64 (brs, 4H), 1.81 (brm, 4H), 1.18 (m, 1H), 0.64 (m, 2H), 0.40 (m, 2H).

Example 61

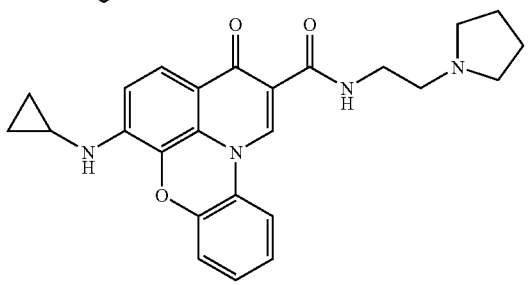

Fluoroquinolone (40 mg), cyclopropylamine (0.05 ml), diisopropylethylamineamine (0.05 ml) and N-methylpyrrolidine were mixed and heated at 190° C. for 15 min in a microwave reactor. The reaction was cooled, evaporated to a residue and purified on a reverse phase C18 column using gradient elution using 0.1% TFA in water and acetonitrile to yield 38 mg of product M+1⁺445. ¹H NMR (CDCl₃) δ 10.40 (t, 1H), 9.02 (s, 1H), 7.91 (d, 1H), 7.20 (m, 2H), 7.12 (m, 2H), 7.14 (m, 1H), 6.80 (m, 1H), 3.82 (m, 6H), 3.40 (m, 4H), 2.56 (m, 2H), 0.85 (m, 4H), 0.70 (m, 1H).

Example 62

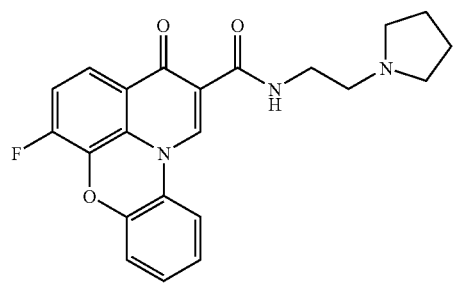

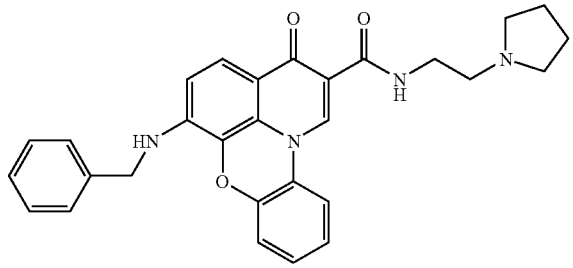

Fluoroquinolone (40 mg), benzylamine (0.05 ml), diisopropylethylamineamine (0.05 ml) and N-methylpyrrolidine were mixed and heated at 190° C. for 15 min in a microwave reactor. The reaction was cooled, evaporated to a residue and purified on a reverse phase C18 column using gradient elution using 0.1% TFA in water and acetonitrile to yield 5 mg of product M+1⁺481. ¹H NMR (CDCl₃) δ 10.08 (t, 1H), 9.17 (s, 1H), 7.86 (d, 1H), 7.53 (d, 1H), 7.37 (d, 2H), 7.31 (m, 1H), 7.16 (m, 1H), 7.06 (d, 1H), 6.83 (d, 1H), 4.92 (t, 1H), 4.53 (d, 2H), 3.61 (q, 2H), 2.74 (t, 2H), 2.6 (m, 4H), 1.80 (m, 4H).

Example 64

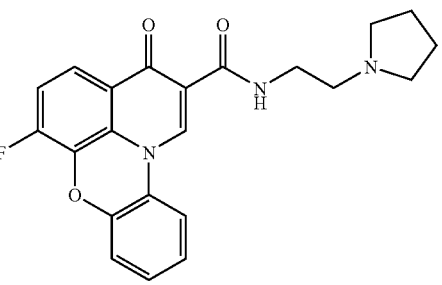

Fluoroquinolone (40 mg), 2-(methyamino)methylmidazole (0.05 ml), diisopropylethylamineamine (0.05 ml) and N-methylpyrrolidine were mixed and heated at 190° C. for 15 min in a microwave reactor. The reaction was cooled, evaporated to a residue and purified on a reverse phase C18 column using gradient elution using 0.1% TFA in water and acetonitrile to yield 11 mg of product M+1⁺485. ¹H NMR (CDCl₃) δ 9.2 (s, 1H), 7.86 (d, 1H), 7.53 (d, 1H), 7.37 (d, 2H), 7.31 (m, 1H), 7.16 (m, 1H), 7.06 (d, 1H), 6.83 (d, 1H), 4.92 (t, 1H), 4.53 (d, 2H), 3.61 (q, 2H), 3.4 (s,3H) 2.74 (t, 2H), 2.6 (m, 4H), 1.80 (m, 4H).

Example 63

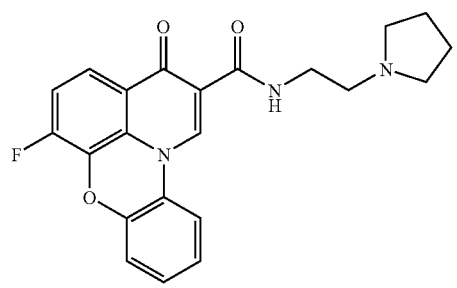

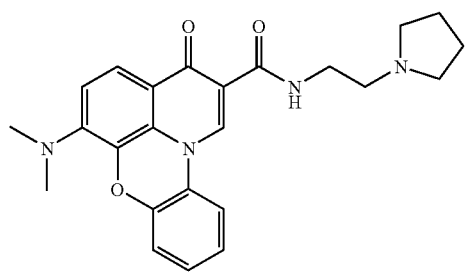

Fluoroquinolone (40 mg), aqueous dimethylamine (0.2 ml), diisopropylethylamineamine (0.05 ml) and N-methylpyrrolidine were mixed and heated at 190° C. for 15 min in a microwave reactor. The reaction was cooled, evaporated to a residue and purified on a reverse phase C18 column using gradient elution using 0.1% TFA in water and acetonitrile to yield 5 mg of product M+1⁺419. ¹H NMR (CDCl₃) δ), 9.17 (s, 1H), 7.86 (d, 1H), 7.53 (d, 1H), 7.37 (d, 2H), 7.31 (m, 1H), 7.16 (m, 1H), 7.06 (d, 1H), 6.83 (d, 1H), 3.1 (t, 2H), 2.8 (s, 6H) 2.6 (t, 2H), 1.60 (t, 2H).

Example 65

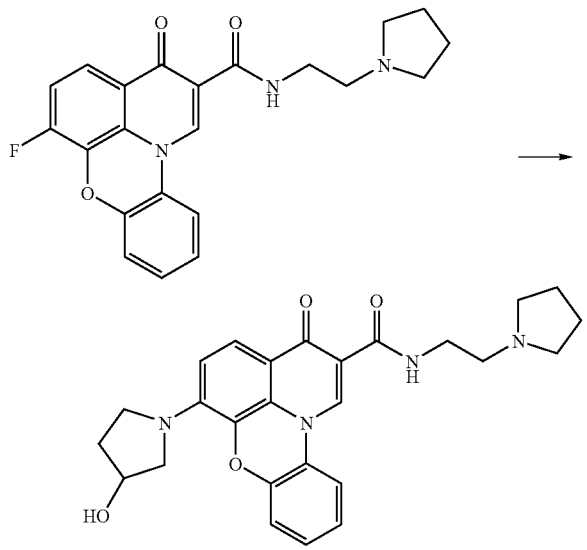

Fluoroquinolone (40 mg), aqueous dimethylamine (0.2 ml), diisopropylethylamineamine (0.05 ml) and N-methylpyrrolidine were mixed and heated at 190° C. for 15 min in a microwave reactor. The reaction was cooled, evaporated to a residue and purified on a reverse phase C18 column using gradient elution using 0.1% TFA in water and acetonitrile to yield 2.5 mg of product M+1$^{+}$461. $^{1}$H NMR (CDCl$_3$) δ), 9.17 (s, 1H), 7.86 (d, 1H), 7.53 (d, 1H), 7.37 (d, 2H), 7.31 (m, 1H), 7.16 (m, 1H), 7.06 (d, 1H), 6.83 (d, 1H), 3.2 (m, 1H), 3.1 (m, 2H), 2.7 (m, 3H), 2.2 (m, 2H), 2.0 (m, 1H), 1.8 (m, 1H), 1.5 (m, 1H).

It is understood that the foregoing detailed description and accompanying examples are merely illustrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

---

The invention claimed is:

1. A compound having formula 2

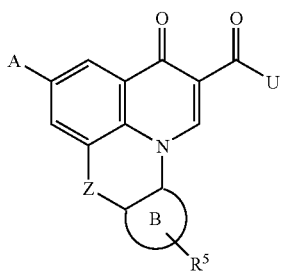

(2)

or a pharmaceutically acceptable salt or ester thereof;

wherein A is $NR^1R^2$;

Z is O; and

U is $NR^1R^2$;

B is a 5-6 membered aryl or heteroaryl;

$R^1$ is independently H or a $C_{1-6}$ alkyl; and $R^2$ is independently H, or a $C_{1-10}$ alkyl or $C_{2-10}$ alkenyl optionally containing one or more non-adjacent heteroatoms selected from N, O, and S, and optionally substituted with a substituted or unsubstituted aryl, heteroaryl, carbocyclic, or heterocyclic ring; or $R^2$ is an optionally substituted cycloalkyl, heterocyclic ring, aryl or heteroaryl;

or $R^1$ and $R^2$ together with N in $NR^1R^2$ may independently form an optionally substituted 5-6 membered ring containing N, and optionally O or S;

$R^5$ is a substituent at any position of B and is H, halo, cyano, azido, —CONHR$^1$, OR$^2$, or $C_{1-6}$ alkyl or $C_{2-6}$ alkenyl, where each $C_{1-6}$ alkyl or $C_{2-6}$ alkenyl is optionally substituted by halo, =O or one or more heteroatoms;

wherein each optionally substituted moiety is substituted with one or more halo, cyano, azido, acetyl, amido, OR$^2$, $NR^1R^2$, carbamate, $C_{1-10}$ alkyl, or $C_{2-10}$ alkenyl, where each $C_{1-6}$ alkyl or $C_{2-6}$ alkenyl is optionally substituted by halo, =O, aryl or one or more heteroatoms selected from N, O and S; or is substituted with an aryl, a carbocyclic or a heterocyclic ring.

2. The compound of claim 1, wherein $R^5$ is halo.

3. The compound of claim 1, wherein B is phenyl.

4. The compound of claim 1, wherein $NR^1R^2$ is independently an optionally substituted morpholine, thiomorpholine, imidazole, pyrrolidine, piperazine, pyridine or piperidine.

5. A pharmaceutical composition comprising the compound of claim 1 and a pharmaceutically acceptable excipient.

6. The compound of claim 1, which is selected from the group consisting of:

199
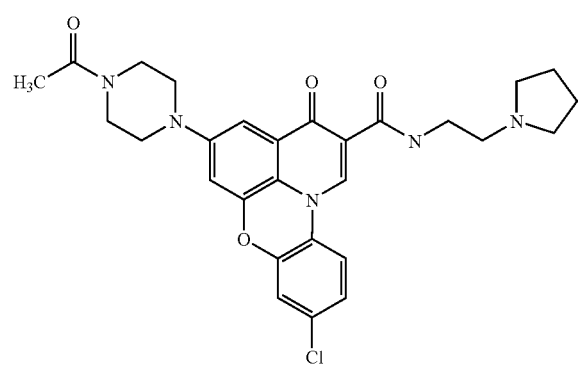
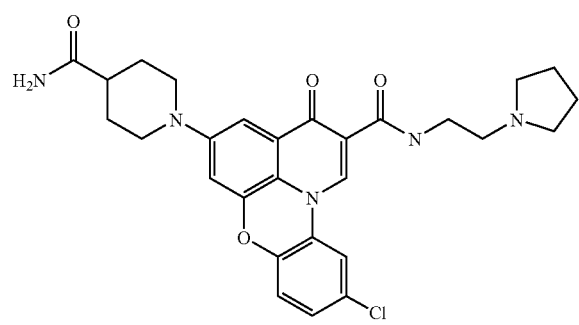
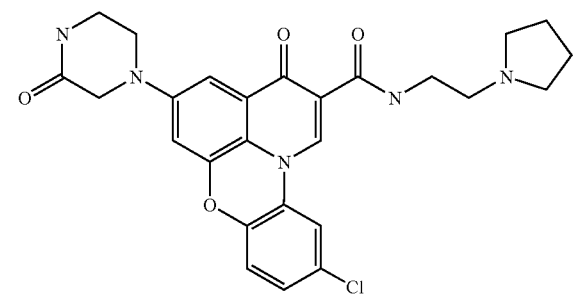
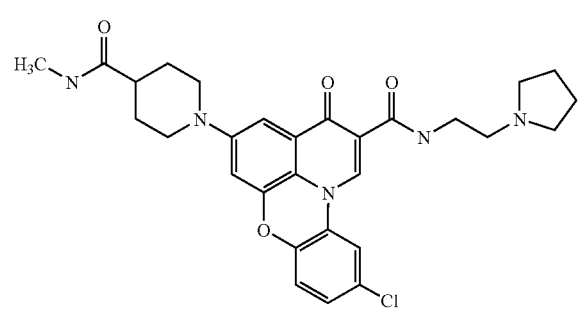
200
-continued
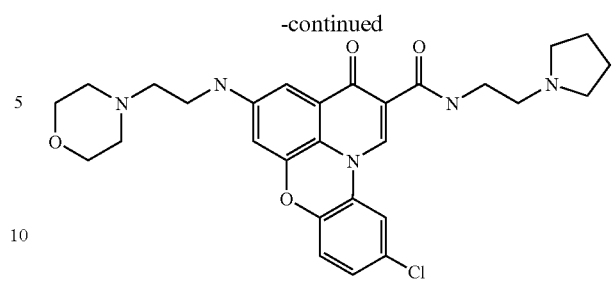
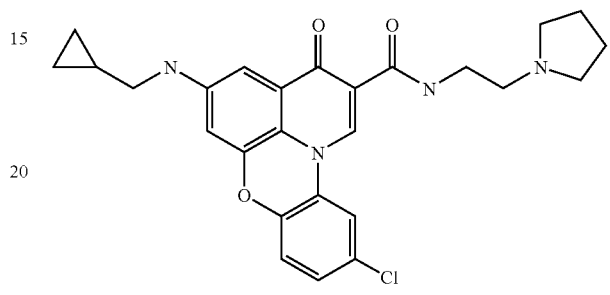
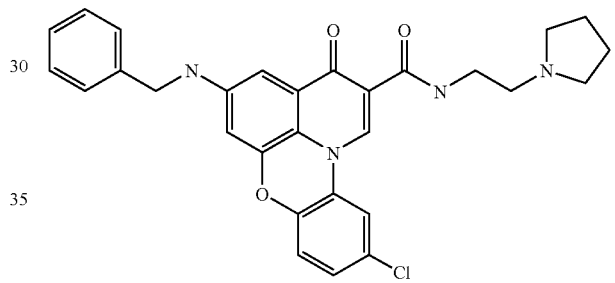
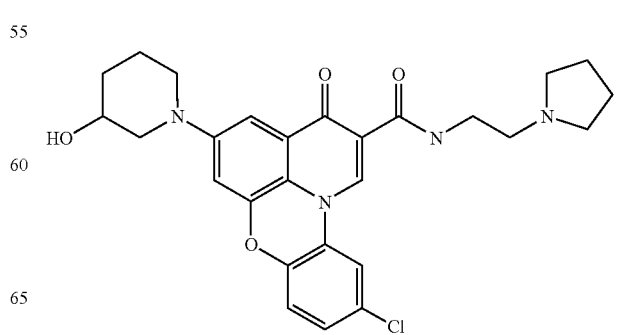

201
-continued
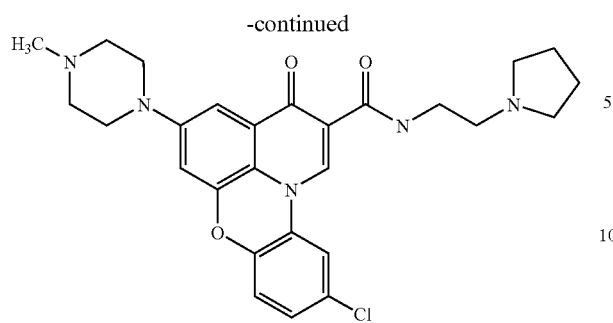
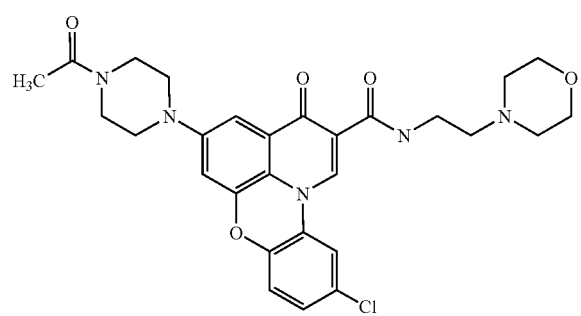
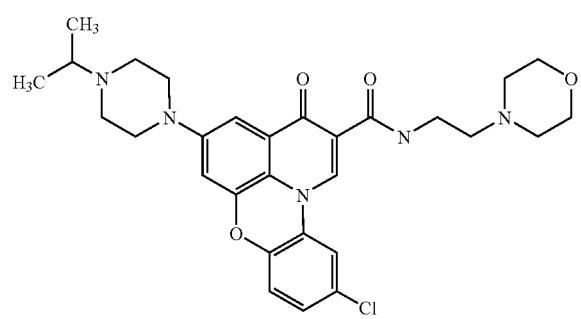
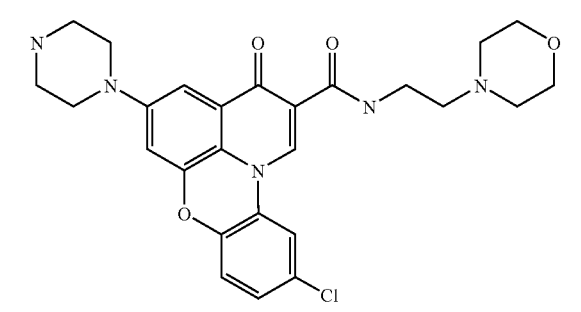
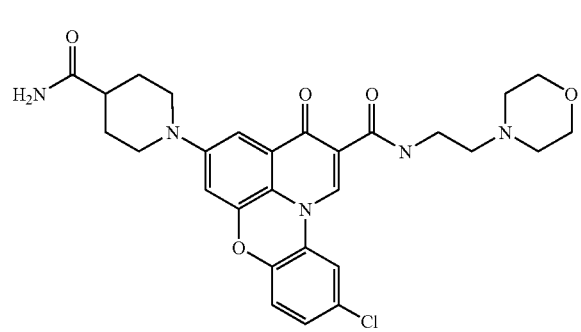
202
-continued
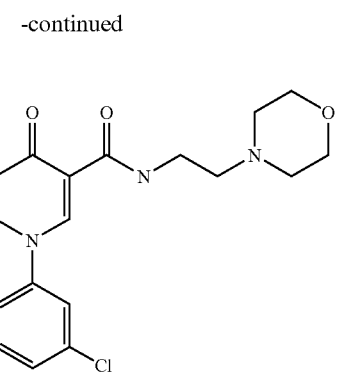
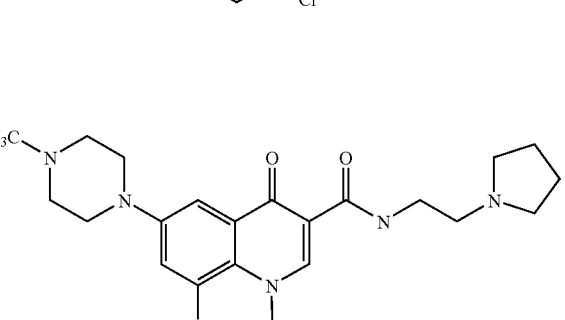
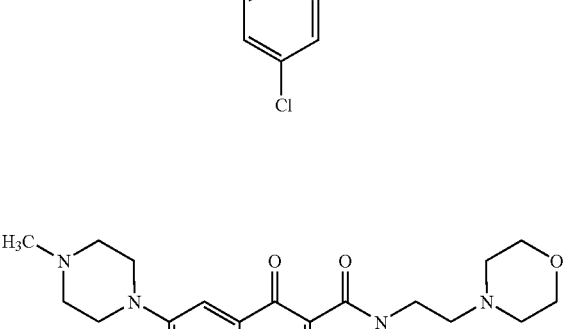
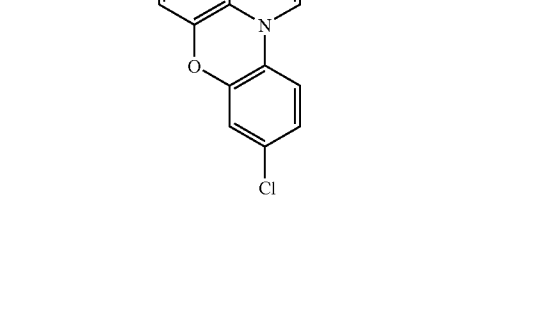
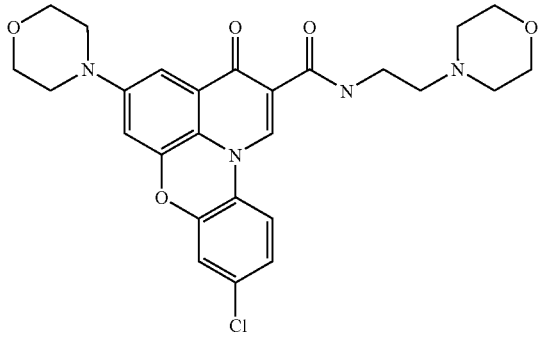

203
-continued
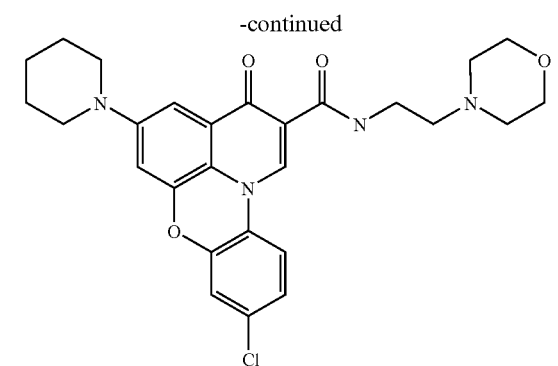
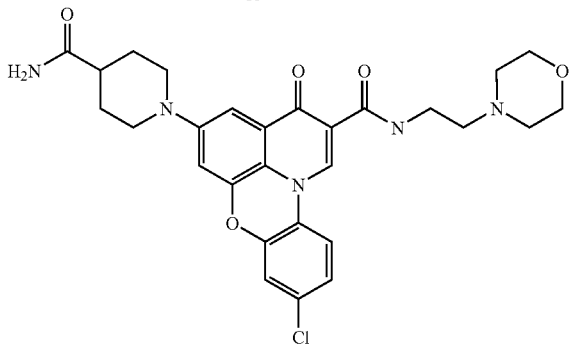
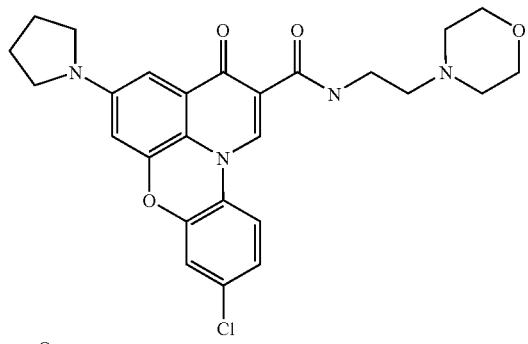
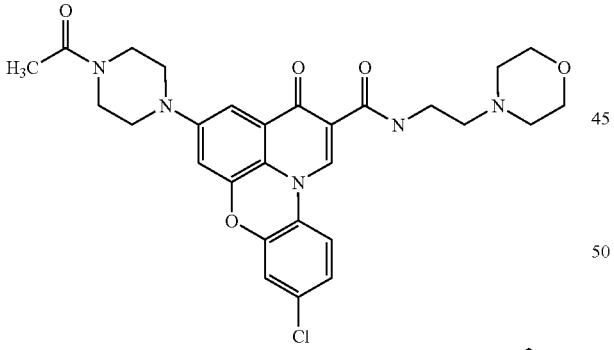
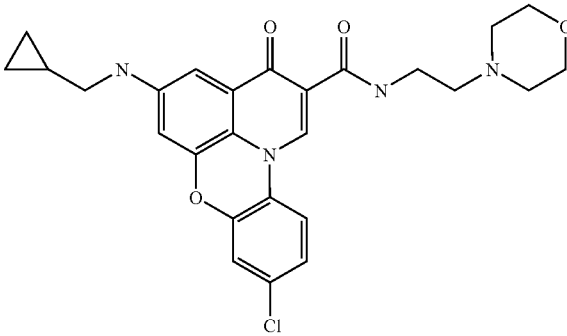
204
-continued
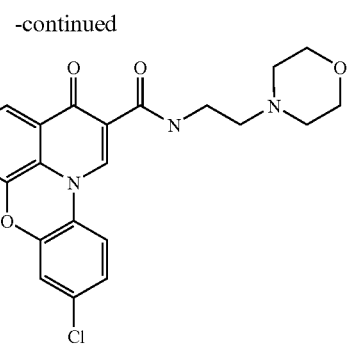
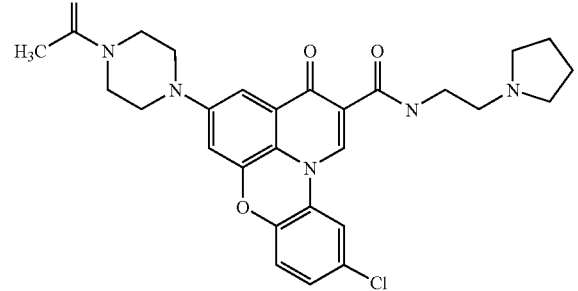
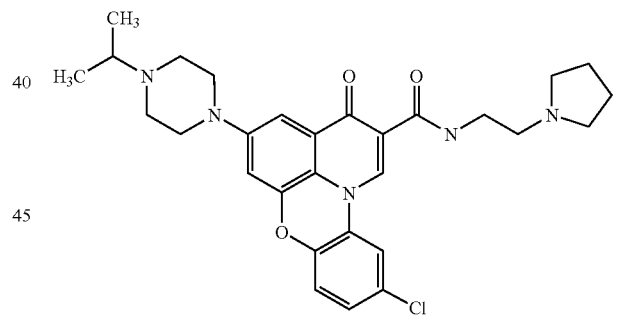
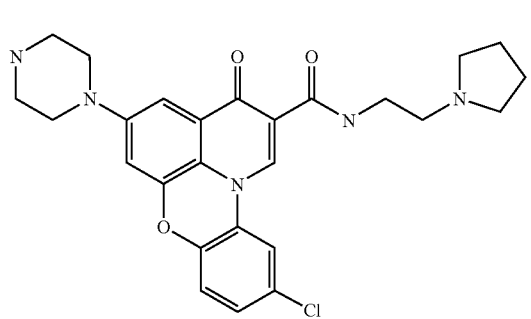

205
-continued
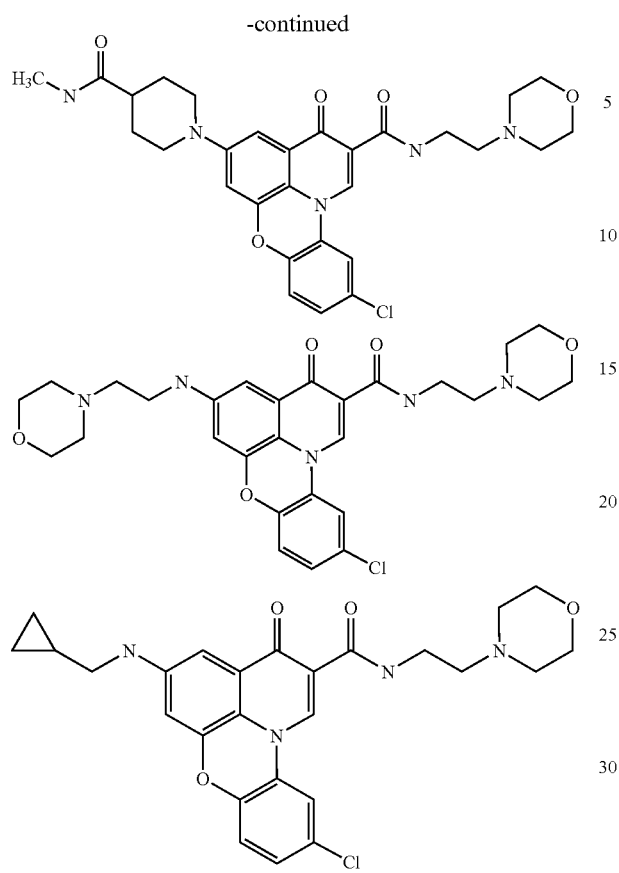
206
-continued
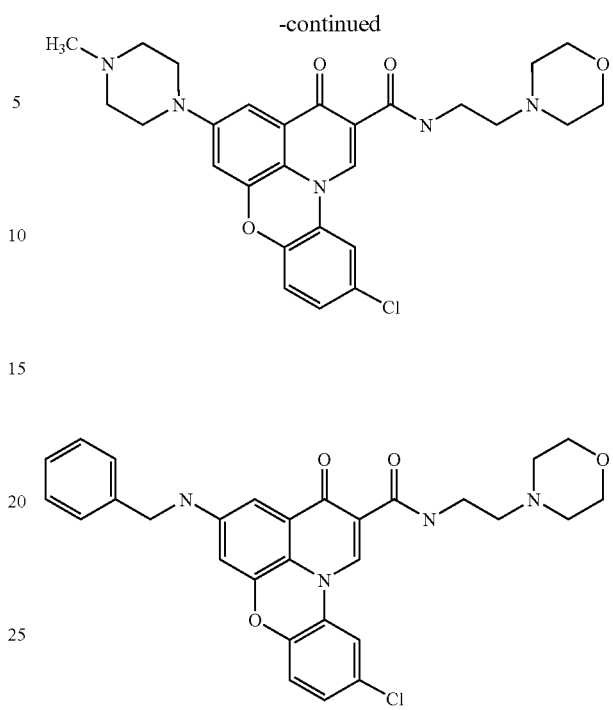
and the pharmaceutically acceptable salts of these.
* * * * *